US011138779B2

(12) United States Patent
Yamagata et al.

(10) Patent No.: US 11,138,779 B2
(45) Date of Patent: Oct. 5, 2021

(54) INFORMATION PROCESSING APPARATUS, INFORMATION PROCESSING METHOD, COMPUTER-READABLE MEDIUM, AND BIOLOGICAL SIGNAL MEASUREMENT SYSTEM

(71) Applicants: Hideaki Yamagata, Kanagawa (JP); Eiichi Okumura, Ishikawa (JP); Noriyuki Tomita, Ishikawa (JP)

(72) Inventors: Hideaki Yamagata, Kanagawa (JP); Eiichi Okumura, Ishikawa (JP); Noriyuki Tomita, Ishikawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/814,054

(22) Filed: Mar. 10, 2020

(65) Prior Publication Data
US 2020/0294296 A1    Sep. 17, 2020

(30) Foreign Application Priority Data

Mar. 14, 2019    (JP) .............................. JP2019-047403

(51) Int. Cl.
*G06T 11/60*    (2006.01)
*A61B 5/00*    (2006.01)
(Continued)

(52) U.S. Cl.
CPC ............ *G06T 11/60* (2013.01); *A61B 5/7425* (2013.01); *A61B 5/0042* (2013.01); *A61B 5/055* (2013.01);
(Continued)

(58) Field of Classification Search
CPC ...................................................... G06T 11/60
(Continued)

(56) References Cited

U.S. PATENT DOCUMENTS 4,744,029 A * 5/1988 Raviv .................... A61B 5/048
600/544
6,073,040 A * 6/2000 Kiyuna .............. A61B 5/04005
600/409
(Continued)

FOREIGN PATENT DOCUMENTS

JP    H03-001839    1/1991
JP    2844859    10/1998
(Continued)

OTHER PUBLICATIONS

Rafael Escovaretal., "Mutual Inductance Extraction and the Dipole Approximation" Apr. 18-21, 2004, Phoenix, Arizona, USA. Copyright 2004 year ACM.*

*Primary Examiner* — Javid A Amini
(74) *Attorney, Agent, or Firm* — Harness, Dickey & Pierce, P.L.C.

(57) ABSTRACT

An information processing apparatus includes a display controller configured to group dipole estimation results with the same direction out of dipole estimation results of a signal source corresponding to part of biological data indicating a chronological change of a biological signal and display the grouped dipole estimation results in a manner superimposed on a plurality of biological tomographic images sliced in a predetermined direction. The display controller is configured to, when displaying a non-grouped dipole estimation result, display the non-grouped dipole estimation result in a different color or form from a color or a form of the grouped dipole estimation results depending on a direction of the dipole estimation result.

17 Claims, 38 Drawing Sheets

(51) Int. Cl.
*A61B 5/055* (2006.01)
*A61B 5/245* (2021.01)
*A61B 5/369* (2021.01)

(52) U.S. Cl.
CPC .............. *A61B 5/245* (2021.01); *A61B 5/369* (2021.01); *G06T 2210/41* (2013.01)

(58) Field of Classification Search
USPC ........................................................ 345/632
See application file for complete search history.

(56) References Cited

U.S. PATENT DOCUMENTS

| | | | | |
|---|---|---|---|---|
| 7,457,653 | B2* | 11/2008 | Fujimaki | G06K 9/0057 324/301 |
| 7,840,039 | B2* | 11/2010 | Fuchs | A61B 5/4064 382/128 |
| 8,478,393 | B2* | 7/2013 | Ramanathan | A61B 5/044 600/523 |
| 2008/0309326 | A1* | 12/2008 | Schechter | A61B 5/06 324/207.12 |
| 2011/0288400 | A1* | 11/2011 | Russell | A61B 5/0035 600/411 |
| 2012/0035685 | A1* | 2/2012 | Saha | A61N 1/37241 607/59 |
| 2012/0101396 | A1* | 4/2012 | Solosko | A61B 5/0432 600/509 |
| 2012/0141003 | A1* | 6/2012 | Wang | G01R 33/24 382/131 |
| 2012/0232376 | A1* | 9/2012 | Crevecoeur | G16H 50/50 600/409 |
| 2013/0109996 | A1* | 5/2013 | Turnbull | A61B 5/7264 600/544 |
| 2013/0324832 | A1* | 12/2013 | Wu | A61B 5/04005 600/409 |
| 2014/0012505 | A1* | 1/2014 | Smith | G01V 3/08 702/2 |
| 2015/0133811 | A1* | 5/2015 | Suzuki | G02C 7/027 600/544 |
| 2015/0192510 | A1* | 7/2015 | Piestun | G01N 15/1456 702/151 |
| 2016/0231401 | A1* | 8/2016 | Wang | A61C 7/125 |
| 2017/0017764 | A1* | 1/2017 | Tsugo | G16H 10/60 |
| 2018/0055394 | A1* | 3/2018 | Sohrabpour | A61B 5/742 |
| 2018/0321347 | A1* | 11/2018 | Wang | A61B 5/7203 |
| 2018/0325483 | A1* | 11/2018 | Shinohara | G06F 3/015 |
| 2019/0021676 | A1* | 1/2019 | Shinohara | A61B 5/04012 |
| 2019/0274640 | A1* | 9/2019 | Mukasa | A61B 5/0476 |
| 2020/0294189 | A1* | 9/2020 | Yamagata | G16H 30/20 |

FOREIGN PATENT DOCUMENTS

| | | |
|---|---|---|
| JP | 2000-005133 | 1/2000 |
| JP | 2002-159459 | 6/2002 |
| JP | 3598380 | 9/2004 |
| JP | 4299781 | 4/2009 |
| JP | 2018-153612 | 10/2018 |
| JP | 2018-153614 | 10/2018 |

* cited by examiner

FIG.7

Annotation List

☑ Show Markup on wave —————————— 180a

| No. | File | Time | Event | MEMO | Cluster |
|---|---|---|---|---|---|
| 2 ☐ | 001 | 00:09:30 | 🔥 | normal spike | B |
| 1 ☐ | 001 | 00:05:00 | 🔥 | strong spike | A |
| 0 ☐ | 000 | 00:00:00 | 🔥 | Dr.memo | A |

180

Exit Measurement

FIG.12

FIG.26
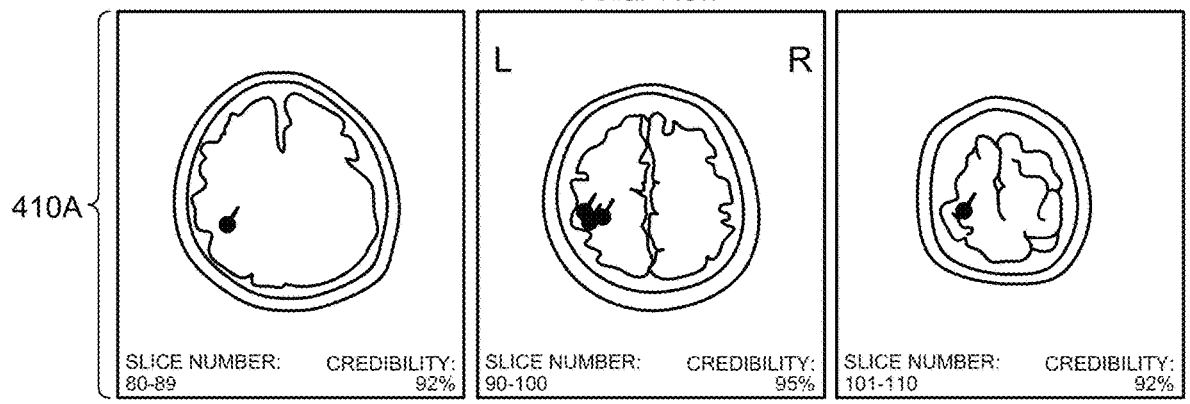
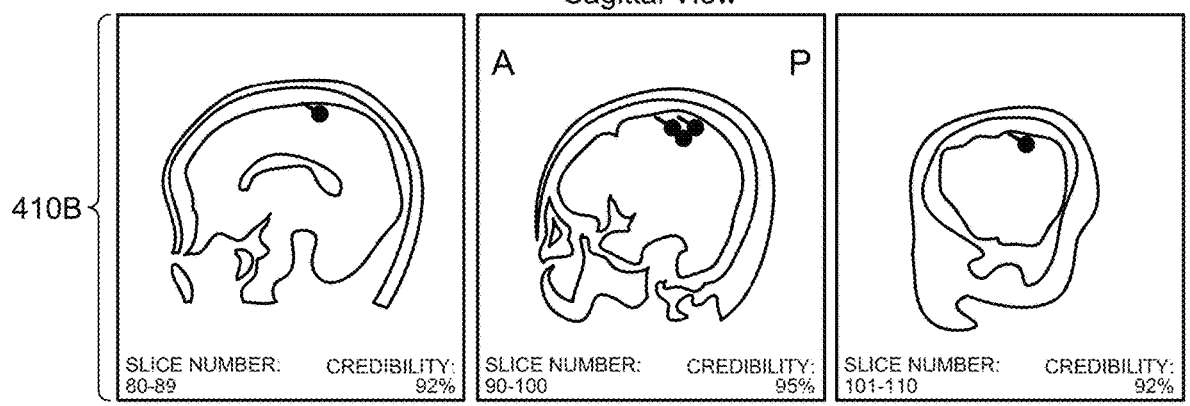
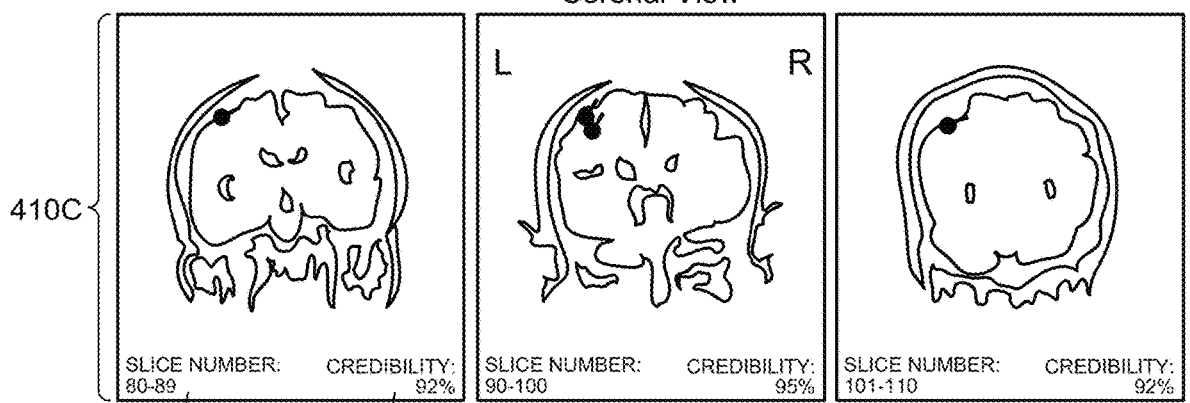

FIG.31A

SIGNAL WAVEFORMS OF ONE MEASUREMENT FILE    SIGNAL WAVEFORMS OF OTHER MEASUREMENT FILE

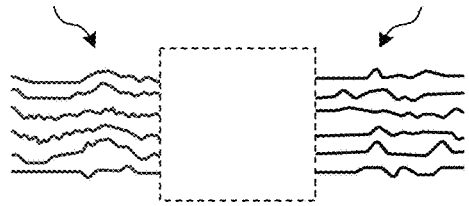

FIG.31B

SIGNAL WAVEFORMS OF ONE MEASUREMENT FILE    SIGNAL WAVEFORMS OF OTHER MEASUREMENT FILE

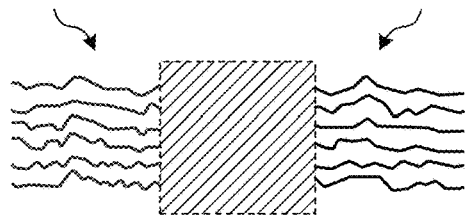

FIG.31C

SIGNAL WAVEFORMS OF ONE MEASUREMENT FILE    SIGNAL WAVEFORMS OF OTHER MEASUREMENT FILE

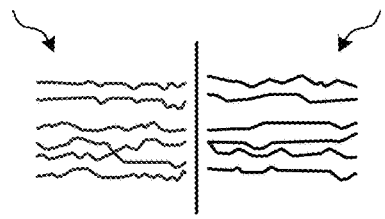

FIG.31D

SIGNAL WAVEFORMS OF ONE MEASUREMENT FILE    SIGNAL WAVEFORMS OF OTHER MEASUREMENT FILE

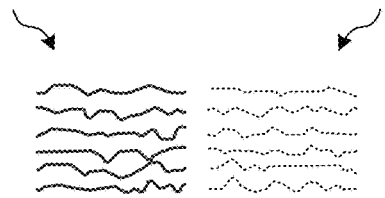

FIG.31E

SIGNAL WAVEFORMS OF ONE MEASUREMENT FILE    SIGNAL WAVEFORMS OF OTHER MEASUREMENT FILE

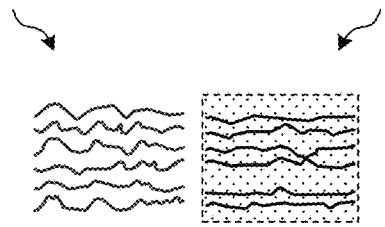

FIG.34
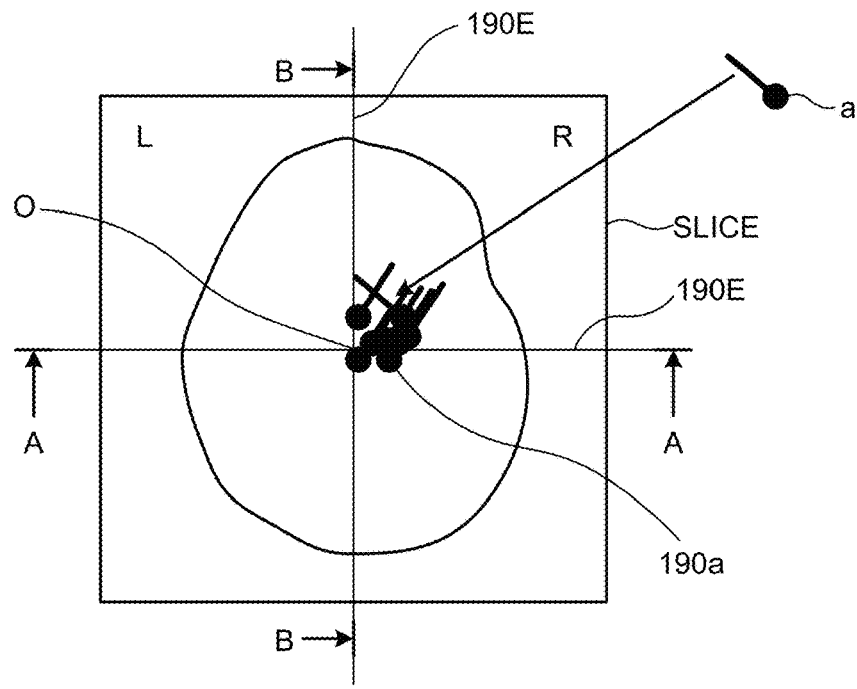
FIG.35
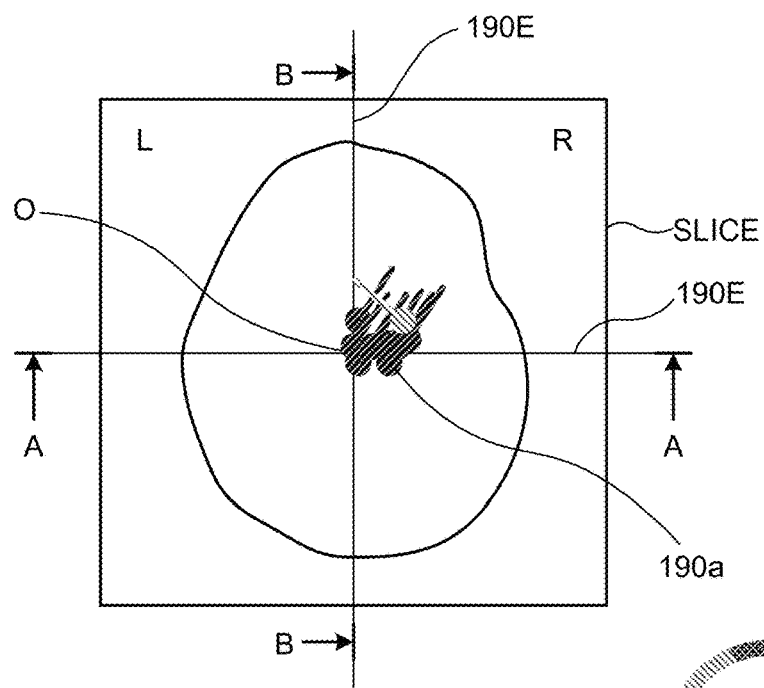
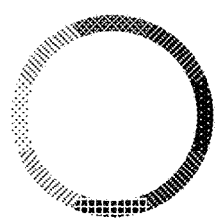

GROUP 1: ●
GROUP 2: ○
GROUP 3: ◉

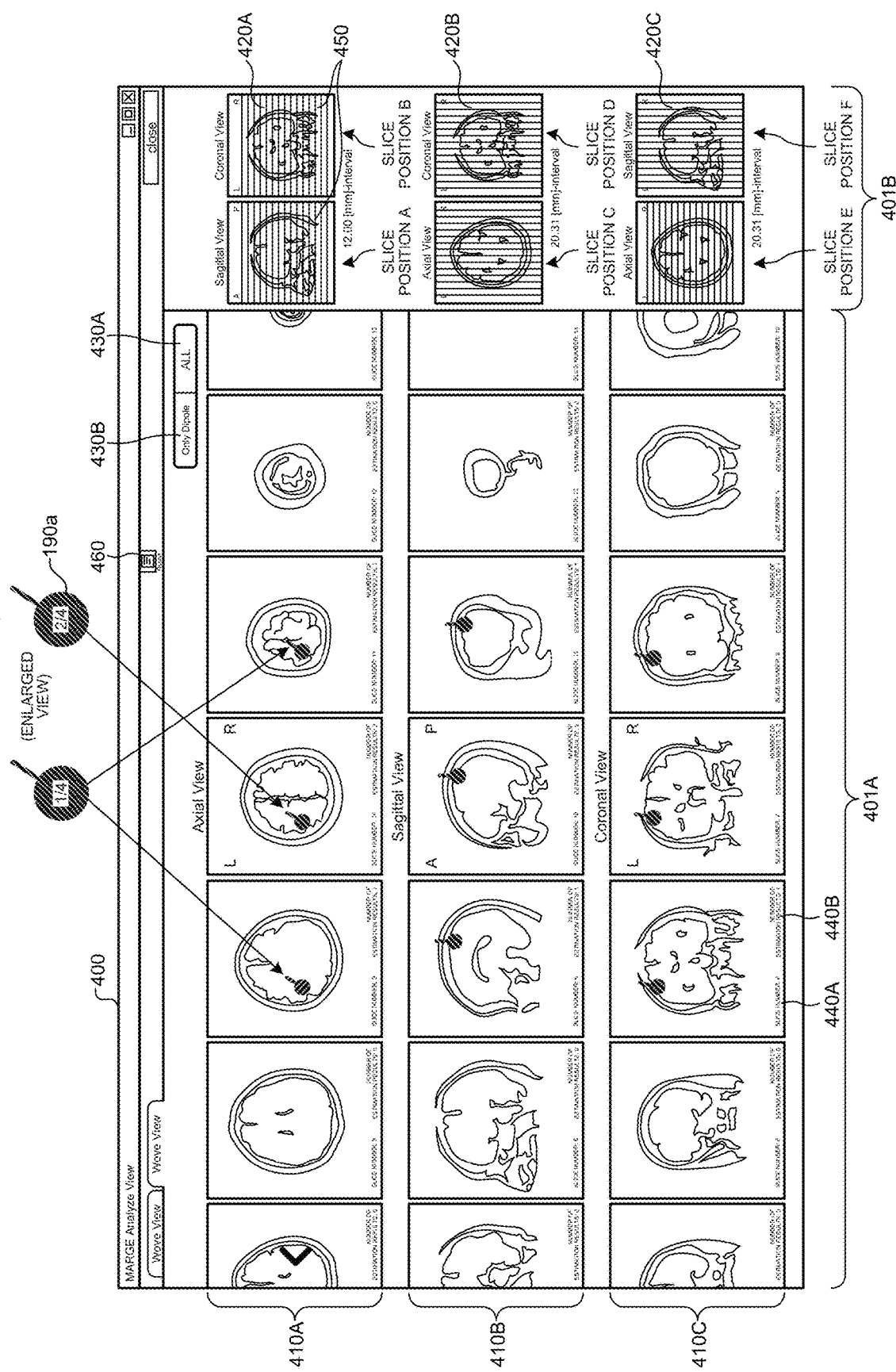

INFORMATION PROCESSING APPARATUS, INFORMATION PROCESSING METHOD, COMPUTER-READABLE MEDIUM, AND BIOLOGICAL SIGNAL MEASUREMENT SYSTEM

CROSS-REFERENCE TO RELATED APPLICATIONS

The present application claims priority under 35 U.S.C. § 119 to Japanese Patent Application No. 2019-047403, filed on Mar. 14, 2019. The contents of which are incorporated herein by reference in their entirety.

BACKGROUND OF THE INVENTION

1. Field of the Invention

The present invention relates to an information processing apparatus, an information processing method, a computer-readable medium, and a biological signal measurement system.

2. Description of the Related Art

Conventionally known are techniques for displaying a signal source in a living body estimated based on measured biological signals of a subject in a manner superimposed on a tomographic image and displaying the waveforms of the biological signals corresponding to the signal source in parallel on a screen (refer to Japanese Unexamined Patent Application Publication No. 2000-5133, for example). In the technique, when an operator specifies a desired time on the displayed waveforms of the biological signals, display is performed to identify the position of the corresponding signal source on the tomographic image.

Magnetoencephalographs and electroencephalographs that measure nerve activity in a brain, for example, determine a waveform position (hereinafter, referred to as a singular point) characteristic of epilepsy from measured waveforms, estimate a signal source from the singular point, and display a dipole estimation result of the signal source in a manner superimposed on a tomographic image. Based on the position of the signal source on the tomographic image, an operator identifies a position (point serving as the cause of epilepsy) to be removed in surgery.

When displaying the dipole estimation results of a plurality of times, however, the conventional technique displays all the dipole estimation results in a superimposed manner, making it difficult to perform an analysis.

SUMMARY OF THE INVENTION

According to an aspect of the present invention, an information processing apparatus includes a display controller configured to group dipole estimation results with the same direction out of dipole estimation results of a signal source corresponding to part of biological data indicating a chronological change of a biological signal and display the grouped dipole estimation results in a manner superimposed on a plurality of biological tomographic images sliced in a predetermined direction. The display controller is configured to, when displaying a non-grouped dipole estimation result, display the non-grouped dipole estimation result in a different color or form from a color or a form of the grouped dipole estimation results depending on a direction of the dipole estimation result.

BRIEF DESCRIPTION OF THE DRAWINGS

FIG. 7 is a view of an updated annotation list;

FIG. 12 is a view of the screen displayed just after a specific annotation line is selected on the analysis screen;

FIG. 26 is a view of the screen displayed when the merge button is pressed according to a modification of the first embodiment;

FIGS. 31A to 31E are views for explaining a display method for distinguishing signal waveforms of respective pieces of range information;

FIG. 34 is a view for explaining a third embodiment of the present invention and illustrating a case where a dipole estimation result is added;

FIG. 35 is a view of an example of a slice image that displays the dipole estimation results according to the third embodiment;

FIG. 47 is a view of an example obtained by reflecting the display illustrated in FIG. 46 on the screen illustrated in FIG. 19.

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
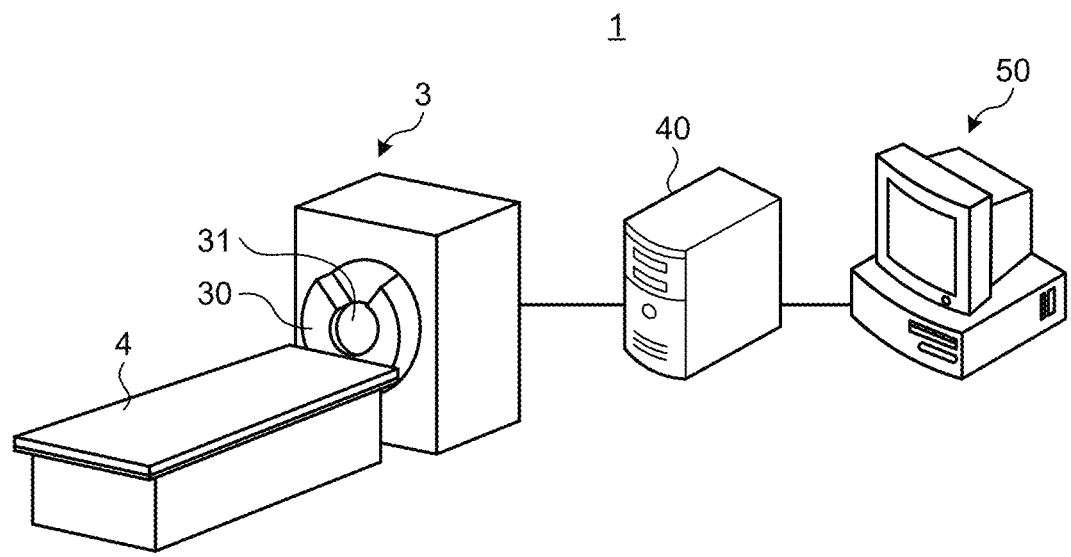
FIG. 1 is a schematic of a biological signal measurement system according to an embodiment of the present invention.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An embodiment has an object to increase the visibility of dipole estimation results of a plurality of times.

Exemplary embodiments of an information processing apparatus, an information processing method, a computer-readable medium, and a biological signal measurement system according to the present invention are described below in further detail with reference to the accompanying drawings.

First Embodiment

FIG. 1 is a schematic of a biological signal measurement system 1 according to an embodiment. The biological signal measurement system 1 measures and displays a plurality of kinds of biological signals of a subject, such as magnetoencephalography (MEG) signals and electroencephalography (EEG) signals. The biological signals to be measured are not limited to the MEG signals and the EEG signals and may be electrical signals generated based on activity of a heart (electrical signals displayable as an electrocardiogram), for example. As illustrated in FIG. 1, the biological signal measurement system 1 includes a measuring apparatus 3, a server 40, and an information processing apparatus 50. The measuring apparatus 3 measures one or more biological signals of the subject. The server 40 records the one or more biological signals measured by the measuring apparatus 3. The information processing apparatus 50 analyzes the one or more biological signals recorded in the server 40. While the server 40 and the information processing apparatus 50 are separated in FIG. 1, at least part of the functions of the server 40, for example, may be incorporated in the information processing apparatus 50.

In the example illustrated in FIG. 1, the subject (person to be measured) lies on the back on a measurement table 4 with electrodes (or sensors) for EEG on the head and puts the head into a recess 31 of a dewar 30 of the measuring apparatus 3. The dewar 30 is a cryogenic container using liquid helium. The inside of the recess 31 of the dewar 30 is provided with a number of magnetic sensors for MEG. The measuring apparatus 3 collects the EEG signals from the electrodes and the MEG signals from the magnetic sensors and outputs data including the collected EEG and MEG signals (which may be hereinafter referred to as "measurement data") to the server 40. The measurement data recorded in the server 40 is read, displayed, and analyzed by the information processing apparatus 50. While the dewar 30 including the magnetic sensors and the measurement table 4 are usually disposed in a magnetic shielding room, the magnetic shielding room is not illustrated for the convenience of explanation.

The information processing apparatus 50 displays waveforms of the MEG signals from the magnetic sensors and waveforms of the EEG signals from the electrodes in synchronization on the same time axis. The EEG signal represents electrical activity of a nerve cell (flow of an ionic charge generated at a dendrite of a neuron in synaptic transmission) as a voltage value between the electrodes. The MEG signal represents minute magnetic field fluctuations generated by electrical activity of a brain. The brain magnetic field is detected by a highly sensitive superconducting quantum interference device (SQUID) sensor. The EEG signal and the MEG signal are examples of the "biological signal".

Figure 2:
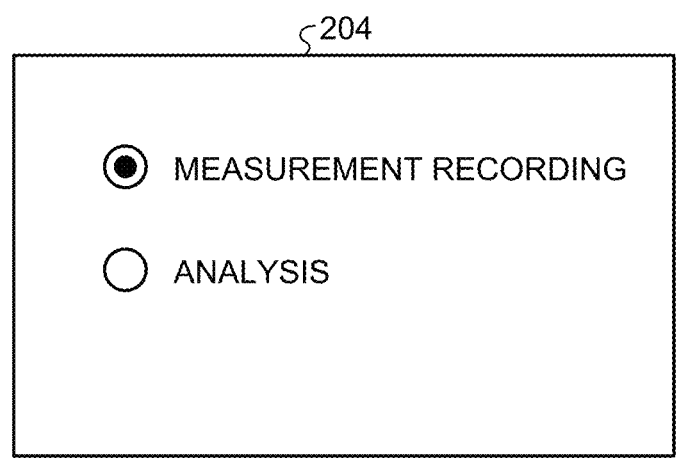
FIG. 2 is a view of an example of a start screen displayed on an information processing apparatus.

FIG. 2 is a view of an example of a start screen 204 displayed on the information processing apparatus 50. The start screen 204 displays buttons for selecting "measurement recording" and "analysis". In EEG and/or MEG, measurement recording and an analysis of data are performed frequently by different subjects. If a measurement technician (measurer) selects the "measurement recording" button, for example, the data measured by the measuring apparatus 3 is stored in the server 40 and read and displayed by the information processing apparatus 50. If a doctor selects the "analysis" button after the end of measurement recording, the recorded measurement data is read and analyzed.

Operations in Measurement Recording

Figure 3:
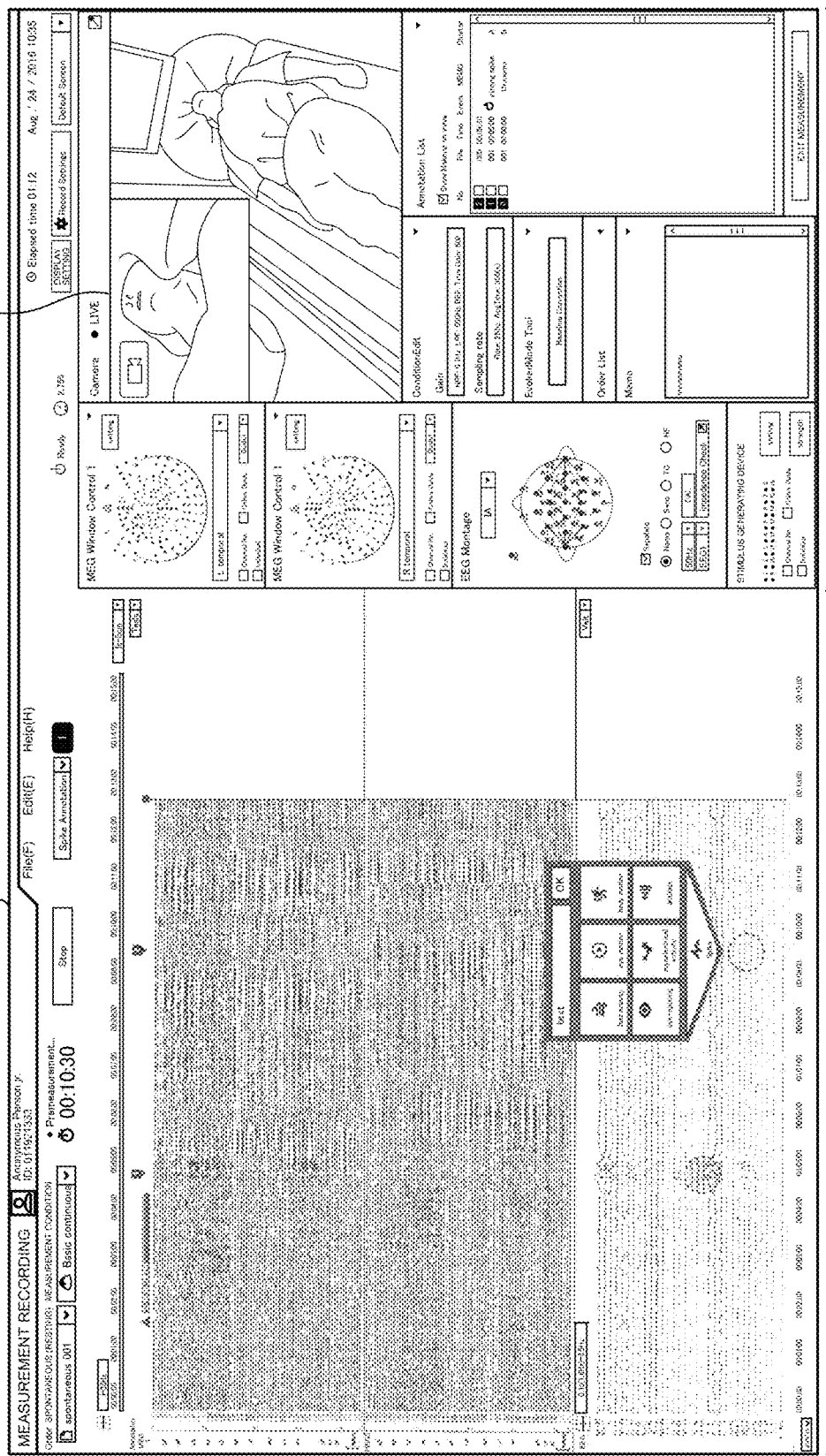
FIG. 3 is a view of an example of a measurement recording screen.

FIG. 3 is a view of an example of a measurement recording screen. A tab 111 on the screen indicates that the screen is the "measurement recording" screen. The measurement recording screen includes a region 201A and a region 201B. The region 201A displays measured signal waveforms. The region 201B displays monitor information other than the signal waveforms. The region 201A that displays the signal waveforms is disposed in the left part of the screen viewed from the measurer, and the region 201B that displays the monitor information other than the signal waveforms is disposed in the right part of the screen viewed from the measurer. This layout requires no useless motion between the movement of the measurer's line of sight corresponding to the movement of the waveforms detected and displayed in real time (displayed from the left to the right of the screen) and the movement of a mouse from the left region 201A to the right region 201B of the screen, thereby improving working efficiency.

The region 201B of the display screen displays a monitor window 170 for checking the state of the person to be measured during the measurement. Displaying live video of the person to be measured during the measurement can increase the reliability of checking and determining the signal waveforms, which will be described later. While the entire measurement recording screen is displayed on the display screen of one monitor display (display device 28, which will be described later) in FIG. 3, the left region 201A and the right region 201B may be displayed separately on two or more monitor displays.

Figure 4:
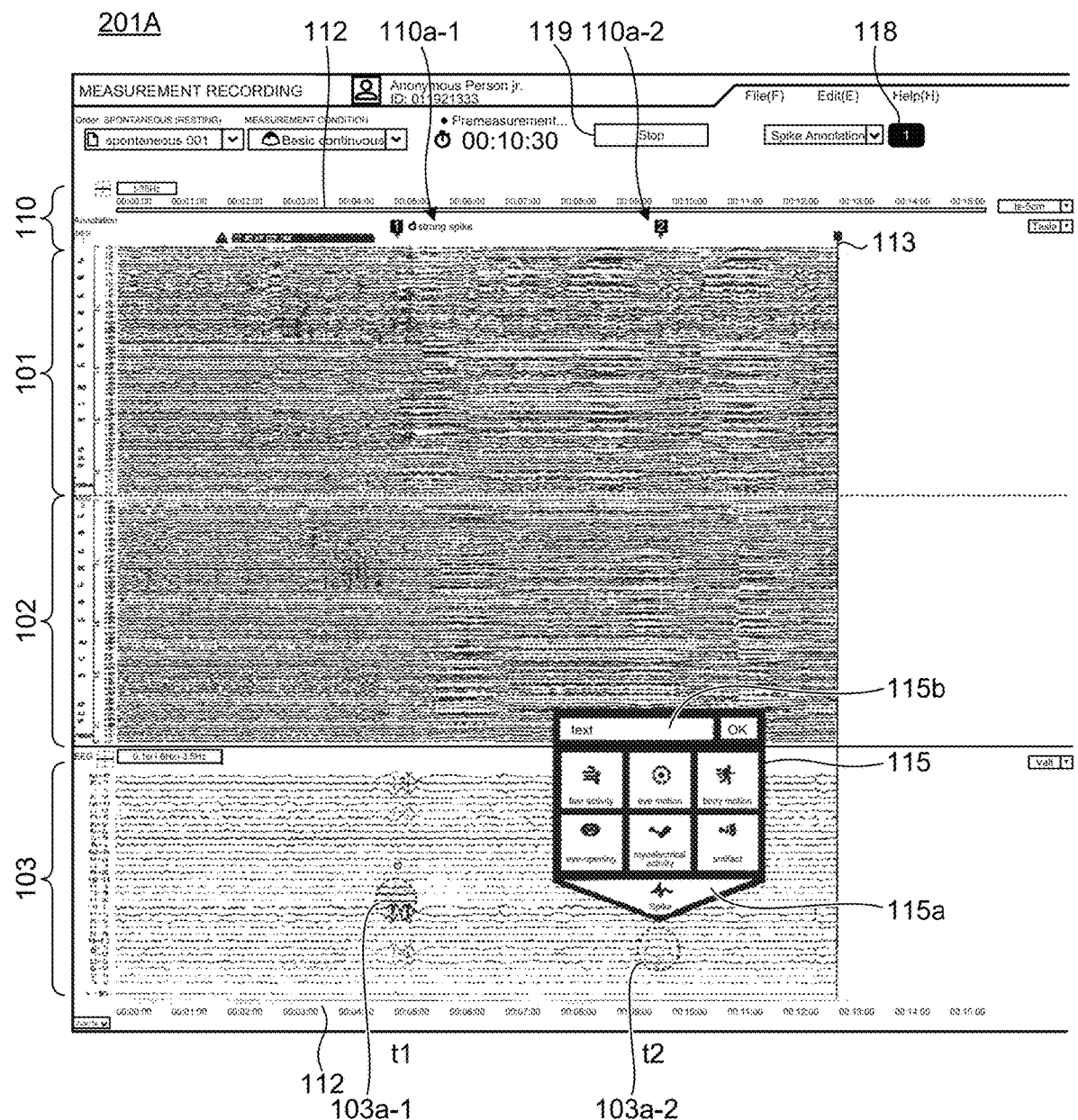
FIG. 4 is an enlarged view of a left region of the measurement recording screen.

FIG. 4 is an enlarged view of the left region 201A illustrated in FIG. 3. The region 201A includes a first display region 110 and second display regions 101 to 103. The first display region 110 displays time information on signal detection in the horizontal direction (first direction) of the screen. The second display regions 101 to 103 display a plurality of signal waveforms based on signal detection in parallel in the vertical direction (second direction) of the screen.

In the example illustrated in FIG. 4, the time information displayed in the first display region 110 is a time line including times displayed along a time axis 112. The first display region 110 may display only the belt-like axis without displaying any time (number) or only the times (numbers) without displaying any axis. Furthermore, the time line may be displayed by displaying the time axis 112 under the display region 103 besides the display region 110 in the upper part of the screen.

The region 201A displays a plurality of signal waveforms acquired from a plurality of the same kind of sensors or a plurality of kinds of signal waveforms acquired from a groups of a plurality of kinds of sensors in synchronization on the same time axis 112. The display region 101, for example, displays the waveforms of a plurality of MEG signals acquired from the right part of the head of the person to be measured in parallel, and the display region 102 displays the waveforms of a plurality of MEG signals acquired from the left part of the head of the person to be measured in parallel. The display region 103 displays the waveforms of a plurality of EEG signals in parallel. These EEG signal waveforms are voltage signals measured between the electrodes. The signal waveforms are each displayed in a manner associated with an identification number or a channel number of the sensor from which the signal is acquired.

If measurement is started, and measurement information is collected from the sensors, the signal waveforms are displayed from the left end toward the right direction in the display regions 101 to 103 of the region 201A over time. A line 113 represents the time of measurement (present time) and moves from the left to the right on the screen. If the signal waveforms are displayed to the right end (right end of the time axis 112) of the region 201A, the signal waveforms gradually disappear from the left end to the right on the screen. Subsequently, other signal waveforms are sequentially displayed at the disappearing position from the left toward the right direction, and the line 113 also moves from the left end to the right. Simultaneously with this, the display region 110 in the horizontal direction displays the lapse of time on the time axis 112 corresponding to the proceeding of the measurement. Measurement recording is continued until a stop button 119 is pressed.

The embodiment enables the measurer (recorder) to mark a point or a range to be issued on the signal waveforms when the measurer (recorder) notices disturbance of the waveforms on the signal waveforms or a singular point in amplitude, for example, during the recording of data. The point or the range of the marking can be specified by a pointer operation or a click operation using the mouse. The specified point (or range) is highlighted on the signal waveforms in the display regions 101 to 103 and displayed along the time axis 112 in the display region 110 at the time position or the time range corresponding to the specification result. The marking information including display on the time axis 112 is stored with signal waveform data. The specified point corresponds to certain time, and the specified range corresponds to a certain range including the certain time.

In the example illustrated in FIG. 4, a range including one or more channels is specified in the display region 103 at time t1, and the time including time t1 is highlighted in a mark 103a-1. An annotation 110a-1 indicating the specification result is displayed at the corresponding time position in the display region 110 in a manner associated with the display of the mark 103a-1. At time t2, another waveform position or an area near the waveform position is marked in the display region 103, and a mark 103a-2 is highlighted at the position (time t2) or the neighboring area (specifying at least one of the time range and a plurality of waveforms). Simultaneously, an annotation 110a-2 is displayed at the corresponding time position (time range) in the display region 110. The annotation is attachment of related information to certain data as a note. The annotation according to the present embodiment is displayed as a note based on at least the specified time information and is displayed as a note in a manner associated with the position of the waveforms based on at least the time information. If a plurality of channels are displayed, the annotation may be displayed as a note in a manner associated with the corresponding channel information.

The annotation 110a-1 added to the display region 110 at time t1 includes an annotation identification number and information indicating the attributes of the waveforms, for example. In this example, the annotation 110a-1 includes an annotation number "1", an icon indicating the attributes of the waveforms, and text information "strong spike".

If the measurer specifies another waveform position or an area near the waveform position at time t2, the mark 103a-2 is highlighted at the specified point, and an annotation number "2" is displayed at the corresponding time position in the display region 110. Furthermore, a popup window 115 for selecting the attributes is displayed at the highlighted point. The popup window 115 includes selection buttons 115a and an input box 115b. The selection buttons 115a are used to select various attributes. The input box 115b is used to input a comment or additional information. The selection buttons 115a display causes of disturbance of the waveforms, such as "fast activity", "eye motion", "body motion", and "spike", as the attributes of the waveforms. The measurer can check the state of the person to be measured in the monitor window 170 of the region 201B on the screen, thereby appropriately selecting the attribute indicating the cause of disturbance of the waveforms. If a spike occurs in the waveforms, for example, it can be determined whether the spike indicates a symptom of epilepsy or is caused by a body motion (e.g., a sneeze) of the person to be measured.

The same operation is also performed at time t1. In FIG. 4, the selection button 115a "spike" is selected in the popup window 115, and "strong spike" is input to the input box 115b. As a result, the annotation 110a-1 is displayed in the display region 110. If a number of signal waveforms are displayed in synchronization on the same time axis 112, this display form can facilitate the measurer's identifying a point or a range of interest in the signal waveforms by visual recognition and grasping the basic information on the point of interest.

Part or the whole of the annotation 110a-1, that is, at least one of the attribute icon and the text annotation, for example, may be displayed near the mark 103a-1 on the signal waveforms in the display region 103. Addition of the annotation onto the signal waveforms may possibly be an obstacle in checking the waveform shape. To display the annotation onto the signal waveforms in the display regions 101 to 103, display or non-display of the annotation is preferably selectable.

A counter box 118 displays a cumulative number of spike annotations. Every time "spike" is selected, the counter number of the counter box 118 is incremented. As a result, the measurer can find out the total number of spikes from the start of recording to the present time (line 113) at a glance.

Figure 5:
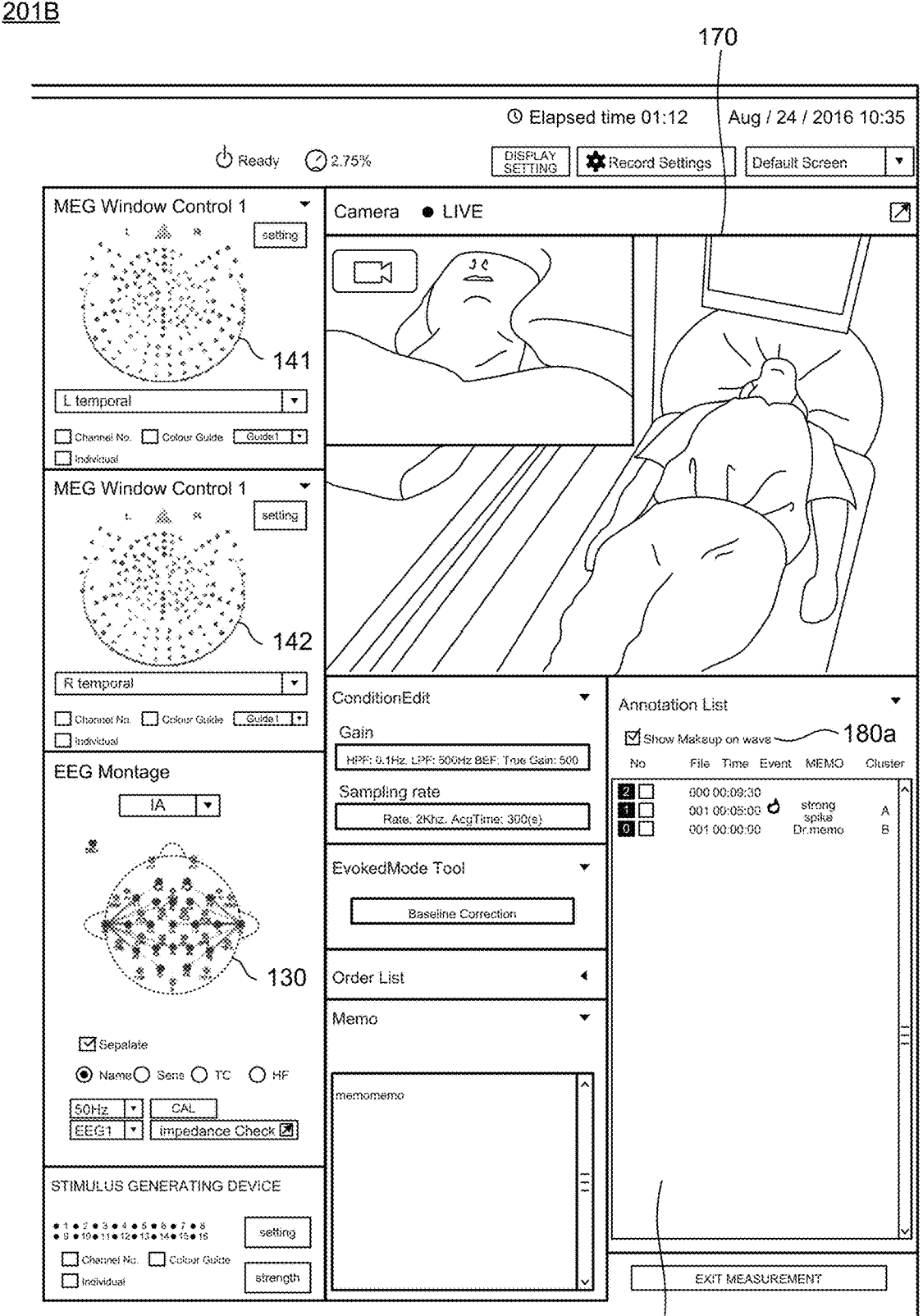
FIG. 5 is an enlarged view of a right region of the measurement recording screen.

FIG. 5 is an enlarged view of the right region 201B illustrated in FIG. 3 and illustrates the state at the same time (time of the line 113) as FIG. 4. The monitor window 170 of the region 201B displays the live video of the state of the person to be measured lying on the measurement table 4 with the head put into the measuring apparatus 3. The region 201B displays distribution maps 141, 142, and 130 and an annotation list 180. The distribution maps 141, 142, and 130 correspond to the signal waveforms in the display regions 101, 102, and 103, respectively. The annotation list 180 is a list of the annotations marked on the signal waveforms illustrated in FIG. 4. Every time a position or a range on the signal waveforms is specified in the display regions 101 to 103, and an annotation is attached, the corresponding information is sequentially added to the annotation list 180. While the annotations are added and displayed in the annotation list 180 on the measurement recording screen in a descending order (displaying new data at the top), for example, the present embodiment is not limited thereto. Alternatively, the annotation list 180 displays the annotations in an ascending order. Also in this case, the annotations are displayed such that the measurer can find out their correspondence with the annotations displayed along the time axis 112 in the display region 110. Furthermore, the annotations can be displayed in other orders and sorted by item.

In the example illustrated in FIG. 5, the time information corresponding to the annotation number "1" and the added annotation information are listed. An attribute icon indicating "spike" and a text "strong spike" are recorded as the annotation information. At the time when the mark 103a-1 is highlighted, the time information corresponding to the annotation number "2" is listed. The "annotation" may be considered as a combination of the annotation number, the time information, and the annotation information, only the annotation information, or a combination of the annotation information and the annotation number or the time information.

A selection box 180a for selecting display/non-display is disposed near the annotation list 180. If non-display is selected in the selection box 180a, the annotations other than the highlight marks on the signal waveforms are not displayed in the display regions 101 to 103. By contrast, the annotations along the time axis 112 in the display region 110 are kept displayed. This mechanism enables the measurer to recognize the annotation information without reducing the visibility of the signal waveforms.

Figure 6:
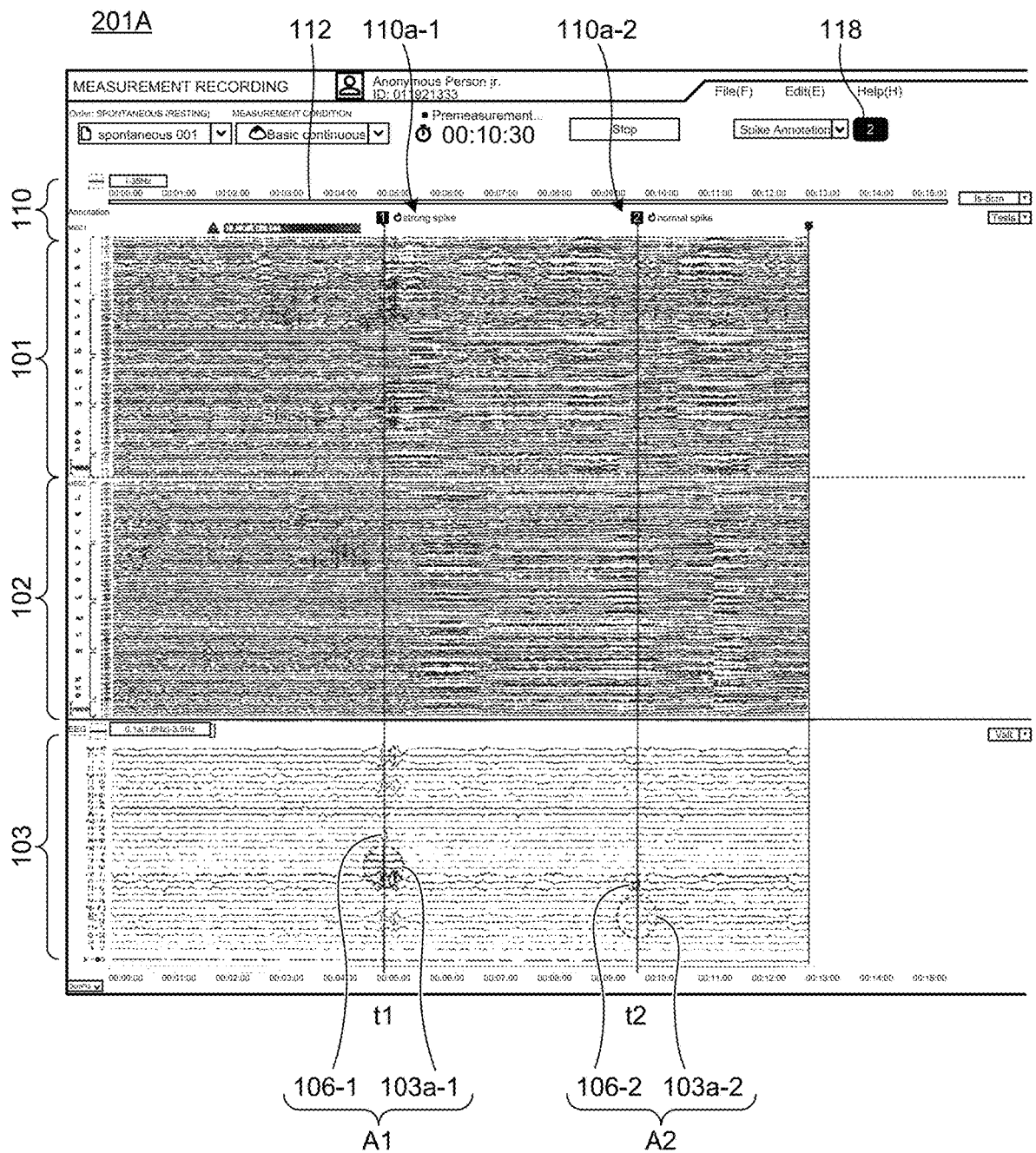
FIG. 6 is a view of the screen displayed just after annotation information is input.

FIG. 6 is a view of the screen displayed just after "spike" is selected in the popup window 115 at time t2, and a text "normal spike" is input. If an "OK" button is selected in the popup window 115 illustrated in FIG. 4, the popup window 115 is closed, and the annotation 110a-2 is displayed at the corresponding time position in the display region 110 as illustrated in FIG. 6. The attribute icon indicating "spike" and text information "normal spike" are displayed corresponding to the annotation number "2". Simultaneously with this, the value of the counter box 118 is incremented. Furthermore, an attribute icon 106-2 is displayed near the highlighted mark 103a-2. While an attribute icon 106-1 is displayed near the mark 103a-1 in this example, display or non-display of the attribute icons 106-1 and 106-2 is selectable as described above. An annotation A1 including the mark 103a-1 and the attribute icon 106-1 and an annotation A2 including the mark 103a-2 and the attribute icon 106-2 are included in the annotation information.

FIG. 7 is a view of the annotation list 180. The annotation list 180 is updated by the addition of the annotation corresponding to the mark 103a-2 is added in the left region 201A on the screen. The memo "normal spike" is added to the annotation number "2".

In the same manner as described above, every time a specific point or range on the signal waveforms is specified in the region 201A during the measurement, the specified point is highlighted, and the annotation information is displayed along the time axis 112 in the display region 110. In the region 201B, the annotation information is sequentially added to the annotation list 180.

In the annotation list 180 and the region 201A for displaying the signal waveforms, the annotation numbers are not necessarily displayed and may not be used. Any desired information may be used as the identification information as long as it enables identification of the added annotation. The attribute icon and the attribute character string (e.g., "strong spike"), for example, may be displayed near the time axis 112 in a manner associated with the corresponding time. Furthermore, file numbers (numbers displayed in the item "File" in FIG. 7) may also be displayed in the region 201A.

If the stop button 119 (illustrated in FIG. 4) is selected (pressed), and the measurement is ended, the highlight point specified in the display regions 101 to 103 is stored corresponding to the signal waveforms. The annotation information displayed at the corresponding time position in the display region 110 is also stored in a manner associated with the annotation number and the time. The related information, such as the counter value of the counter box 118 and the contents in the annotation list 180, is also stored. Storing these pieces of display information can facilitate an analyzer's recognizing and analyzing a point to be issued if the analyzer is different from the measurer.

Figure 8:
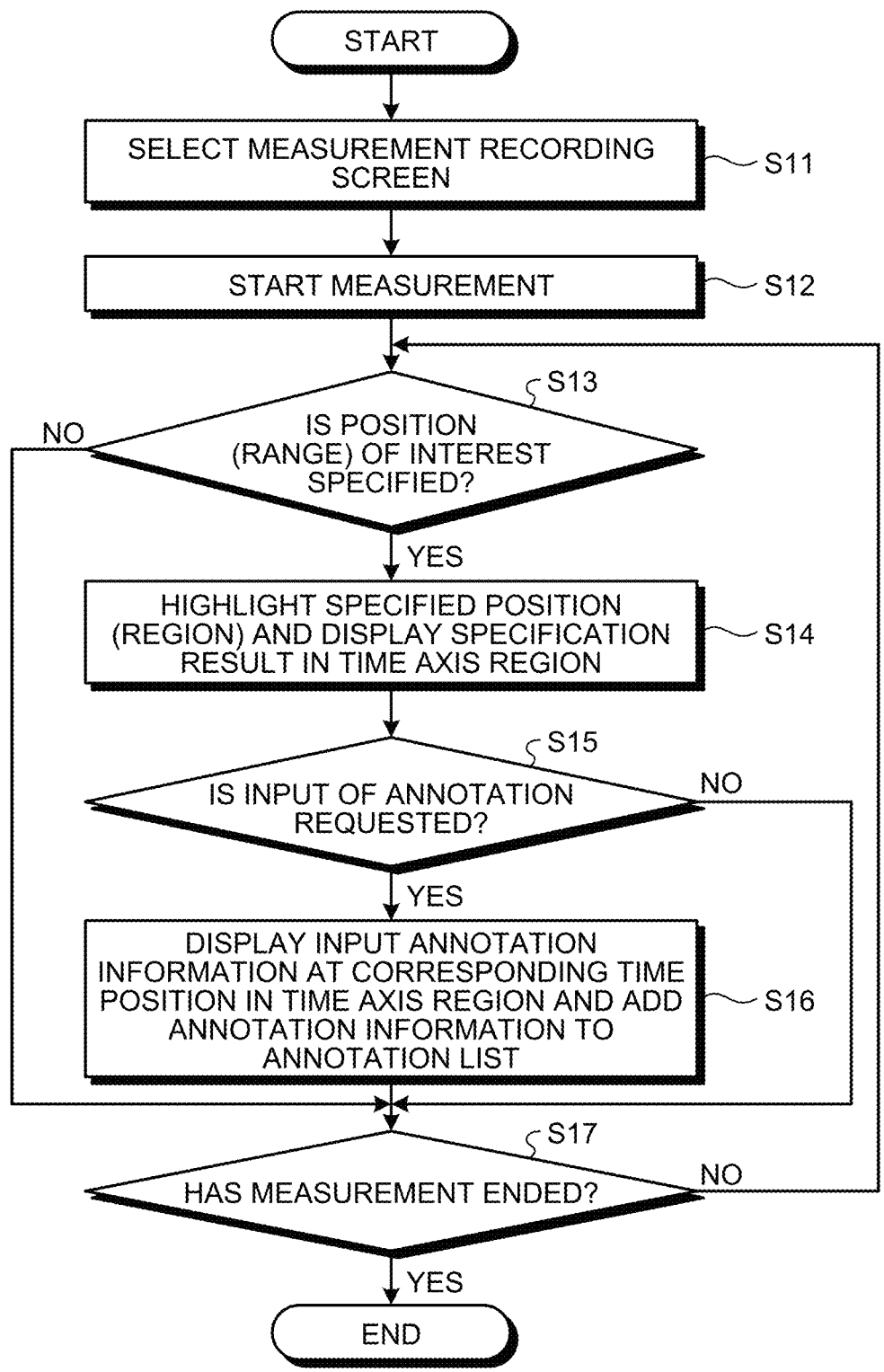
FIG. 8 is a flowchart of the operations performed by the information processing apparatus in measurement recording.

FIG. 8 is a flowchart of information display processing in the measurement recording stage performed by the information processing apparatus 50. If "measurement recording" is selected on the start screen 204 illustrated in FIG. 2 (Step S11), measurement is started and a plurality of signal waveforms are displayed in synchronization on the same time axis (Step S12). The "signal waveforms" include signal waveforms detected by both a plurality of the same kind of sensors and signal waveforms detected by a plurality of different kinds of sensors. While the waveforms of a plurality of biological signals in this example are composed of the waveforms of the MEG signals acquired from the group of magnetic sensors corresponding to the right part of the head of the person to be measured, the waveforms of the MEG signals acquired from the group of magnetic sensors corresponding to the left part of the head of the person to be measured, and the waveforms of the EEG signals acquired from the electrodes for EEG of the person to be measured, the present embodiment is not limited thereto. The sensors are not limited to the left/right sensor groups and may be optionally selected from the parts, such as the parietal region, the frontal lobe, and the temporal lobe. If the sensors for the parietal region are selected in "MEG Window Control 1" illustrated in FIG. 5 and other figures, for example, the other sensors are selected in "MEG Window Control 2".

The information processing apparatus 50 determines whether a point or a range of interest is specified on the displayed signal waveforms (Step S13). If a point or a range of interest is specified (Yes at Step S13), the information processing apparatus 50 highlights the specified point in the display regions (display regions 101 to 103) for the signal waveforms and displays the specification result at the corresponding time position in the time axis region (display region 110) (Step S14). The specification result includes information indicating that the specification is performed or identification information on the specification. Simultaneously with or before or after displaying the specification result in the time axis region, the information processing apparatus 50 determines whether input of an annotation is requested (Step S15). If input of an annotation is requested (Yes at Step S15), the information processing apparatus 50 displays the input annotation information at the corresponding time position in the time axis region and adds the annotation information to the annotation list (Step S16). Subsequently, the information processing apparatus 50 determines whether it has received a measurement end command (Step S17). If no position (region) of interest is specified (No at Step S13), or if no input of an annotation is requested (No at Step S15), the information processing apparatus 50 performs the processing at Step S17 and determines whether to end the measurement. Until the measurement is ended (Yes at Step S17), the information processing apparatus 50 repeats the processing from Step S13 to Step S16.

With this information display method, the information processing apparatus 50 provides the measurement recording screen having higher visibility of the signal information when collecting the signals from the sensors.

Operations in an Analysis

Figure 9:
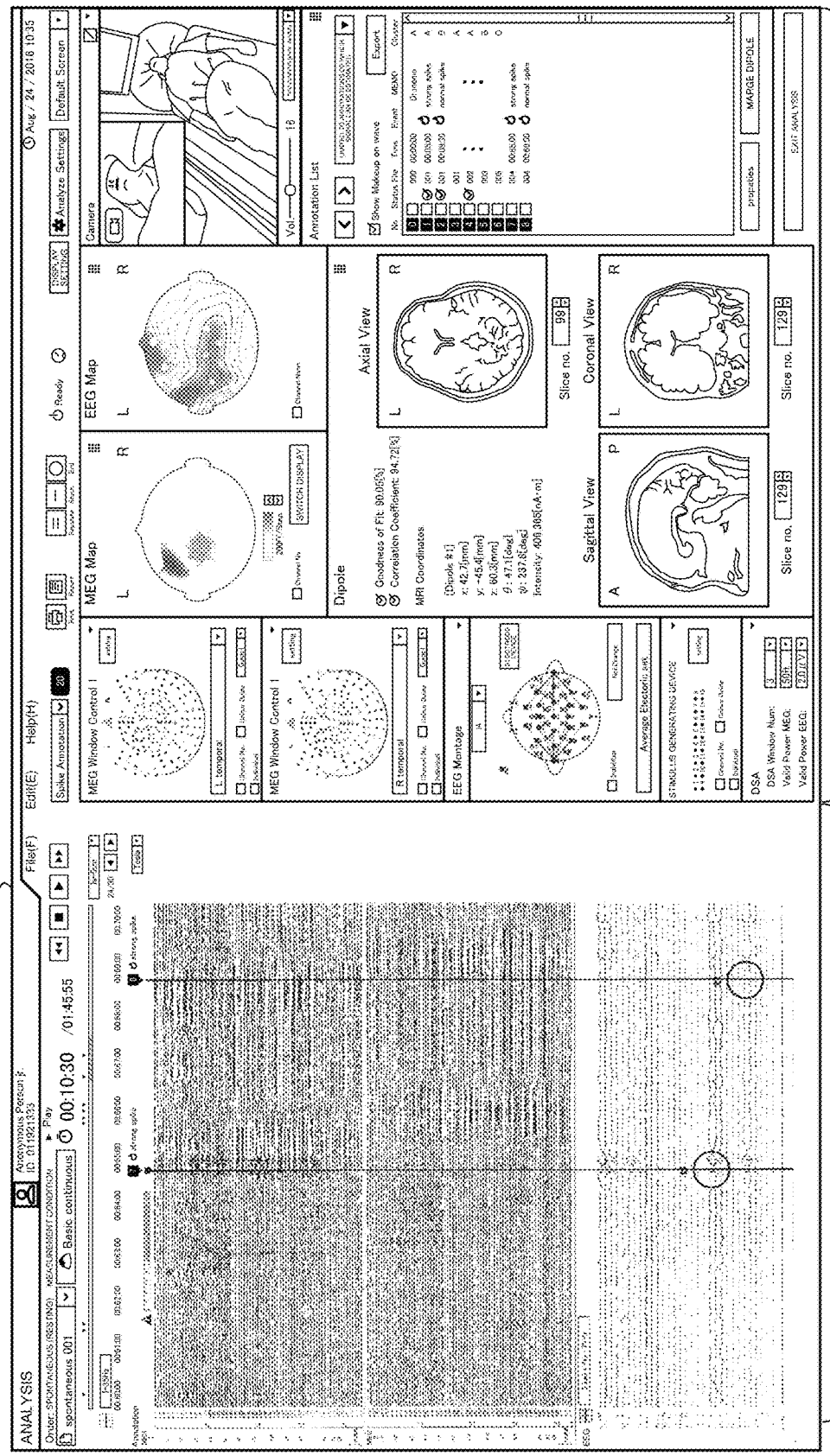
FIG. 9 is a view of an example of an analysis screen.

FIG. 9 is a view of an example of the screen displayed by the information processing apparatus 50 in an analysis. The analysis screen is displayed by selecting the "analysis" button on the start screen 204 illustrated in FIG. 2. The tab 111 on the screen indicates that the screen is the "analysis" screen. The analysis screen associates biological data indicating chronological changes of one or more biological signals of the subject acquired by the measurement with the annotation input to the biological data in the measurement. In this example, the one or more biological signals are the MEG signals acquired from the group of magnetic sensors corresponding to the right part of the head of the person to be measured, the MEG signals acquired from the group of magnetic sensors corresponding to the left part of the head of the person to be measured, and the EEG signals acquired from the electrodes for EEG of the person to be measured. The information processing apparatus 50 according to the present embodiment has a function of performing control to display the analysis screen on the display unit (display device 28, which will be described later). In the example illustrated in FIG. 9, the analysis screen includes a region 202A and a region 202B. The region 202A displays the waveforms (corresponding to the biological data) indicating the chronological changes of the recorded three biological signals with the annotation. The region 202B displays analysis information. The region 202A that displays the recorded signal waveforms and the annotation information is disposed in the left part of the screen viewed from the measurer, and the region 202B that displays the analysis information is disposed in the right part of the screen viewed from the measurer. This layout improves working efficiency in checking or determining the analysis result in the region 202B using the mouse or the like while checking or selecting the signal waveforms in the region 202A in the analysis.

In this example, the waveforms of the MEG signals in the second display regions 101 and 102 are displayed above the waveforms of the EEG signals in the second display region 103 in the region 202A. In the region 202B on the right side of the region 202A, the MEG distribution maps 141 and 142 are displayed in the screen region closer to the region 202A and in the upper part of the screen, and the EEG distribution map 130 is displayed under the MEG distribution maps 141 and 142. Consequently, the analyzer can move the line of sight in order of the "waveforms of the EEG signals" in the second display region 103, the "waveforms of the MEG signals" in the second display regions 101 and 102, the MEG distribution maps 141 and 142, and the EEG distribution map 130 (clockwise in this case). This layout enables the analyzer (or the measurer) to move the line of sight more efficiently, thereby improving working efficiency in the analysis. While the line of sight is moved clockwise in the example described above, the present embodiment is not limited thereto.

Figure 10:
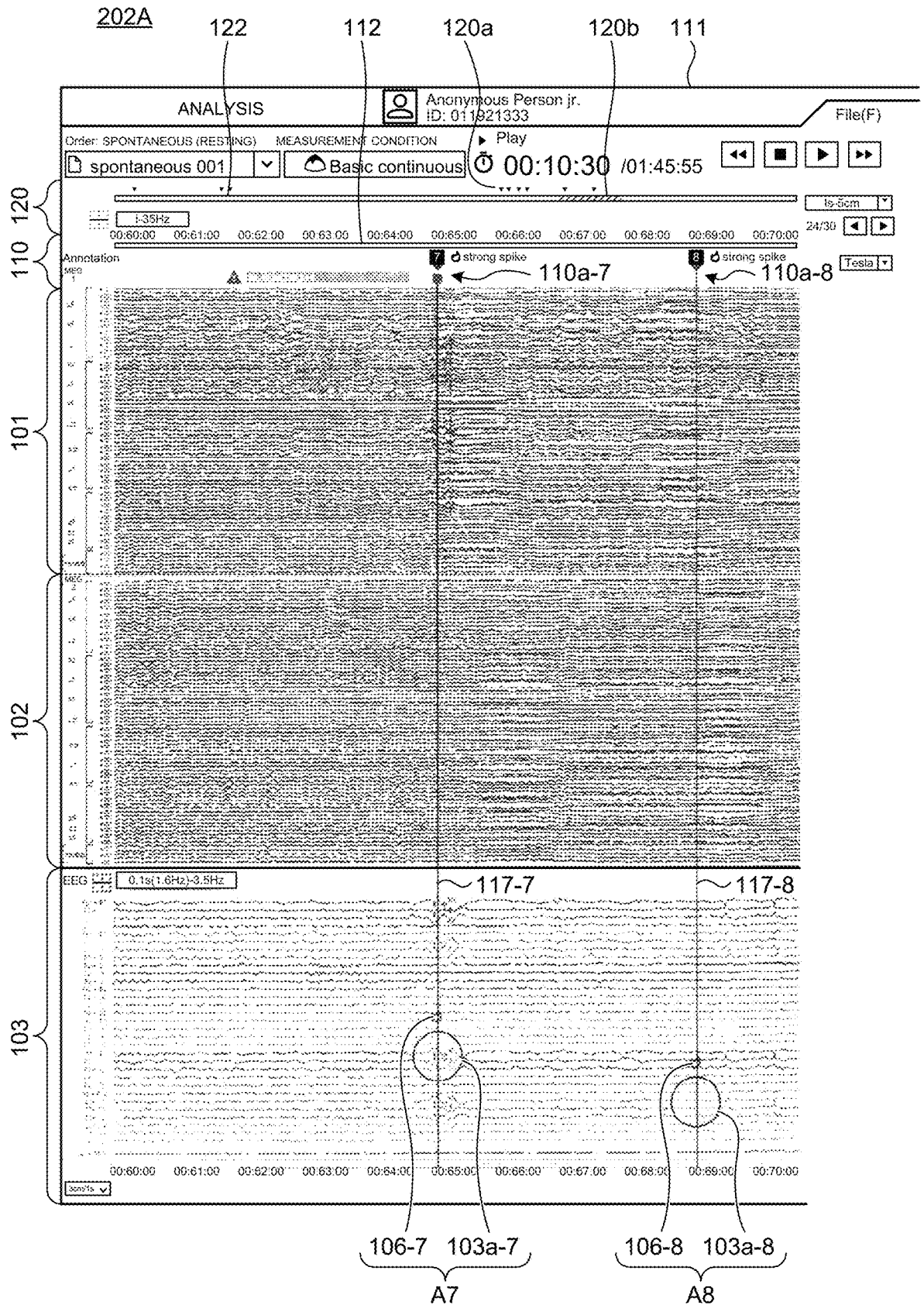
FIG. 10 is an enlarged view of a left region of the analysis screen.

FIG. 10 is an enlarged view of the left region 202A illustrated in FIG. 9. The region 202A includes the display region 110, a display region 120, and the display regions 101 to 103. The display regions 110 and 120 display the time information in the measurement in the horizontal direction (first direction) of the screen. The display regions 101 to 103 display the recorded signal waveforms side by side in the vertical direction (second direction) of the screen in units of a type.

The display region 110 displays the time axis 112 and annotations 110a-7 and 110a-8. The time axis 112 indicates the lapse of time in the recording. The annotations 110a-7 and 110a-8 are added along the time axis 112. The display region 120 displays a time axis 122 indicating the entire recording time. Along the time axis 122, pointer marks 120a and a time zone 120b are displayed. The pointer mark 120a indicates the time position at which an annotation is added. The time zone 120b indicates a period of time in which the signal waveforms being displayed in the display regions 101 to 103 are recorded. This display form enables the analyzer to intuitively grasp the stage of the measurement recording in which the signal waveforms being analyzed are acquired.

After opening the analysis screen, the analyzer can display the signal waveforms in a desired period of time in the display regions 101 to 103 by dragging the time zone 120b on the bar of the time axis 122, for example. Alternatively, the analyzer can display the signal waveforms before and after a desired annotation in the display regions 101 to 103 by selecting the annotation from the annotation list 180, which will be described later.

The display regions 101 to 103 display annotations A7 and A8 added to the signal waveforms in the recording. Marks 103a-7 and 103a-8 are highlighted, and attribute icons 106-7 and 106-8 are displayed near the marks 103a-7 and 103a-8, respectively. Furthermore, vertical lines 117-7 and 117-8 indicating the time positions of the marks 103a-7 and 103a-8, respectively, are displayed. If an annotation is added relating to specification of a certain point in the display region 103, for example, displaying the lines 117-7 and 117-8 can facilitate the analyzer's visual recognition of the specification result also in the display regions 102 and 101, which are the display areas for different kinds of signals. The lines 117-7 and 117-8 can be included in the annotation information because they facilitate the analyzer's visual recognition of the annotation information and may be referred to as "annotation lines". By selecting the line 117-7 or 117-8, the signal waveforms in a certain period of time before and after the time are displayed in an enlarged manner. This processing will be described later.

Figure 11:
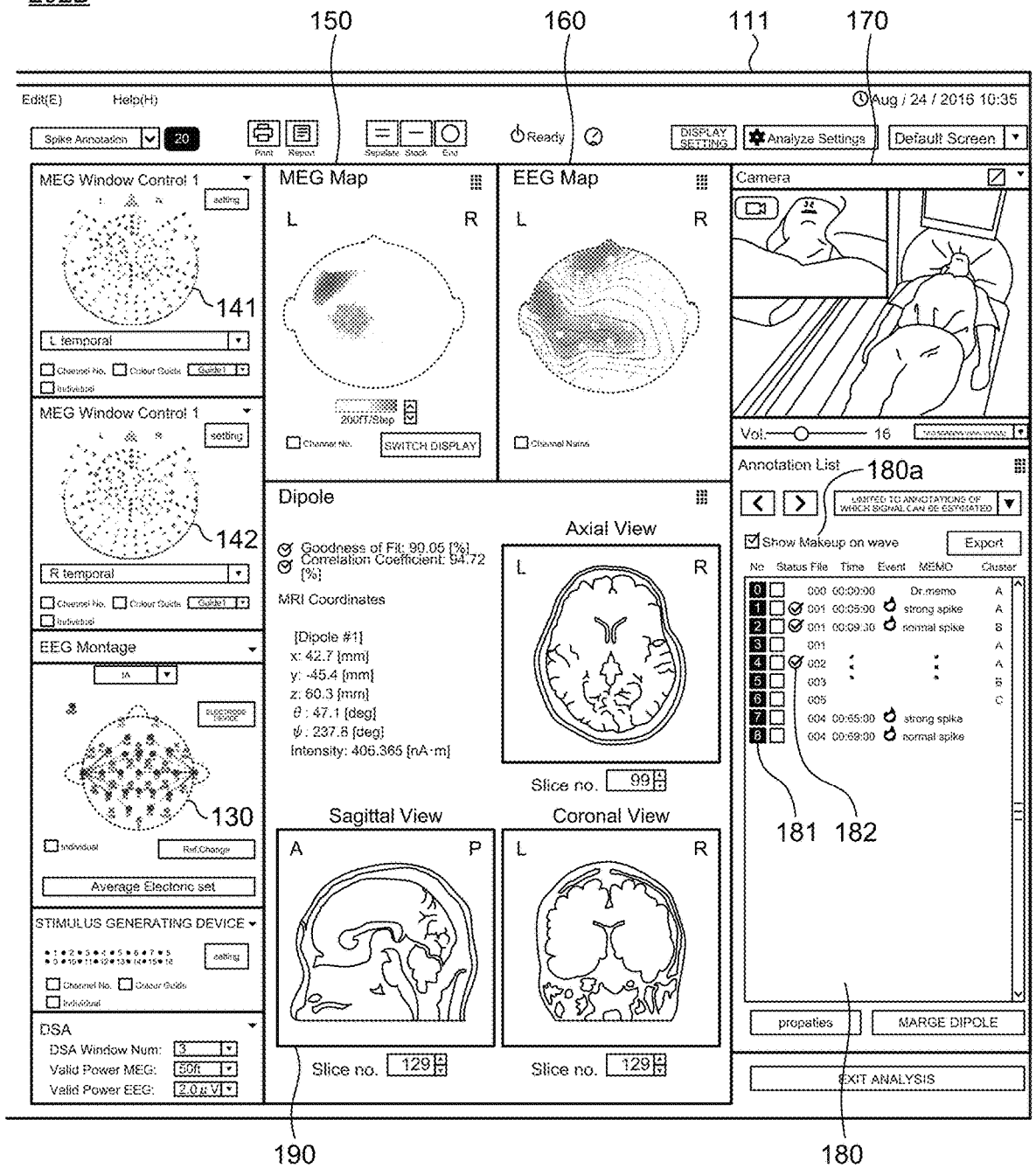
FIG. 11 is an enlarged view of a right region of the analysis screen.

FIG. 11 is an enlarged view of the right region 202B at the same time as FIG. 10. The region 202B displays the MEG distribution maps 141 and 142 and the EEG distribution map 130. The MEG distribution maps 141 and 142 correspond to the signal waveforms displayed in the display regions 101 and 102. The EEG distribution map 130 corresponds to the signal waveforms displayed in the display region 103. The region 202B also displays an isomagnetic field map 150 of the MEG, a map area 160 of the EEG, and a display window 190 for tomographic images of the brain of the person to be measured acquired by magnetic resonance imaging (MRI). The isomagnetic field map 150 displays an emitting area and a sinking area of a magnetic field in a color-coded manner, thereby enabling the analyzer to visually grasp the direction in which an electric current flows. The isomagnetic field map 150 and the map area 160 are information acquired after completion of the measurement. The MRI tomographic images are information acquired by another examination.

The monitor window 170 displays the video of the person to be measured in the measurement in synchronization with the time when the signal waveforms in the display regions 101 to 103 are acquired. The analyzer can analyze the signal waveforms while viewing the monitor window 170 and checking the state of the person to be measured.

In the annotation list 180, all the annotations added in the measurement recording are listed. The annotation list 180 describes the annotation information (e.g., the attribute icon and the text input information) added corresponding to annotation numbers 181. While the annotation list 180 of the analysis screen displays the added annotations in an ascending order (such that old data is displayed at the top), for example, the present embodiment is not limited thereto. Similarly to the measurement recording screen, the annotation numbers are not necessarily used, and the annotations may be identified by a combination of time, file name, attributes, and other elements. Furthermore, the annotations included in the annotation list 180 can be displayed in other orders and sorted by item. By clicking a desired annotation number 181 or a desired row, the analyzer can display the signal waveforms in a predetermined period of time including the time position at which the annotation is added in the display regions 101 to 103 illustrated in FIG. 10.

Unlike the measurement recording screen, the annotation for which the analyzer checks the signal waveforms of the annotation part and finally estimates the signal source is provided with an estimation completion mark 182 (illustrated in FIG. 11).

If non-display is selected in the selection box 180a for selecting display/non-display of the annotations, the attribute icons 106-7 and 106-8 in the display region 103 illustrated in FIG. 10 disappear. Non-display of the highlighted marks 103a-7 and 103a-8 may be selected in the selection box 180a for selecting display/non-display.

Figure 12:
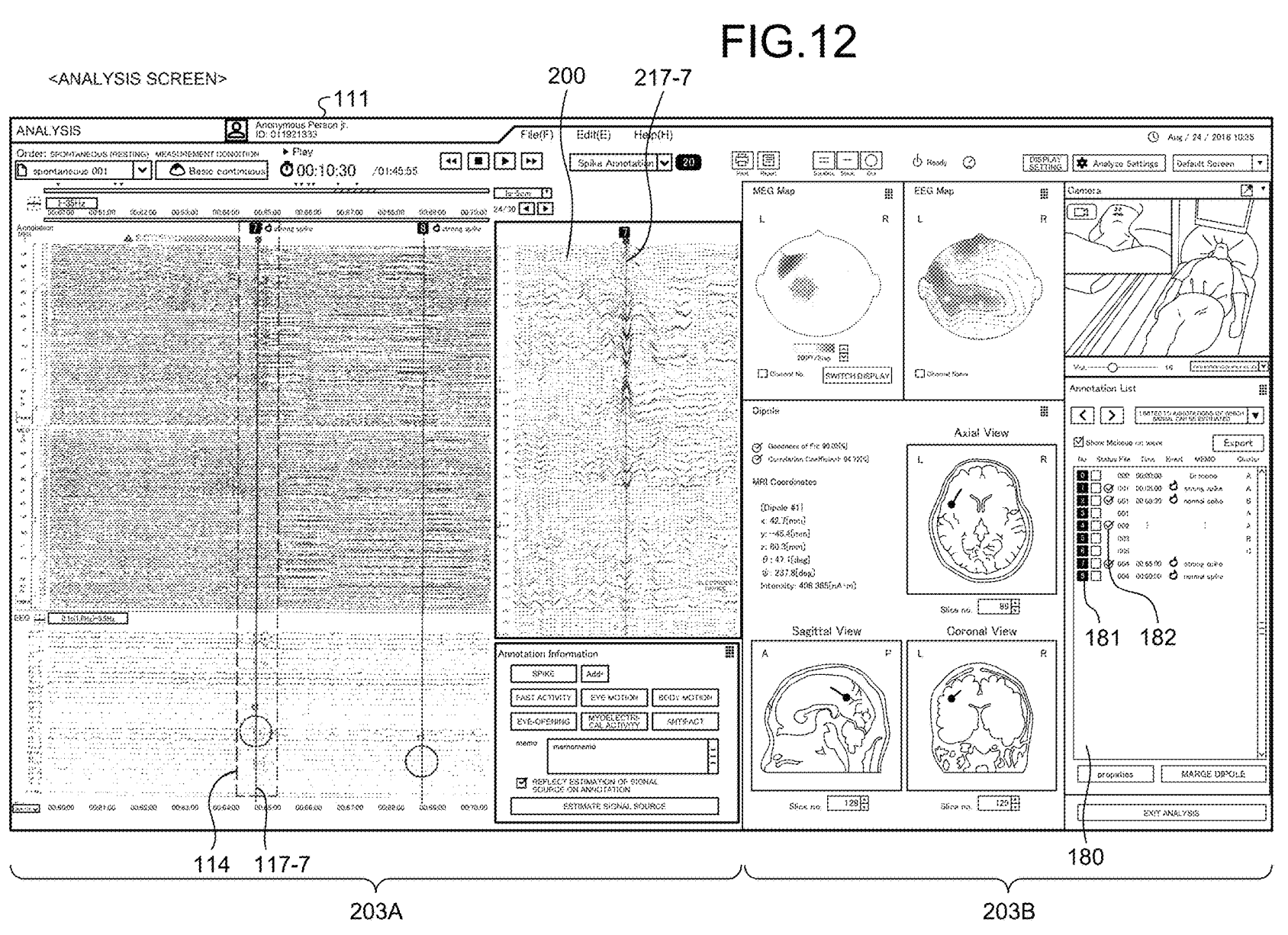

FIG. 12 is an entire view of the screen displayed just after the line 117-7 is selected (by a double click, for example) on the analysis screen illustrated in FIG. 10. If the analyzer focuses on the annotation A7 and selects the line 117-7 (by a double click, for example) to analyze the waveforms in the area, the signal waveforms near the highlighted signal waveforms are displayed in an enlarged manner in an enlarged display region 200. The signal waveforms and a line 217-7 indicating the time position are displayed in an enlarged manner over a predetermined time range indicated by an area 114.

Figure 13:
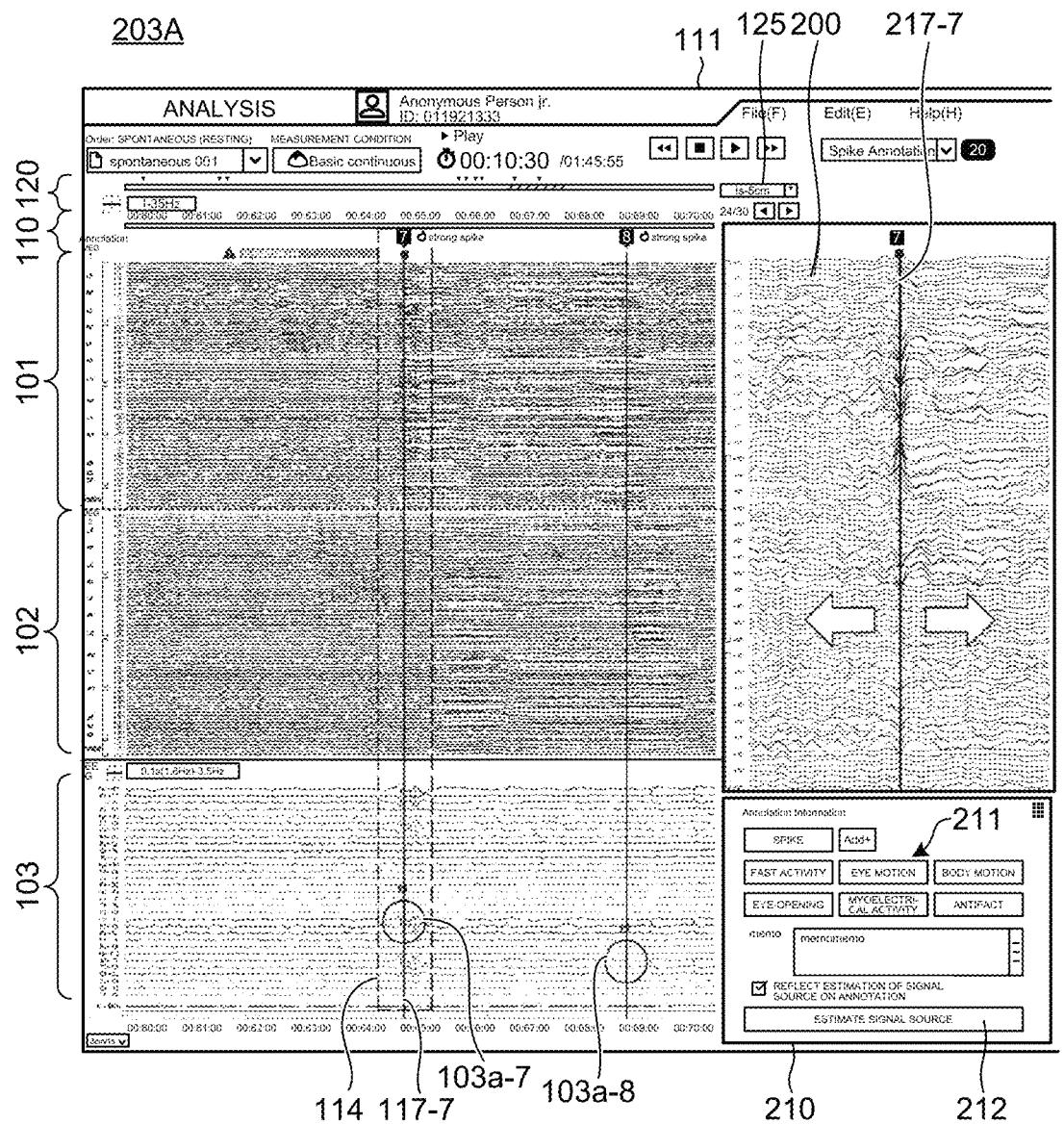
FIG. 13 is an enlarged view of a left region of the screen illustrated in FIG. 12.

FIG. 13 is an enlarged view of a left region 203A (display region for the signal waveforms) illustrated in FIG. 12. By enlarging and displaying the signal waveforms in the enlarged display region 200, the analyzer can recheck the validity of the marks added in the recording or check the waveform part not checked in the measurement recording. By dragging the line 217-7 to the left and the right, for example, the analyzer can identify or change the exact point of the waveforms to be issued. The mark 103a highlighted in the display region 103 and/or the attribute icon 106 may be reflected on the enlarged display region 200. To display the highlighted mark 103a and/or the attribute icon 106 in the enlarged display region 200, display or non-display is preferably selectable because they may possibly be an obstacle to visual recognition in accurately determining a singular point in amplitude.

The type of the signal waveforms to be displayed in the enlarged display region 200 and the channel range can be specified. The analyzer, for example, moves the line of sight from the mark 103a-7 highlighted in the display region 103 to the upper part of the screen to check whether a singular point in amplitude is present in the waveforms displayed in the display region 101 or 102 for the MEG waveforms. By inputting the target channel area in the display region 101 or 102 to a box 125, the analyzer can enlarge and display the MEG waveforms relating to the mark 103a-7 in the enlarged display region 200.

A confirmation window 210 is displayed under the screen of the enlarged display region 200. The confirmation window 210 includes signal waveform attribute buttons 211 and a signal source estimation button 212. The attribute buttons 211 correspond to the attribute information included in the popup window 115 on the measurement recording screen. If the attribute added in the recording is wrong, the analyzer can select the attribute button 211 to select the correct attribute. If selection of the correct position and/or attribute of the signal waveforms is confirmed, the analyzer can reflect estimation of the signal source on the annotation by clicking the estimation button 212. In other words, the information processing apparatus 50 according to the present embodiment has a function of estimating the signal source corresponding to the annotation selected from the analysis screen. The estimated signal source is displayed in a manner superimposed on a tomographic image corresponding to the estimated signal source out of a plurality of MRI tomographic images, which will be described later.

Figure 14:
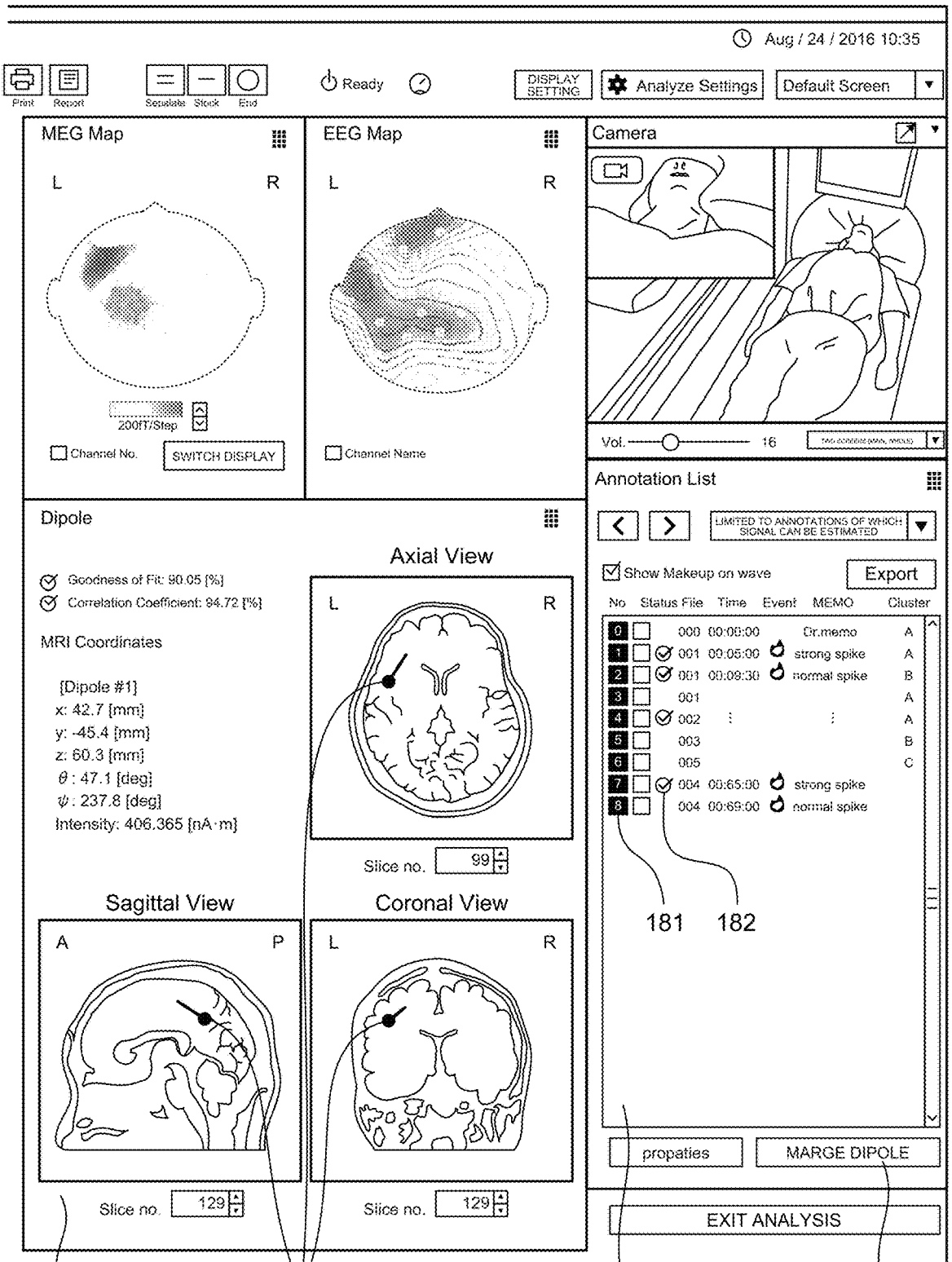
FIG. 14 is an enlarged view of a right region of the screen illustrated in FIG. 12.

FIG. 14 is an enlarged view of the right region 203B illustrated in FIG. 12. If the analyzer confirms the signal waveform position and/or the attribute of a desired annotation and selects the signal source estimation button 212 in FIG. 13, the estimation completion mark 182 is added to the corresponding annotation (annotation number "7" in this example) in the annotation list 180. In addition, dipole estimation results 190a are displayed on the MRI tomographic images in the display window 190.

When the analyzer changes the mark position highlighted in the display regions 101 to 103 and/or the contents of the annotation, the annotation list 180 is updated by the following two methods: a method of reflecting only the latest update information updated by the analyzer on the annotation list 180 and a method of adding new annotation information while maintaining annotation information recorded in the measurement recording. If the latter method is employed, a branch number from the annotation number in the recording, for example, may be allocated as the annotation identification information. In this case, the new annotation information may also be added to the display region 110 and displayed in a different color along the time axis.

Figure 15:
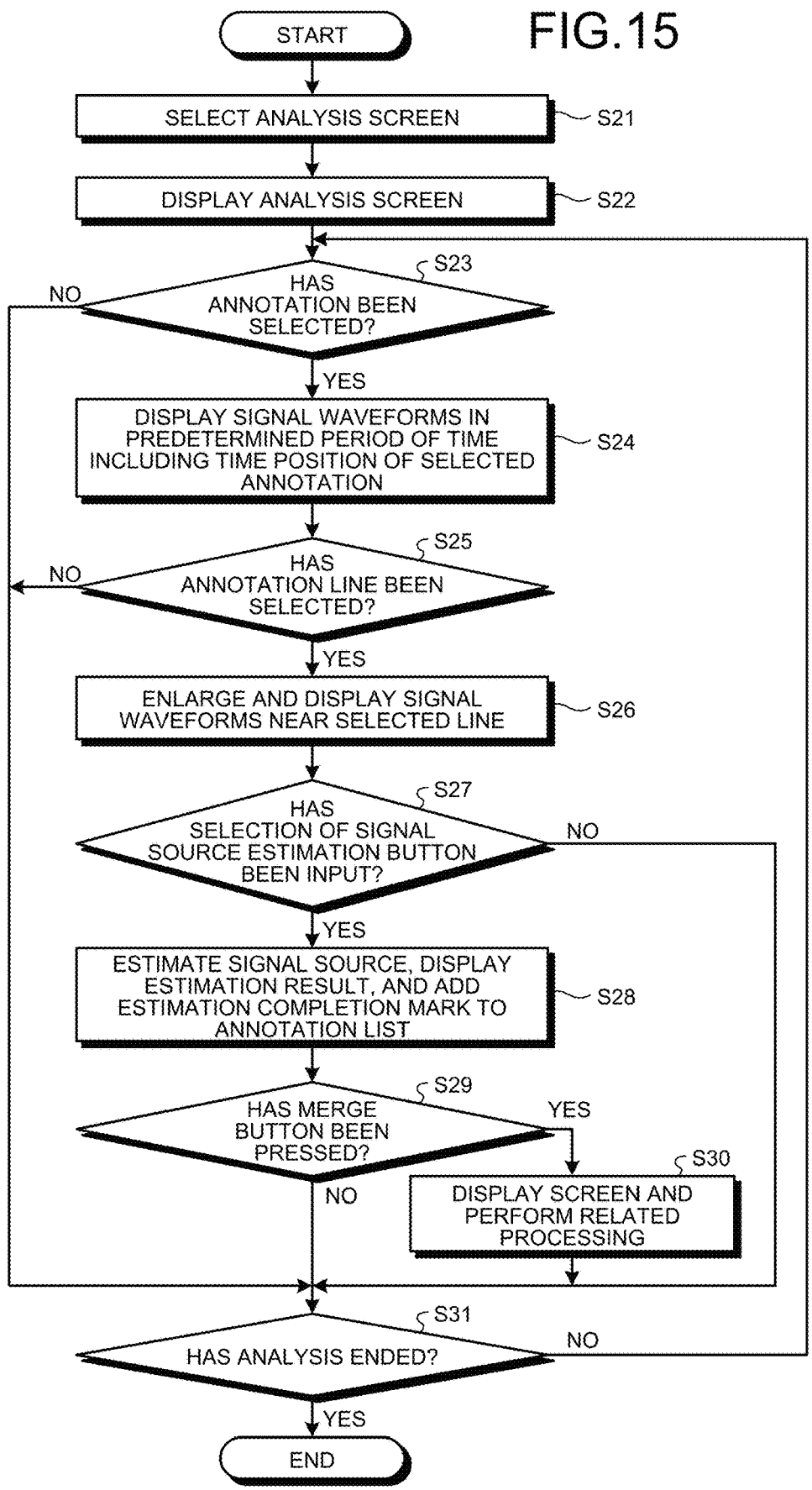
FIG. 15 is a flowchart of the operations performed by the information processing apparatus in an analysis.

FIG. 15 is a flowchart of information display processing in the analysis stage performed by the information processing apparatus 50. If "analysis" is selected on the start screen 204 (refer to FIG. 2) (Step S21), an analysis is started, and the analysis screen is displayed (Step S22). The initial analysis screen may be a blank screen that displays no signal waveform or may display the signal waveforms in a certain time range at the start or the end of the recording. If the analysis screen is displayed, the information processing apparatus 50 determines whether a specific annotation has been selected (Step S23). The annotation may be selected by selecting a specific annotation number or a row in the annotation list 180 or specifying a time position by operating the time zone 120b on the time axis 122 in the display region 120. If an annotation has been selected (Yes at Step S23), the information processing apparatus 50 displays the signal waveforms in a predetermined period of time including the time position of the selected annotation (Step S24).

On the displayed screen, the information processing apparatus 50 determines whether the line 117 indicating the time position of the highlighted mark has been selected (Step S25). If the line 117 has been selected (Yes at Step S25), the information processing apparatus 50 enlarges and displays the signal waveforms in a certain time range including the selected line (Step S26). The target to be displayed in an enlarged manner is not necessarily the signal waveforms near the highlighted mark and may be different kinds of signal waveforms at the same time position. If the highlighted mark is attached to the EEG signal waveforms, the information processing apparatus 50 may enlarge and display the MEG signal waveforms at the same time position. Instead of enlarging and displaying the signal waveforms of all the channels, the information processing apparatus 50 may enlarge and display the signal waveforms acquired from a certain range of channels including the channel from which the marked signal waveforms are acquired. In this case, the information processing apparatus 50 may determine whether specification of the type of the signal waveforms and/or the channel range to be displayed in an enlarged manner is input.

Subsequently, the information processing apparatus 50 determines whether the signal source estimation button 212 is pressed (Step S27). If the signal source estimation button 212 is pressed (Yes at Step S27), the information processing apparatus 50 performs an arithmetic operation for estimating the signal source. The information processing apparatus 50 displays the estimation result on the MRI tomographic screen and adds the estimation completion mark 182 to the annotation list 180 (Step S28). If the information processing apparatus 50 receives pressing of a merge button 300 disposed under the annotation list 180 (Yes at Step S29), the information processing apparatus 50 displays a screen 400, which will be described later, and performs processing relating to the screen 400 (Step S30). The specific contents at Steps S29 and S30 will be described later. If the information processing apparatus 50 does not receive pressing of the merge button 300 (No at Step S29) or after Step S30, the information processing apparatus 50 determines whether an analysis end command is input (Step S31). If no annotation is selected (No at Step S23), if no annotation line for enlarged display is selected (No at Step S25), or if the signal source estimation button 212 is not pressed (No at Step S27), the information processing apparatus 50 performs the processing at Step S31 to determine whether to end the analysis. Until the analysis end command is input (Yes at Step S31), the information processing apparatus 50 repeats the processing from Step S23 to Step S30.

The information processing apparatus 50 may determine whether the annotation is changed between Steps S26 and S27. If the annotation is changed, the information processing apparatus 50 reflects the change on the annotation list 180 and makes the determination at Step S27.

By performing the display operation described above, the information processing apparatus 50 can display the information with higher visibility and operability.

Figure 16:
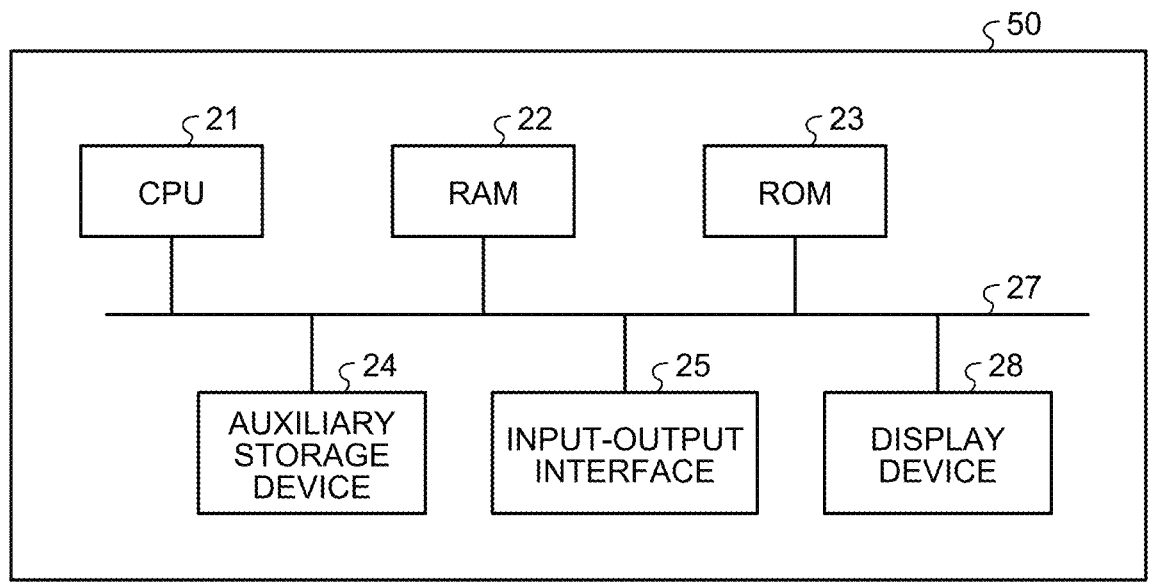
FIG. 16 is a diagram of a hardware configuration of the information processing apparatus.

FIG. 16 is a diagram of a hardware configuration of the information processing apparatus 50. The information processing apparatus 50 includes a central processing unit (CPU) 21, a random access memory (RAM) 22, a read only memory (ROM) 23, an auxiliary storage device 24, an input-output interface 25, and a display device 28. These components are connected to one another via a bus 27.

The CPU 21 controls the entire operations of the information processing apparatus 50 and performs various kinds of information processing. The CPU 21 executes an information display program stored in the ROM 23 or the auxiliary storage device 24 and controls the display operations on the measurement recording screen and the analysis screen. The RAM 22 is used as a work area for the CPU 21 and may include a non-volatile RAM that stores therein main control parameters and information. The ROM 23 stores therein a basic input-output program and other data. The ROM 23 may store therein the information display program according to the present invention. The auxiliary storage device 24 is a storage device, such as a solid state drive (SSD) and a hard disk drive (HDD). The auxiliary storage device 24 stores therein a control program for controlling the operations of the information processing apparatus 50 and various kinds of data and files necessary for the operations of the information processing apparatus 50, for example. The input-output interface 25 includes both a user interface and a communication interface. Examples of the user interface include, but are not limited to, a touch panel, a keyboard, a display screen, an operating button, etc. The communication interface receives the information from various kinds of sensors or the server 40 and outputs the analysis information to other electronic apparatuses. The display device 28 is a monitor display that displays various kinds of information. The display device 28 displays the measurement recording screen and the analysis screen and updates the screen based on an input-output operation performed through the input-output interface 25.

Figure 17:
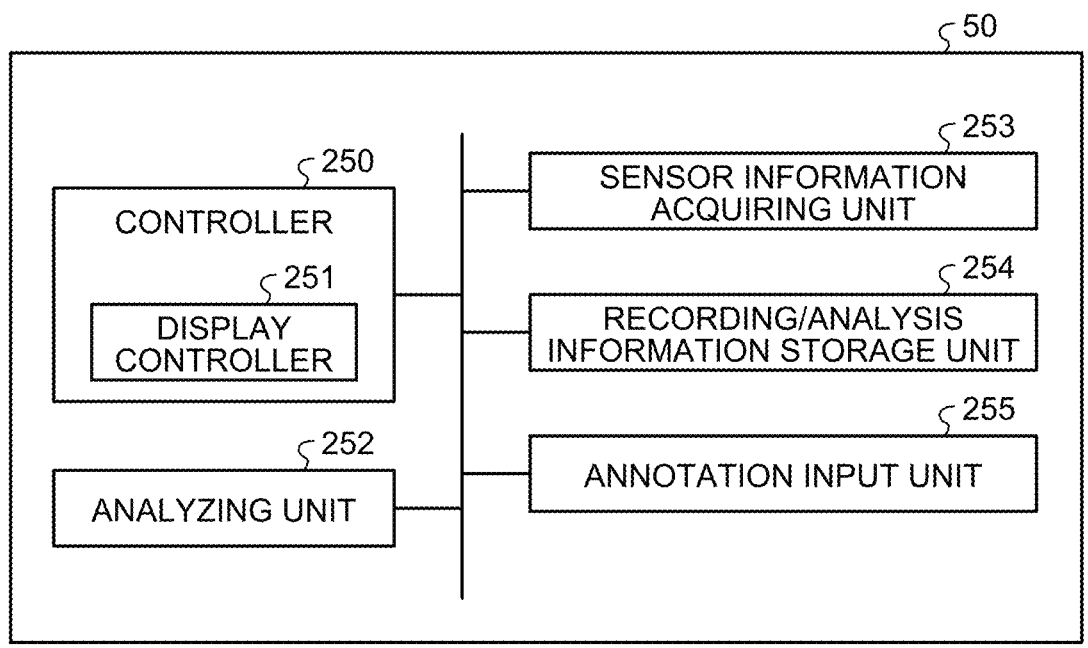
FIG. 17 is a functional block diagram of the information processing apparatus.

FIG. 17 is a functional block diagram of the information processing apparatus 50. The information processing apparatus 50 includes a controller 250, an analyzing unit 252, a sensor information acquiring unit 253, a recording/analysis information storage unit 254, and an annotation input unit 255. The controller 250 includes a display controller 251 that controls screen display on the information processing apparatus 50.

The sensor information acquiring unit 253 acquires the sensor information from the measuring apparatus 3 or the server 40. The annotation input unit 255 receives the annotation information added to the sensor information. The analyzing unit 252 analyzes the collected sensor information. An analysis of the sensor information includes an analysis of the signal waveforms, an analysis of a singular point in amplitude, an analysis of the brain magnetic field including the direction of a current dipole. In other words, the analyzing unit 252 in this example has a function of estimating the signal source corresponding to the annotation selected from the analysis screen (function of an estimating unit). The display controller 251 controls screen display in the measurement recording and the analysis of the sensor information by the method described with reference to FIGS. 2 to 17. The recording/analysis information storage unit 254 stores therein the measurement data and the analysis result. If an annotation is added to the signal waveforms in the measurement recording, the recording/analysis information storage unit 254 stores therein the annotation information in a manner associated with the time information when the signal waveforms are acquired. The functions of the controller 250 including the display controller 251 are implemented by the CPU 21 illustrated in FIG. 16 loading and executing the computer program stored in the ROM 23 or the like on the RAM 22. The functions of the analyzing unit 252 are also implemented by the CPU 21 loading and executing the computer program stored in the ROM 23 or the like on the RAM 22. The present embodiment is not limited thereto, and at least part of the functions of the controller 250 and the analyzing unit 252, for example, may be implemented by a dedicated hardware circuit (e.g., a semiconductor integrated circuit). The functions of the sensor information acquiring unit 253 and the annotation input unit 255 are implemented by the input-output interface 25.

The functions of the recording/analysis information storage unit 254 are implemented by the ROM 23 or the auxiliary storage device 24.

Figure 18:
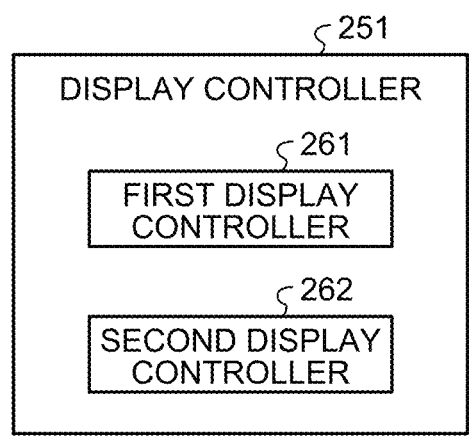
FIG. 18 is a diagram of an example of functions included in a display controller.

FIG. 18 is a diagram of an example of the functions included in the display controller 251. As illustrated in FIG. 18, the display controller 251 includes a first display controller 261 and a second display controller 262. While only the functions relating to the present invention are illustrated in FIG. 18, the functions included in the display controller 251 are not limited thereto. The display controller 251 naturally has the functions described above other than the illustrated ones.

The first display controller 261 performs control for displaying the analysis screen on the display device 28.

If estimation of the signal source is sequentially performed based on the analysis by the analyzing unit 252, and pressing of the merge button 300 disposed under the annotation list 180 is received as described above, the second display controller 262 performs control to display the signal source corresponding to part of the biological data indicating chronological changes of the biological signals in a manner superimposed on a plurality of biological tomographic images sliced in a predetermined direction. In addition, the second display controller 262 performs control to initially display the biological tomographic image with a predetermined signal source superimposed thereon out of the sliced biological tomographic images in a display region. The predetermined signal source is a signal source matching a predetermined condition. While the predetermined condition in this example is the number of signal sources, the present embodiment is not limited thereto. The predetermined signal source according to the present embodiment is the largest number of signal sources of the numbers of signal sources in each of the sliced biological tomographic images. The second display controller 262 initially displays the biological tomographic image having the largest number of signal sources near the center of the display region, which will be specifically described later. The second display controller 262 displays the other biological tomographic images such that they are disposed side by side in order of the layers on the left and right sides from the biological tomographic image disposed near the center. The second display controller 262 may or may not display a biological tomographic image with no signal source superimposed thereon. The following describes the specific contents.

Figure 19:
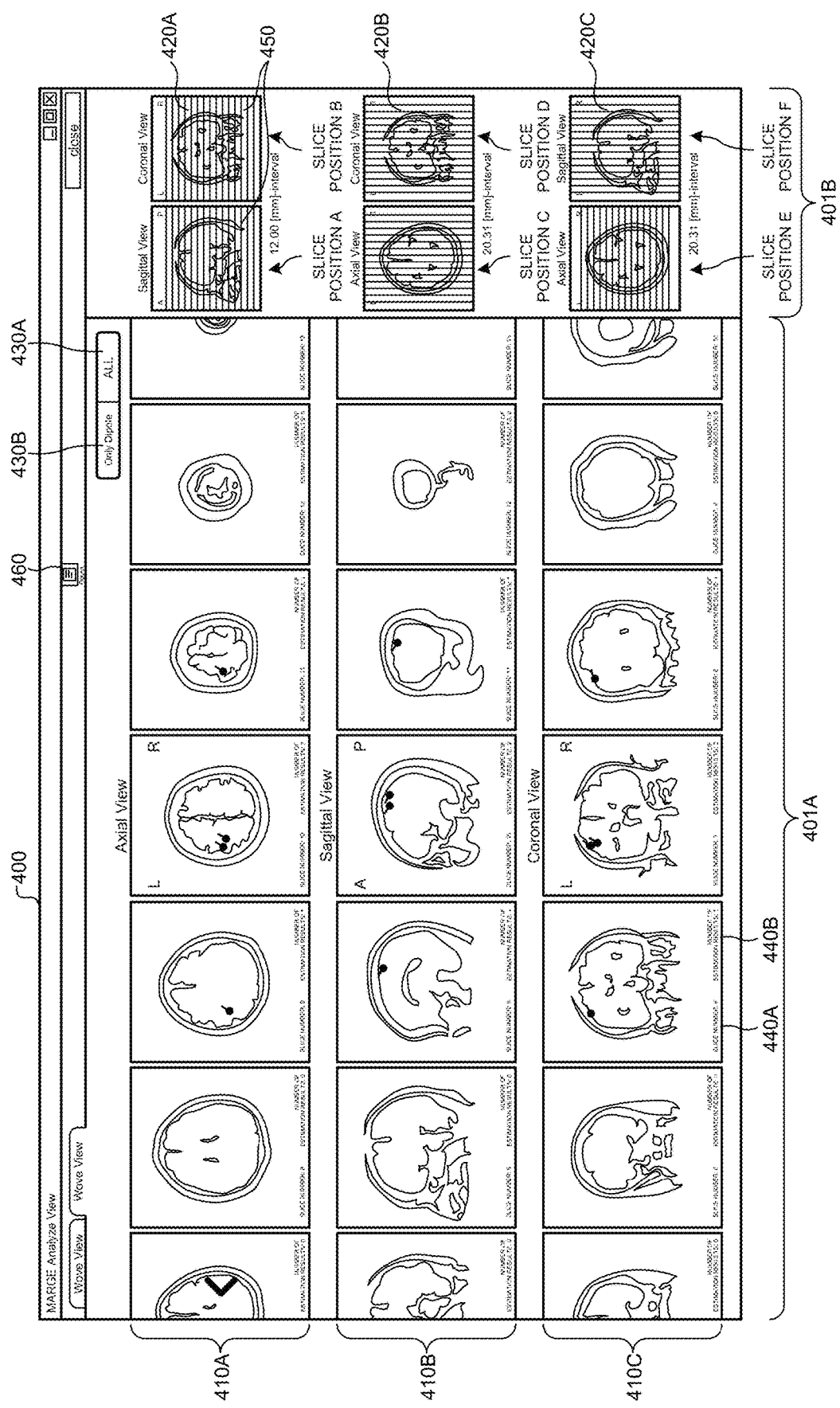
FIG. 19 is a view of a screen displayed when a merge button is pressed according to a first embodiment of the present invention.

If pressing of the merge button 300 disposed under the annotation list 180 illustrated in FIG. 14 is received, the second display controller 262 according to the present embodiment performs control to display a screen 400 illustrated in FIG. 19 on the display device 28. The screen 400 includes a region 401A and a region 401B. The region 401A displays a plurality of biological tomographic images side by side in the lateral direction. The region 401B displays the tomographic positions of the biological tomographic images selected from the region 401A.

The region 401A includes a display region 410A, a display region 410B, and a display region 410C. The display region 410A displays the tomographic images viewed from the top (which may be hereinafter referred to as "slice images A"). The display region 410B displays the tomographic images viewed from the side (which may be hereinafter referred to as "slice images B"). The display region 410C displays the tomographic images viewed from the back (which may be hereinafter referred to as "slice images C"). In the following description, the slice images A, B, and C may be simply referred to as "slice images" when they are not distinguished from one another. The order of the tomographic images in the vertical direction in the region 401A is not limited to the aspect according to the present embodiment.

Figure 20:
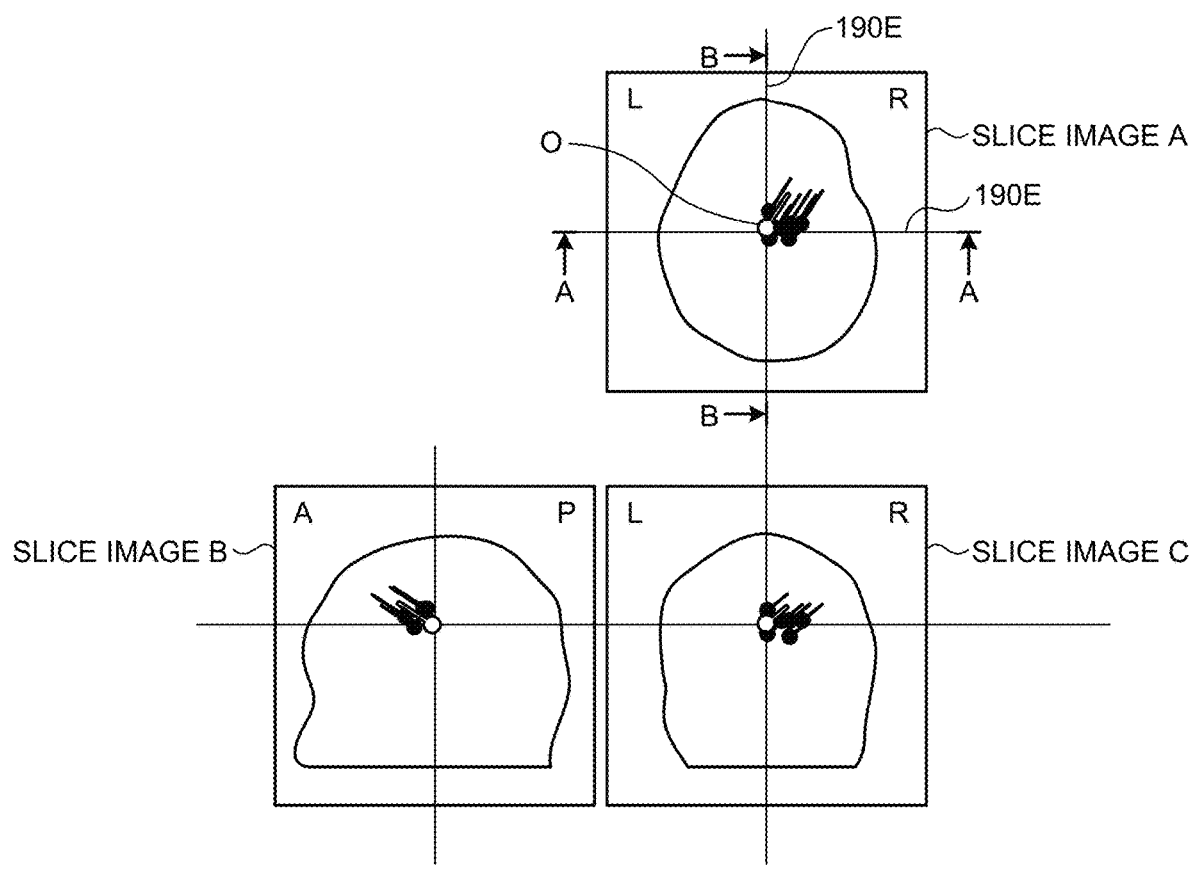
FIG. 20 is a view for explaining the relation among three slice images corresponding to three-dimensional directions.

The following describes the relation among the slice images A, B, and C corresponding to the three-dimensional directions with reference to FIG. 20. In FIG. 20, the positions of the slice images A to C are linked to the three-dimensional directions. Reference lines 190E are displayed across the slice images, and an intersection O of the reference lines 190E indicates the slice position in the slice images. In this example, the slice image C is a sectional view of a section obtained by cutting the slice image A along the reference line 190E in the horizontal direction (lateral direction) viewed in an A direction illustrated in FIG. 20. The slice image B is a sectional view of a section obtained by cutting the slice image A along the reference line 190E in the vertical direction viewed in a B direction illustrated in FIG. 20. In the following description, the point of view corresponding to the slice image A is referred to as "axial view", the point of view corresponding to the slice image B is referred to as "sagittal view", and the point of view corresponding to the slice image C is referred to as "coronal view".

In other words, the biological tomographic images in this example include a first tomographic image (e.g., the slice image A) corresponding to a section in a first direction, a second tomographic image (e.g., the slice image B) corresponding to a section in a second direction orthogonal to the first direction, and a third tomographic image (e.g., the slice image C) corresponding to a section in a third direction orthogonal to the first direction and the second direction.

Referring back to FIG. 19, the second display controller 262 performs control to display information indicating the number of superimposed signal sources with the corresponding biological tomographic image. In the display regions 410A to 410C, the slice images are each displayed with information 440A and information 440B. The information 440A indicates the slice number indicating the position at which the image is sliced. The information 440B indicates the number of signal sources (number of dipole estimation results) superimposed on the slice image.

The region 401B includes a display region 420A corresponding to the display region 410A, a display region 420B corresponding to the display region 410B, and a display region 420C corresponding to the display region 410C.

The display region 420A displays the positions at which the slice images A displayed in the display region 410A are sliced in the tomographic images viewed from the side surface (left image in the display region 420A) and the back surface (right image in the display region 420A). The display region 420A displays tomographic position lines 450 indicating the tomographic positions in a superimposed manner. The adjacent tomographic position lines 450 in a slice position A viewed from the side surface and a slice position B viewed from the back surface are disposed at the same position in the vertical direction in the drawing. The slice numbers corresponding to the respective tomographic position lines 450 are each associated with the corresponding slice image A displayed in the display region 410A. Slice numbers 01 to 15, for example, are allocated from the bottom to the top in the display region 420A.

Similarly, the display region 420B displays the positions at which the slice images B displayed in the display region 410B are sliced at the tomographic positions viewed from the top surface (left image in the display region 420B) and the back surface (right image in the display region 420B). The display region 420B displays the tomographic position lines 450 indicating the tomographic positions in a superimposed manner. The tomographic position lines 450 in a slice position C viewed from the top surface and a slice position D viewed from the back surface are disposed at the same position in the horizontal direction in the drawing. The slice numbers corresponding to the respective tomographic position lines 450 are each associated with the corresponding slice image B displayed in the display region 410B. Slice numbers 01 to 14, for example, are allocated from the left to the right in the display region 420B.

Similarly, the display region 420C displays the positions at which the slice images C displayed in the display region 410C are sliced at the tomographic positions viewed from the top surface (left image in the display region 420C) and the side surface (right image in the display region 420C). The display region 420C displays the tomographic position lines 450 indicating the tomographic positions in a superimposed manner. The tomographic position lines 450 in a slice position E viewed from the top surface from the top to the bottom and the tomographic position lines 450 in a slice position F viewed from the side surface from the left to the right are disposed at the same position. The slice numbers corresponding to the respective tomographic position lines 450 are each associated with the corresponding slice image A displayed in the display region 410C. Slice numbers 01 to 15, for example, are allocated from the top to the bottom (in the top tomographic image on the left side) or from the left to the right (in the side tomographic image on the right side) in the display region 420C.

In other words, the second display controller 262 according to the present embodiment performs control to display the information indicating the tomographic positions of the biological tomographic images displayed in the region 401A (display region). In this example, the second display controller 262 performs control to display the information indicating the tomographic position of the biological tomographic image selected from a plurality of biological tomographic images (slice images). The tomographic position lines 450 and the information 440A indicating the respective slice numbers are stored in a storage device (e.g., the auxiliary storage device 24) in a manner associated with each other.

In this example, the slice images are displayed in the display regions 410A to 410C such that the slice image having the largest number of superimposed dipole estimation results is disposed at the center. The other slice images are disposed side by side in order of the slice numbers (layers) on the left and right sides from the center slice image. In the display region 410A, for example, the slice image with the slice number 10 is disposed at the center, and the slice images with the slice numbers 11, 12, and 13 (only part of it) are disposed in that order on the right side. The slice images with the slice numbers 9, 8, and 7 (only part of it) are disposed in that order on the left side of the slice image with the slice number 10. In the display region 410B, the slice image with the slice number 10 is disposed at the center, and the slice images with the slice numbers 11, 12, and 13 (only part of it) are disposed in that order on the right side. The slice images with the slice numbers 9, 8, and 7 (only part of it) are disposed in that order on the left side of the slice image with the slice number 10. In the display region 410C, the slice image with the slice number 7 is disposed at the center, and the slice images with the slice numbers 8, 9, and 10 (only part of it) are disposed in that order on the right side. The slice images with the slice numbers 6, 5, and 4 (only part of it) are disposed in that order on the left side of the slice image with the slice number 7.

The center is the center in the width direction of the region 401A (corresponding to the "display region"). To facilitate the analyzer's visually finding the slice images having the largest number of dipole estimation results, titles (axial view, sagittal view, and coronal view) may be displayed on the slice image as illustrated in FIG. 19, for example. When the analyzer scrolls the slice images to the left or the right from the initial display state to display the other slice images, these titles may move in conjunction with the scrolling. Movement of the titles in conjunction with the scrolling can facilitate the analyzer's finding the slice images having the largest number of dipole estimation results after the scrolling. To focus on the directions of the tomographic images, the titles are preferably fixed independently of the scrolling.

In the embodiment, the slice image A displayed in the display region 410A, the slice image B displayed just under the slice image A, and the slice image C displayed just under the slice image B do not correspond to the three-dimensional directions. Specifically, in each of the display regions 410A to 410C, the slice image having the largest number of superimposed dipole estimation results 190a out of the slice images displayed in the corresponding display region 410 is disposed at the center. The other slice images are disposed side by side in order of the slice numbers on the left and right sides from the center slice image. This display form enables the analyzer to visually recognize the spread of the dipole estimation results 190a from the center to the left and the right.

The slice images are each displayed with the information 440B indicating the number of dipole estimation results. As a result, the analyzer can check the number of dipole estimation results superimposed on each slice image. In addition, the analyzer can grasp whether a dipole estimation result falls within a predetermined range (e.g., within 1 mm) based on the tomographic position lines 450 in the region 401B and the information 440A indicating the slice number of the selected (desired to be focused on) slice image. If all the slice images fail to be displayed in the region 401, a new slice image can be displayed by scrolling using the mouse and moving the slice images in the horizontal direction, for example. In other words, the second display controller 262 can perform control to display the non-displayed slice images by moving the displayed slice images in the horizontal direction in response to the operation for forwarding/reversing the slice images (operation for scrolling).

Figure 21:
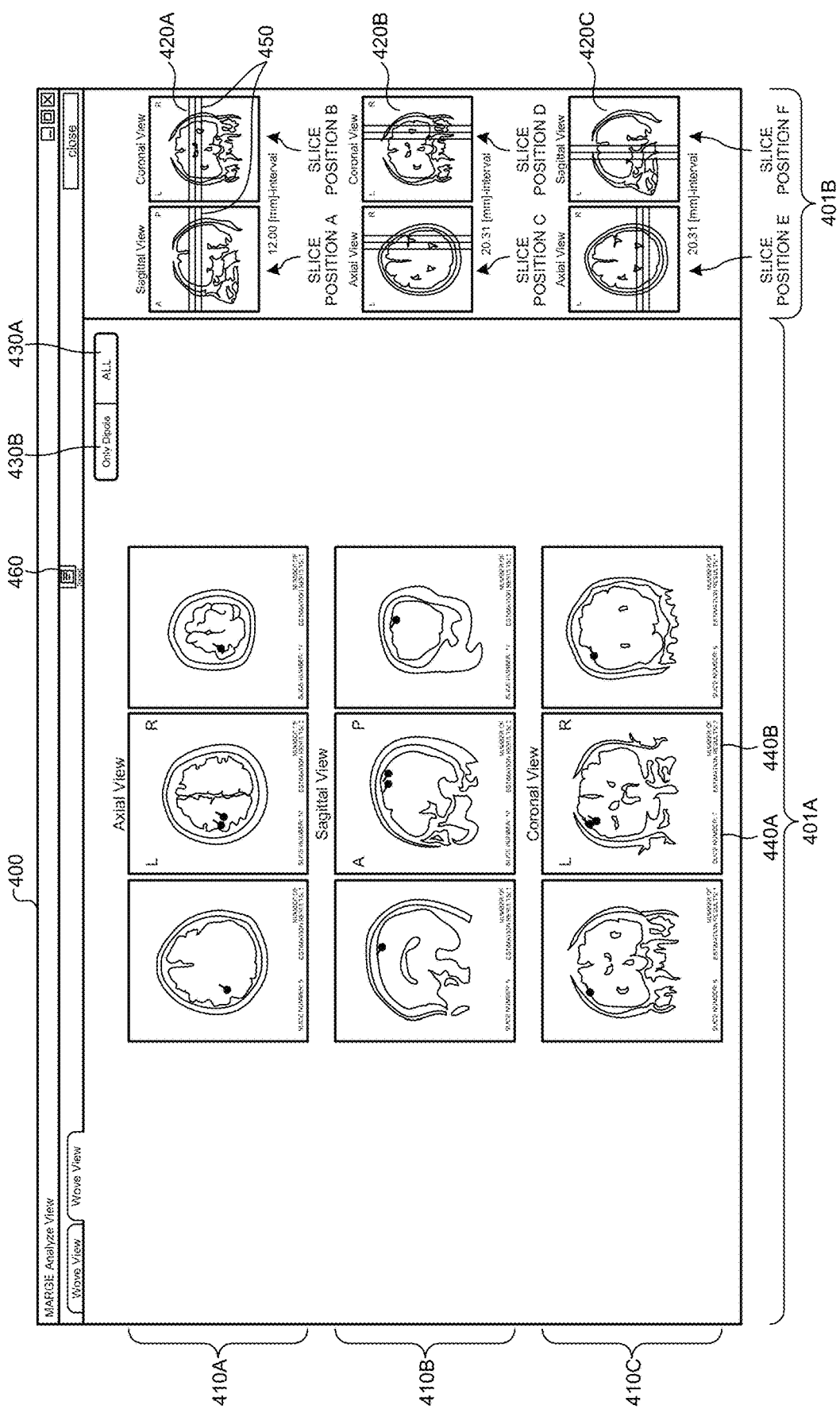
FIG. 21 is a view of an example of the screen displayed when an "Only Dipole" button is pressed.

In this example, an "Only Dipole" button 430B and an "ALL" button 430A are disposed above the display region 410A. The "Only Dipole" button 430B is a button for selecting a mode of displaying only the slice images with the dipole estimation results superimposed thereon. The "ALL" button 430A is a button for selecting a mode of displaying all the slice images including the slice images with no dipole estimation result superimposed thereon. FIG. 19 is a view of the screen 400 displayed when the "ALL" button 430A is pressed. FIG. 21 is a view of an example of the screen 400 displayed when the "Only Dipole" button 430B is pressed. As illustrated in FIG. 21, only the slice images with the dipole estimation results superimposed thereon are displayed in the region 401A, and the tomographic position lines 450 corresponding to the slice images with no dipole estimation result superimposed thereon are not displayed in the region 401B. In other words, only the tomographic position lines 450 corresponding to the slice images with the dipole estimation results superimposed thereon are displayed. As described above, by comparing the slice images to be focused on and the tomographic position lines 450 corresponding thereto on the same screen, the analyzer can readily grasp how far the dipole estimation results are separated from each other.

The analyzer can find out the position at which the largest number of dipole estimation results are present from the slice images with the dipole estimation results superimposed thereon. If the analyzer presses an output button 460, the slice images with the dipole estimation results superimposed thereon are output (the screen 400 at that time is output) and printed out. As described above, the information processing apparatus 50 enables the analyzer to identify the positions of the three-dimensional signal sources (dipole estimation results) more specifically than the conventional technique.

As described above, the present embodiment defines the slice image having the largest number of signal sources as the condition of the slice image initially displayed in the region 401A. The present embodiment initially displays at least the slice image having the largest number of signal sources. As described above, the second display controller 262 initially displays the slice image having the largest number of signal sources near the center of the region 401A. The second display controller 262 displays the other slice images such that they are disposed side by side in order of the layers on the left and right sides from the slice image disposed near the center. This display form enables the analyzer to visually recognize the spread of the signal sources from the center to the left and the right. As a result, the analyzer can identify the target point assumed to be the cause of a case more accurately. In addition, the analyzer can check whether the signal sources are present in the slice images disposed side by side.

The information processing apparatus 50, for example, may superimpose (a group of) signal sources on all the slice images to generate signal-source-superimposed slice images first and then select the signal-source-superimposed slice image having the largest number of signal sources. While the function of selecting the signal-source-superimposed slice image having the largest number of signal sources may be included in the second display controller 262, the present embodiment is not limited thereto. The function may be provided separately from the second display controller 262, for example. In other words, the function (selecting unit) of selecting the biological tomographic image matching a predetermined condition (biological tomographic image initially displayed in the region 401A) may be provided separately from the second display controller 262. The function (selecting unit) may be provided as software (provided by the CPU 21 executing a computer program, for example) or as a dedicated hardware circuit.

The information processing apparatus 50, for example, may identify (a group of) signal sources present on all the slice images and select the slice image having the largest number of signal sources first and then display the signal sources in a manner superimposed on the selected slice image. Alternatively, the information processing apparatus 50, for example, may initially display the slice image selected as described above (slice image having the largest number of signal sources) without superimposing the signal sources thereon and display the information indicating (a group of) signal sources or the number in a superimposed manner at a desired timing. In addition to superimposed display, the information processing apparatus 50 may display the information indicating (a group of) signal sources or the number in a scrollable manner. In this case, a slice image with no signal source superimposed thereon is assumed to be potentially associated with a signal source. Consequently, displaying the slice image is assumed to be an example of an aspect of "initially displaying a biological tomographic image with a predetermined signal source superimposed thereon in a display region".

First Modification of the First Embodiment

Figure 22:
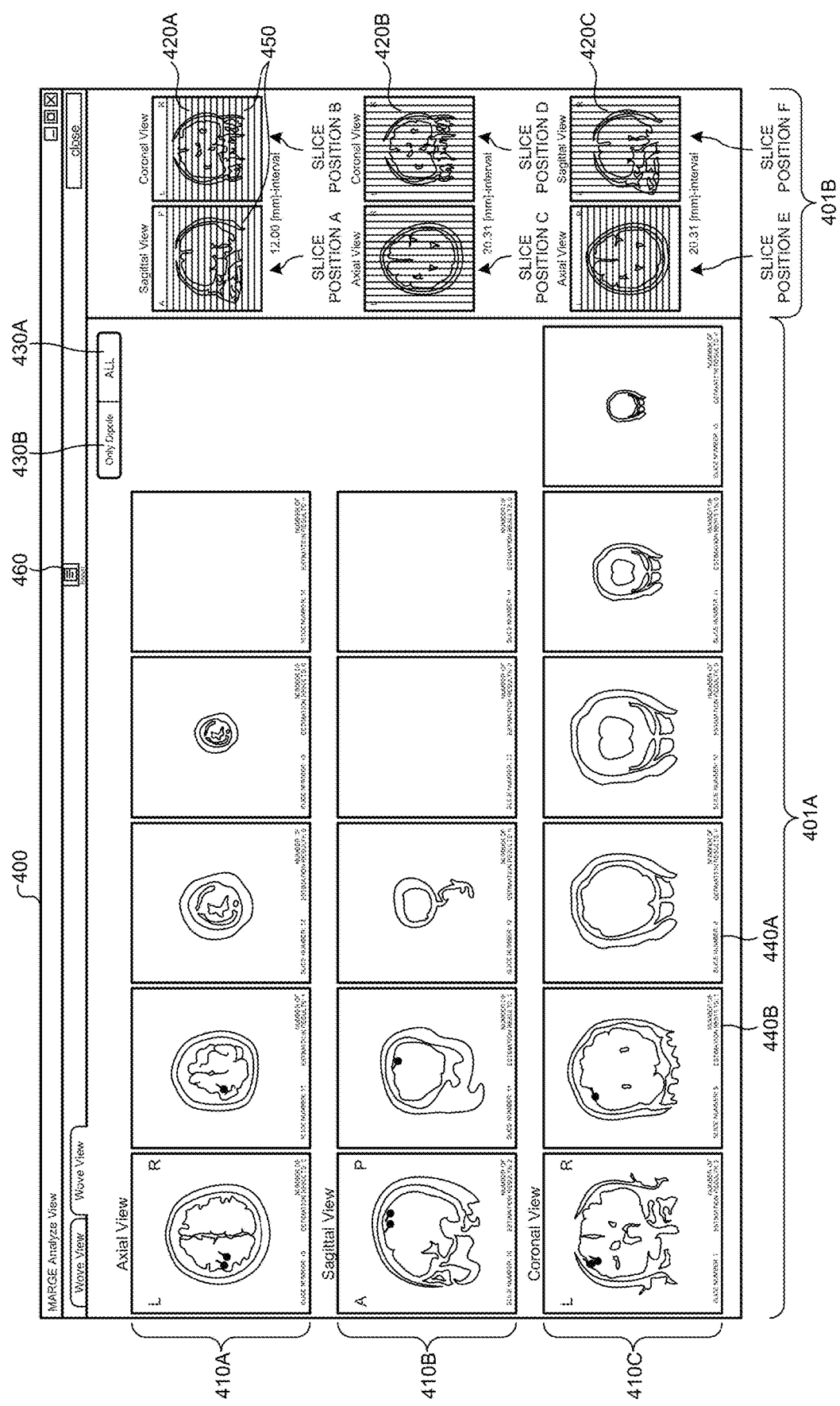
FIG. 22 is a view of the screen displayed when the merge button is pressed according to a modification of the first embodiment.

In the present modification, as illustrated in FIG. 22, the slice image having the largest number of superimposed dipole estimation results is disposed at the left end in each of the display regions 410A to 410C. The other slice images are disposed side by side in order of the slice numbers (layers) on the left and right sides from the slice image disposed at the left end in the same manner as the example illustrated in FIG. 19. If the slice number of the slice image having the largest number of dipole estimation results are the same as those illustrated in FIG. 19, the slice images in the present modification are disposed as illustrated in FIG. 22. In the display region 410A, for example, the slice image with the slice number 10 is disposed at the left end, and the slice images with the slice numbers 11, 12, 13, and 14 are disposed in that order on the right side.

In the display region 410B, the slice image with the slice number 10 is disposed at the left end, and the slice images with the slice numbers 11, 12, 13, and 14 are disposed in that order on the right side. In the display region 410C, the slice image with the slice number 7 is disposed at the left end, and the slice images with the slice numbers 8, 9, 10, 11, and 12 are disposed in that order on the right side.

As described above, the slice image having the largest number of dipole estimation results is disposed at the left end. This layout facilitates the analyzer's finding the slice image having the largest number of dipole estimation results.

Second Modification of the First Embodiment

Figure 23:
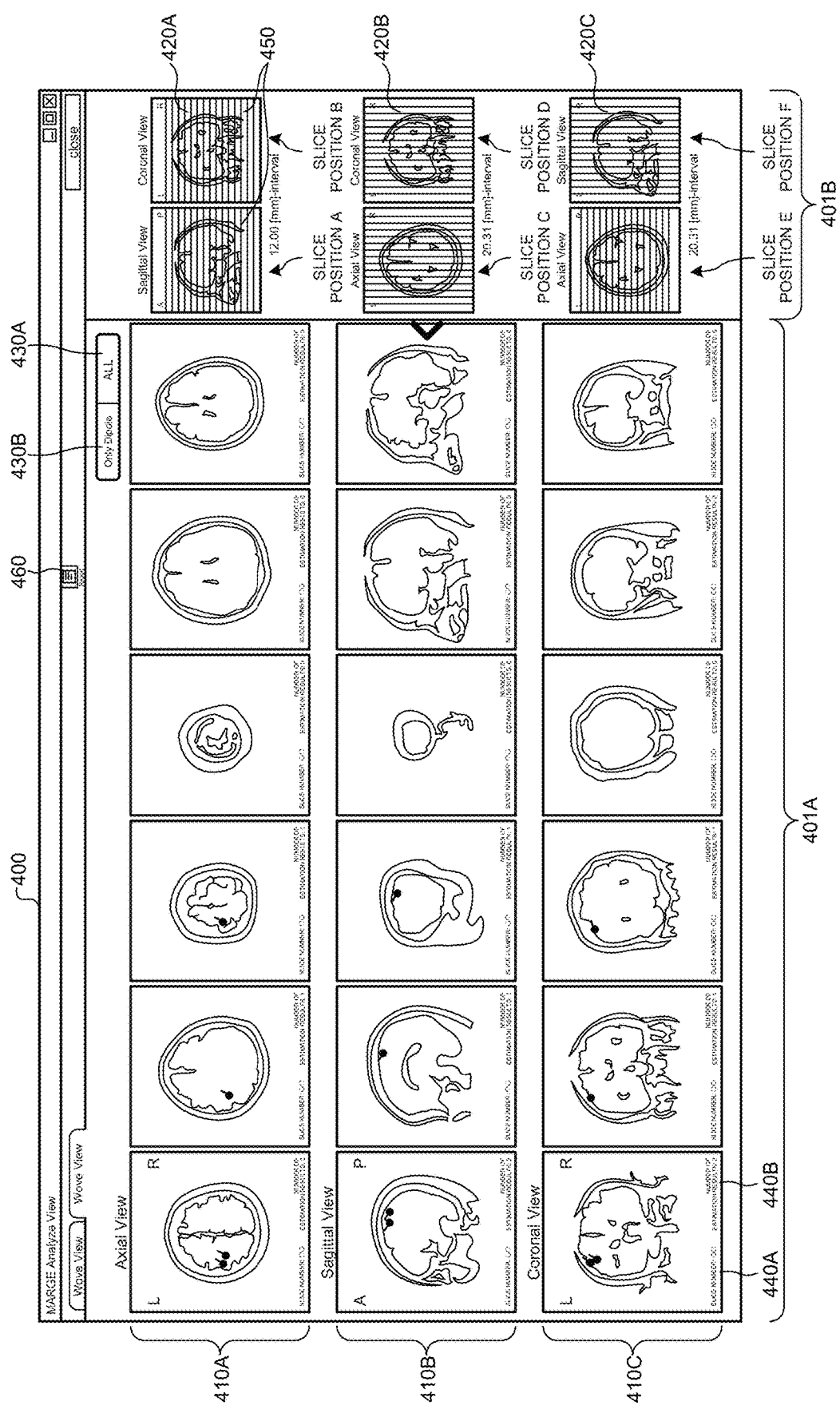
FIG. 23 is a view of the screen displayed when the merge button is pressed according to a modification of the first embodiment.

The condition of the slice images initially displayed in the region 401A, for example, may be the slice images (biological tomographic images) disposed side by side in descending order of the number of signal sources superimposed on the slice images along a predetermined direction. In other words, the second display controller 262 may define the slice image having the largest number of signal sources (biological tomographic image with a predetermined signal source superimposed thereon) as a reference and display the other biological tomographic images side by side in descending order of the number of signal sources along the predetermined direction. As illustrated in FIG. 23, for example, the slice image having the largest number of superimposed signal sources may be disposed at the left end and the other slice images may be displayed such that the number of superimposed signal sources decreases from the left to the right (an example of the predetermined direction). To check only the number of signal sources on the slice images (the number of dipole estimation results), the analyzer simply needs to move the line of sight in one direction from the left to the right in the region 401A. Consequently, the second modification has higher visibility than the layout illustrated in FIG. 19 and other figures. In the same manner as illustrated in FIG. 19, the slice image having the largest number of signal sources may be disposed at the center and the other slice images may be disposed on the left and right sides such that the number of signal sources gradually decreases.

Third Modification of the First Embodiment

Figure 24:
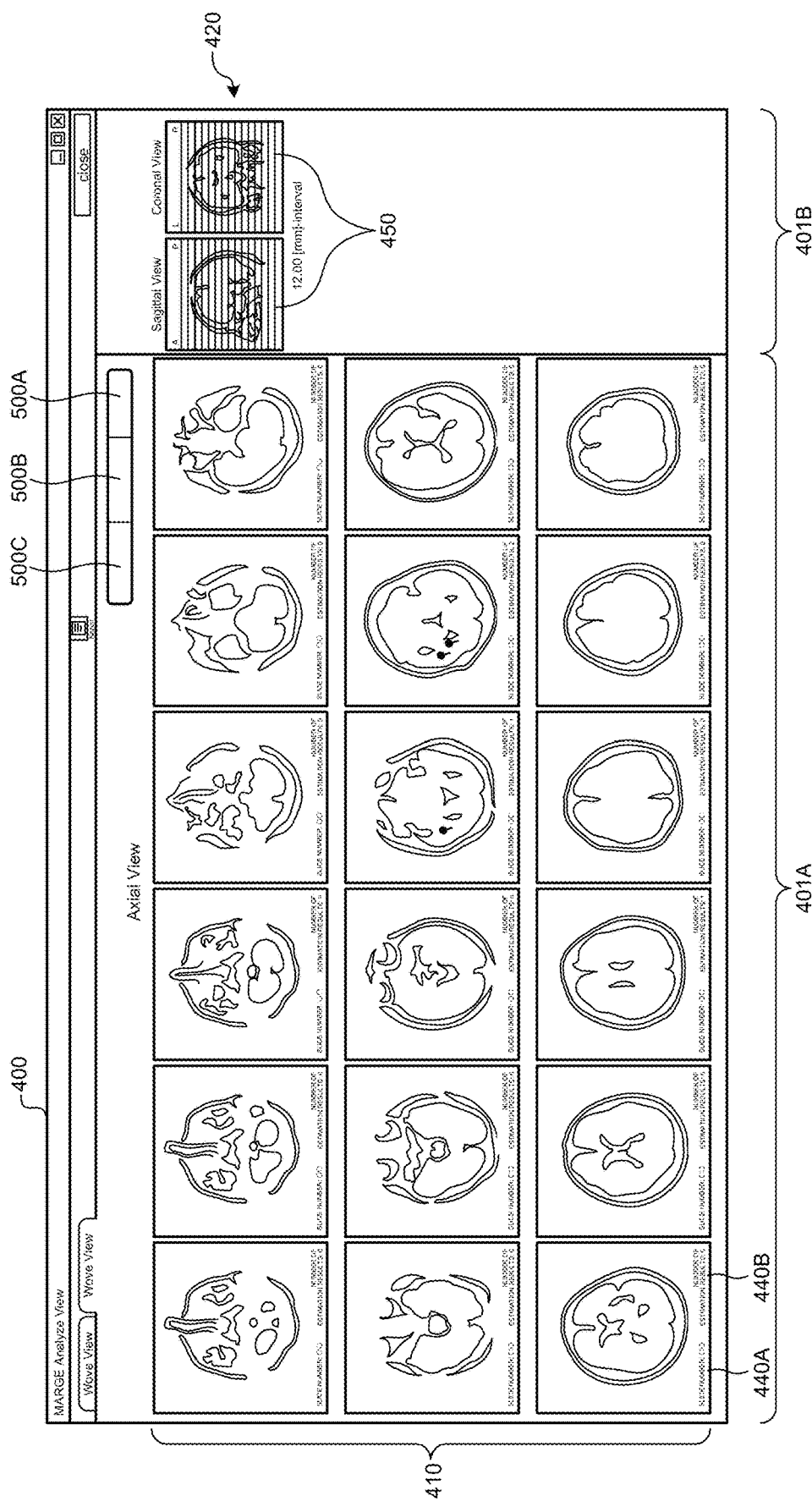
FIG. 24 is a view of the screen displayed when the merge button is pressed according to a modification of the first embodiment.

In the example illustrated in FIG. 19 and other figures, the slice images (slice images A, B, and C) in the three directions are displayed in the regions 410A, 410B, and 410C, respectively. The second display controller 262 according to the present modification displays the slice images in only one direction and does not display the slice images in the other two directions. The condition of the slice images initially displayed in the region 401A may be the conditions according to the first embodiment and the first and second modifications. Displaying the slice images in the region 401A in one row, for example, can increase the visibility of the slice images in one direction. If a number of slice images are present, the tomographic images in one direction may be displayed in a plurality of rows as illustrated in FIG. 24. This layout can reduce the number of times of scrolling and facilitate the analyzer's grasping the overall image, thereby increasing visibility. FIG. 24 illustrates an application example of the second modification of the first embodiment. The second display controller 262 disposes the slice image having the largest number of signal sources at the center and disposes the other slice images on the left and right sides such that the number of signal sources gradually decreases. FIG. 24 illustrates the state obtained by scrolling the screen after the initial display. In the example illustrated in FIG. 24, a button 500A, a button 500B, and a button 500C are disposed above the display region 410 that displays the slice images in only one direction. The button 500A is a button for selecting the direction corresponding to the slice images A (direction of "axial view"). The button 500B is a button for selecting the direction corresponding to the slice images B (direction of "sagittal view"). The button 500C is a button for selecting the direction corresponding to the slice images C (direction of "coronal view"). If pressing of the button 500A is received, the second display controller 262 displays only the group of the slice images A. If pressing of the button 500B is received, the second display controller 262 displays only the group of the slice images B. If pressing of the button 500C is received, the second display controller 262 displays only the group of the slice images C.

Fourth Modification of the First Embodiment

As described above, in the first embodiment, the slice image A displayed in the display region 410A, the slice image B displayed just under the slice image A, and the slice image C displayed just under the slice image B do not correspond to the three-dimensional directions. By contrast, in the present modification, the slice image A displayed in the display region 410A, the slice image B displayed just under the slice image A, and the slice image C displayed just under the slice image B may correspond to the three-dimensional directions. In this case, the second display controller 262 defines any one of the display regions 410A to 410C as a reference. The second display controller 262 displays the slice image having the largest number of superimposed signal sources out of the slice images displayed in the display region 410 serving as the reference at the center. The second display controller 262 displays the other slice images such that they are disposed side by side in order of the layers (slice numbers) on the left and right sides from the center slice image. Subsequently, the second display controller 262 displays the slice images in the other display regions 410 corresponding to the slice images in the reference display region 410. If the display region 410A is defined as a reference, for example, the second display controller 262 displays the slice image having the largest number of superimposed signal sources out of the slice images displayed in the display region 410A at the center. The second display controller 262 displays the other slice images such that they are disposed side by side in order of the layers on the left and right sides from the center slice image. The second display controller 262 then displays the slice images to be displayed in the other display regions 410B and 410C corresponding to the respective slice images displayed in the display region 410A. As described above, by displaying the three slice images corresponding to the three-dimensional directions in a manner aligned in the vertical direction, the analyzer can grasp the positions of the dipole estimation results (signal sources) three-dimensionally. In the same manner as the first modification of the first embodiment, the second display controller 262 may dispose the slice image having the largest number of dipole estimation results out of the slice images displayed in the display region 410 serving as the reference at the left end.

Fifth Modification of the First Embodiment

In the same manner as the fourth modification of the first embodiment, the second display controller 262 according to the present modification displays the slice image having the largest number of superimposed signal sources out of the slice images displayed in the display region 410 serving as the reference at the center. The second display controller 262 displays the other slice images such that the number of signal sources decreases toward the left and the right from the center slice image. Subsequently, the second display controller 262 displays the slice images in the other display regions 410 corresponding to the slice images in the reference display region 410. If the display region 410A is defined as a reference, for example, the second display controller 262 displays the slice image having the largest number of superimposed signal sources out of the slice images displayed in the display region 410A at the center. The second display controller 262 displays the other slice images such that the number of signal sources decreases toward the left and the right from the center slice image. The second display controller 262 then displays the slice images to be displayed in the other display regions 410B and 410C corresponding to the respective slice images displayed in the display region 410A. As described above, by displaying the three slice images corresponding to the three-dimensional directions in a manner aligned in the vertical direction, the analyzer can grasp the positions of the dipole estimation results (signal sources) three-dimensionally. In the same manner as the first modification, the second display controller 262 may dispose the slice image having the largest number of dipole estimation results out of the slice images displayed in the display region 410 serving as the reference at the left end.

Sixth Modification of the First Embodiment

The present modification defines the slice images A, B, and C corresponding to the three-dimensional directions as one group. The second display controller 262 displays the group of the slice images having the largest number of dipole estimation results out of the groups at the center. The second display controller 262 displays the other groups of the slice images such that the number of signal sources decreases toward the left and the right from the center group of the slice images. In the same manner as the first modification of the first embodiment, the second display controller 262 may dispose the group of the slice images having the largest number of dipole estimation results at the left end. As described above, by displaying the group of the three slice images corresponding to the three-dimensional directions in an aligned manner, the analyzer can grasp the positions of the dipole estimation results (signal sources) three-dimensionally.

Seventh Modification of the First Embodiment

The first embodiment switches the display of the slice images using the "Only Dipole" button 430B and the "ALL" button 430A. Without these buttons, for example, the second display controller 262 may display only the slice images with the dipole estimation results superimposed thereon.

Eighth Modification of the First Embodiment

While the slice images displayed in the region 401 are each provided with the information 440A indicating the slice number, the tomographic position line 450 corresponding to the slice image selected in the region 401 may be highlighted (e.g., displayed in a highly visible color, such as red). Furthermore, the method of displaying the information 440A indicating the slice number and the method of highlighting the tomographic position line 450 may be combined.

Ninth Modification of the First Embodiment

Figure 25:
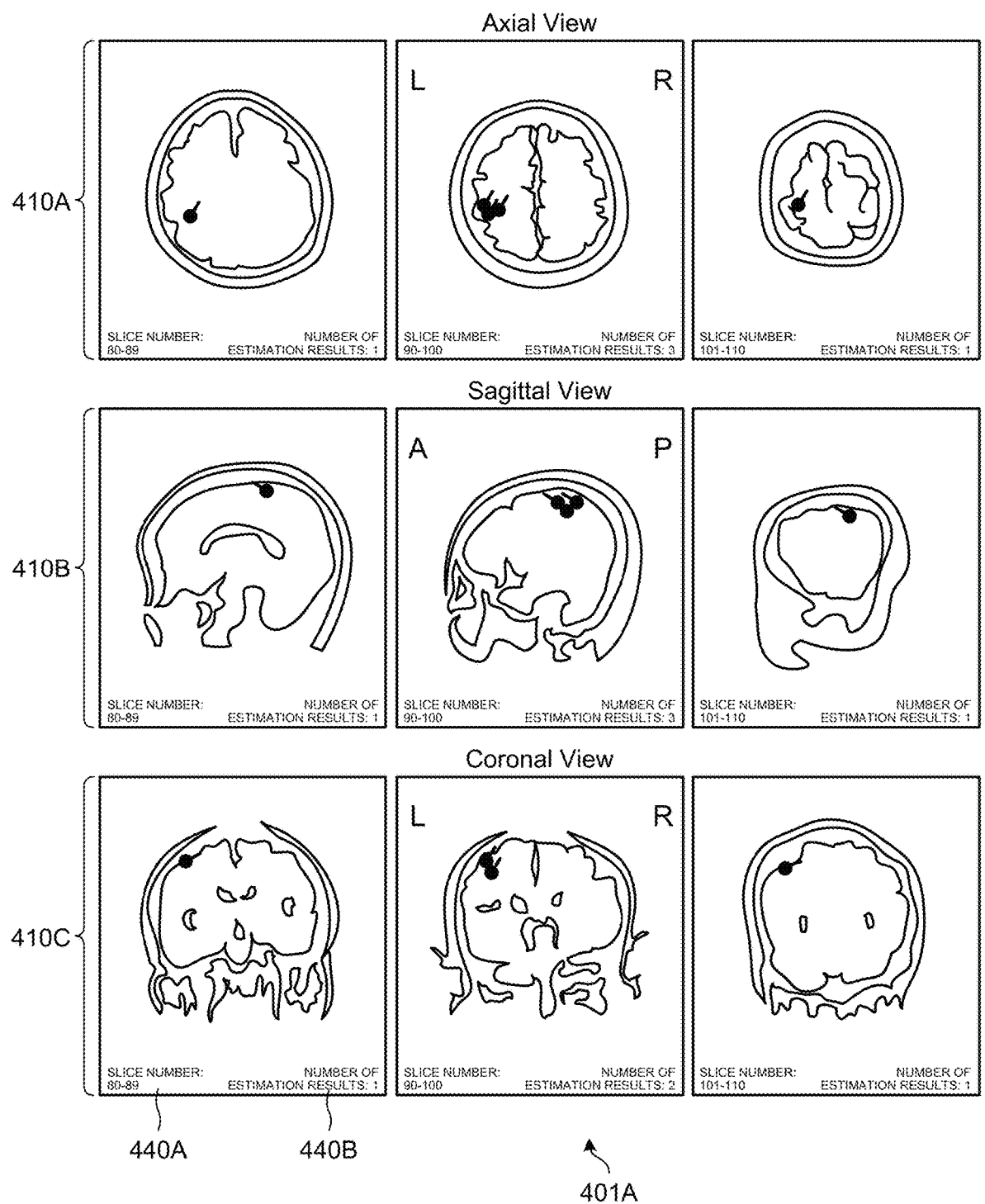
FIG. 25 is a view of the screen displayed when the merge button is pressed according to a modification of the first embodiment.

The embodiment described above and the modifications thereof display the signal source corresponding to one slice image in a manner superimposed on the slice image in the region 401A. The present modification displays the signal sources superimposed on a plurality of slice images in an integrated manner on a predetermined slice image in the region 401. The present modification, for example, combines every ten slice images in order of the slice numbers into one group and calculates the total number of signal sources corresponding to the slice images included in the group. Subsequently, the present modification compares the total numbers of signal sources of the respective groups. As illustrated in FIG. 25, the second display controller 262 displays (any one of) the slice images included in the group having the largest total number at the center in the region 401A. The second display controller 262 displays the slice images included in the other groups such that they are disposed side by side in order of the slice numbers (layers) on the left and right sides from the center slice image.

The slice image displayed in the region 401A is any one of the slice images included in the group. The slice image may be the slice image having the middle number, the smallest number, or the largest number out of the slice images having the consecutive numbers included in the group, for example. On the slice image specified as the image to be displayed, all the signal sources of the slice images included in the group including the slice image are superimposed. If the slice number of the slice image to be displayed is determined, the slice numbers of the slice images displayed on the left and right sides may be the slice numbers shifted by the number of slice images constituting the group. If one group is composed of ten slice images, for example, the slice numbers of the slice image displayed on the left and right sides may be the slice number obtained by adding 10 to or subtracting 10 from the slice number of the slice image displayed at the center.

As illustrated in FIG. 25, the information 440A indicating the slice number displays the range of the slice numbers of the slice images constituting the group. The information 440B indicating the number of signal sources displays the total number of signal sources corresponding to the slice images included in the group including the displayed slice image. While FIG. 25 illustrates an example where only one slice image is displayed at each of the center and the left and right sides in the region 401A, a plurality of slice images may be displayed in the left and right directions. The present modification has a smaller total number of slice images displayed in the region 401A, thereby increasing the browsability compared with the embodiment described above and the modifications thereof. The present modification does not necessarily display the slice image included in the group having the largest total number of signal sources at the center in the region 401A. The display forms according to the modifications described above may be applied to the present modification.

Tenth Modification of the First Embodiment

While the first embodiment and the modifications thereof use the number of signal sources superimposed on the slice images as the condition of the slice images initially displayed in the region 401A, the present modification is not limited thereto. The present modification may apply the condition satisfying the object of an analysis, such as the vector direction and the intensity of the signal sources.

The second display controller 262, for example, may use the value indicating the validity or the credibility of the estimated signal source or approximate validity or credibility of the signal source and display the slice image with the signal source having the highest value superimposed thereon at the center in the region 401A. The value indicating the validity or the credibility (hereinafter, simply referred to as the credibility) can be calculated using good of fitness (GOF), for example. The second display controller 262 displays the slice image with the signal source having the calculated value indicating the credibility exceeding a predetermined threshold superimposed thereon in the region 401A. The second display controller 262 displays the slice image with the signal source having the largest value indicating the credibility (having the highest credibility) superimposed thereon in the region 401A. The second display controller 262 displays the other slice images such that they are disposed side by side in order of the slice numbers (layers) on the left and right sides. The present modification does not necessarily display the slice image having the largest value indicating the credibility at the center in the region 401A. The display forms according to the modifications described above may be applied to the present modification.

FIG. 26 illustrates an example where the display form according to the ninth modification illustrated in FIG. 25 is applied to the present modification. The display form according to the present modification is different from the display form illustrated in FIG. 25 in that the number indicated by the information 440B is not the number of signal sources but the value indicating the credibility. The value indicating the credibility illustrated in FIG. 26 may be the average of the credibility of the signal sources superimposed on the slice images included in one group or the value of the signal source having the highest value indicating the credibility out of the signal sources superimposed on the slice images included in one group.

The present modification identifies the signal source having high credibility. As a result, the analyzer can identify the target point assumed to be the cause of a case more accurately. The present modification may display the number of signal sources as the number indicated by the information 440B as illustrated in FIG. 25. In this case, the present modification may distinguish the credibility by causing the expression (e.g., color, shape, and size) of the signal sources to correspond to the value of GOF.

Eleventh Modification of the First Embodiment

While the tenth modification displays the signal sources having a value indicating the credibility equal to or larger than the predetermined threshold in a manner superimposed on the slice images, the present modification is not limited thereto. The present modification, for example, also displays the images having low credibility. The present modification displays the slice images with the signal sources having a value indicating the credibility equal to or larger than the predetermined threshold superimposed thereon in a manner distinguished from the slice images having low credibility. The present modification, for example, may use different colors for the background color of the slice images between the values equal to or larger than the threshold and the values smaller than the threshold. Alternatively, the present modification may use different colors for the outer frame of the slice images or display a mark for calling the analyzer's attention in the slice images. If the signal source having a value equal to or larger than the threshold and the signal source having a value smaller than the threshold are superimposed on one slice image, the present modification may display the signal sources in a manner distinguished form each other by the expression (e.g., color, shape, and size) of the signal sources.

Twelfth Modification of the First Embodiment

The present modification, which is another example of the tenth modification, calculates the average coordinates of all the signal sources. The slice image corresponding to the average coordinates is displayed at the center in the region 401A. The other slice images are displayed such that they are disposed side by side in order of the slice numbers (layers) on the left and right sides of the slice image displayed at the center. This display form enables the analyzer to visually recognize the spread of the positions of the signal sources from the average coordinates. The present modification does not necessarily display the slice image corresponding to the average coordinates at the center in the region 401A. The display forms according to the modifications described above may be applied to the present modification.

In another example, the present modification may calculate the center number between the largest number and the smallest number out of the slice numbers of the slice images on which the signal sources are present. The second display controller 262 may display the slice image corresponding to the center number at the center in the region 401A. The other slice images may be displayed such that they are disposed side by side in order of the slice numbers (layers) on the left and right sides. This display form enables the analyzer to visually recognize the spread from the center of the target point. Also in this example, the present modification does not necessarily display the slice image corresponding to the center coordinates at the center in the region 401A. The display forms according to the modifications described above may be applied to the present modification.

Second Embodiment

The following describes a second embodiment of the present invention. Explanation of the components common to the embodiment described above is appropriately omitted. The basic apparatus configuration according to the second embodiment is the same as the first embodiment. The analysis screen according to the embodiment above displays the biological data of a predetermined time length (considered to be "one piece of biological data"). By contrast, the first display controller 261 according to the present embodiment defines a plurality of pieces of biological data divided in units of a predetermined time length as a display target and displays the signal waveforms of any one of the pieces of biological data corresponding to the time zone 120b.

The analyzing unit 252 (estimating unit) estimates the signal source corresponding to the annotation selected from a plurality of annotations already input to the biological data in each of the pieces of biological data divided in units of the predetermined time length. The second display controller 262 controls display of one or more biological tomographic images in a variable manner based on the number of signal sources corresponding to part of the pieces of biological data. In this example, the second display controller 262 displays the signal source corresponding to part of the pieces of biological data divided in units of the predetermined time length in a manner superimposed on a plurality of sliced biological tomographic images. In addition, in the same manner as the first embodiment, the second display controller 262 performs control to initially display the biological tomographic image with the predetermined signal source superimposed thereon out of the sliced biological tomographic images in the display region. The following describes the specific contents.

Operations in the Measurement Recording

Figure 27:
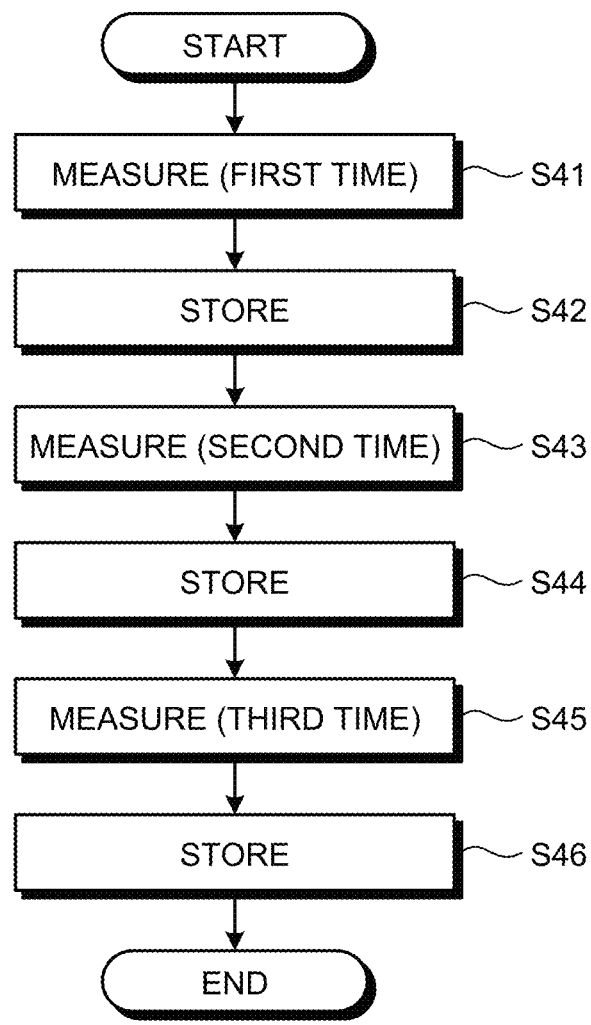
FIG. 27 is a flowchart of exemplary operations (operations performed three times in measurement recording) performed by the information processing apparatus according to a second embodiment of the present invention.

Let us assume a case where the measurement operation described in the first embodiment is performed three times intermittently, for example, and a predetermined interval (the length of the interval is optionally determined) is provided between the measurements. The frequency of "three times" is given by way of example only, and the present embodiment is not limited thereto. In other words, the frequency of measurement can be optionally changed depending on the object of an examination. FIG. 27 is a flowchart of exemplary operations (operations performed three times in the measurement recording) performed by the information processing apparatus 50. As illustrated in FIG. 27, the information processing apparatus 50 performs the first measurement at Step S41. The operations performed in the first measurement are the same as the processing from Step S12 to Step S17 illustrated in FIG. 8. If the first measurement ends, the information processing apparatus 50 stores the measurement data including the biological data acquired by the first measurement and the input annotations in the recording/analysis information storage unit 254 in a manner associated with the subject ID for identifying the subject (Step S42).

Subsequently, the information processing apparatus 50 performs the second measurement (Step S43). The operations performed in the second measurement are the same as the processing from Step S12 to Step S17 illustrated in FIG. 8. If the second measurement ends, the information processing apparatus 50 stores the measurement data including the biological data acquired by the second measurement and the input annotations in the recording/analysis information storage unit 254 in a manner associated with the subject ID for identifying the subject (Step S44).

Subsequently, the information processing apparatus 50 performs the third measurement (Step S45). The operations performed in the third measurement are the same as the processing from Step S12 to Step S17 in FIG. 8. If the third measurement ends, the information processing apparatus 50 stores the measurement data including the biological data acquired by the third measurement and the input annotations in the recording/analysis information storage unit 254 in a manner associated with the subject ID for identifying the subject (Step S46).

As described above, every time one measurement (measurement over a predetermined time length) is completed, the measurement data indicating the measurement results is stored in the recording/analysis information storage unit 254 in units of a file. In the following description, the file of one piece of measurement data stored in the recording/analysis information storage unit 254 may be referred to as a "measurement file". In this example, three measurement files are stored in the recording/analysis information storage unit 254 after the measurement performed three times ends. In the following description, the measurement file corresponding to the first measurement may be referred to as a first measurement file, the measurement file corresponding to the second measurement may be referred to as a second measurement file, and the measurement file corresponding to the third measurement may be referred to as a third measurement file. As described above, the measurement files are stored in the recording/analysis information storage unit 254 in a manner associated with the subject ID.

Operations in the Analysis

Figure 28:
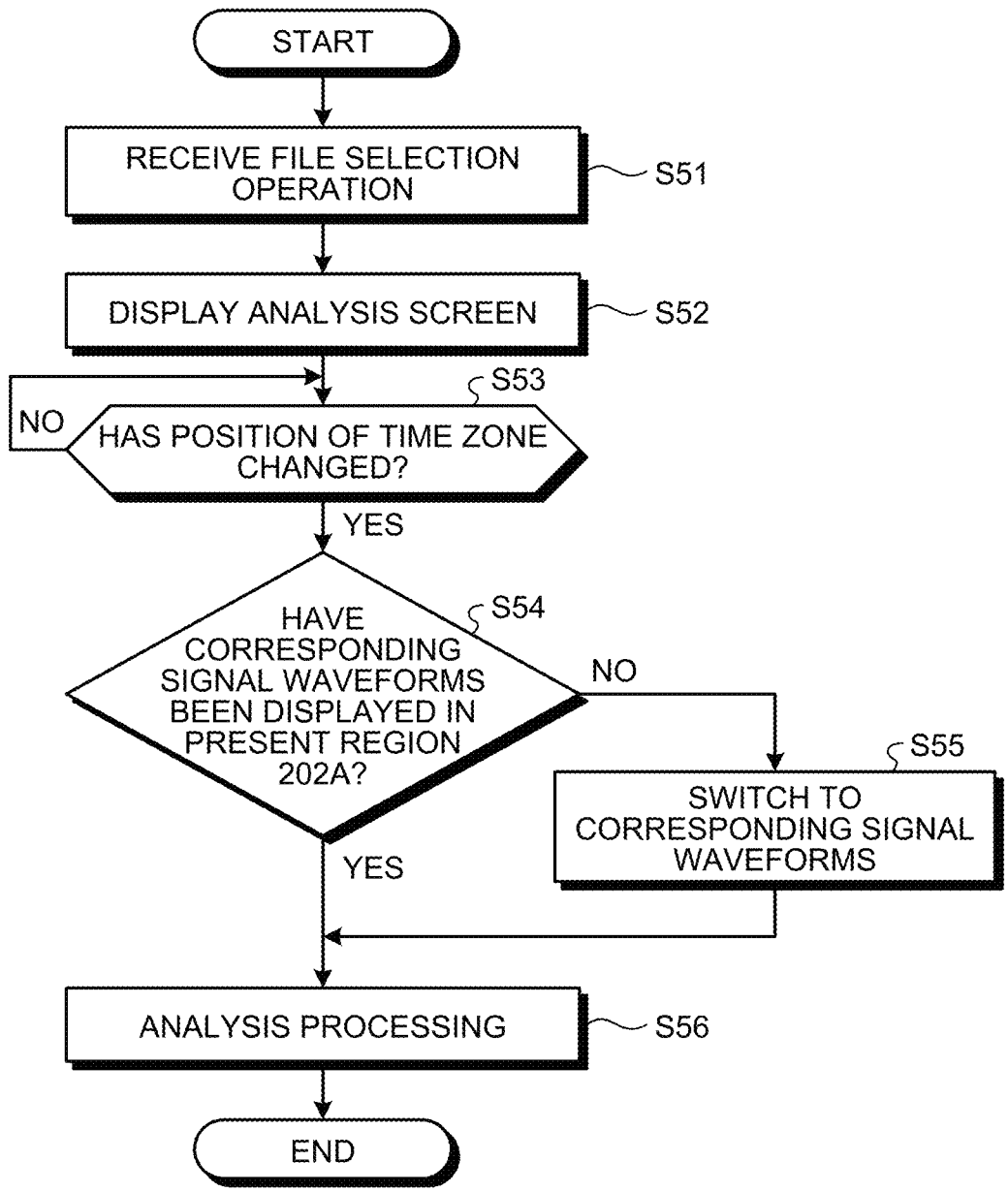
FIG. 28 is a flowchart of exemplary operations performed by the information processing apparatus according to the second embodiment.

The following describes the operations in the analysis. If pressing of the "analysis button" is received on the start screen 204 illustrated in FIG. 2, the information processing apparatus 50 (first display controller 261) is assumed to display the selection screen for selecting a measurement file acquired by the measurement on the display device 28. FIG. 28 is a flowchart of exemplary operations performed by the information processing apparatus 50.

The information processing apparatus 50 (first display controller 261) receives an operation for selecting a measurement file from the selection screen (Step S51). Subsequently, the information processing apparatus 50 (first display controller 261) performs control to read a series of measurement files (the three measurement files described above in this example) including the measurement file selected at Step S51 and one or more measurement files associated with the same subject ID as the subject ID associated with the measurement file and display the analysis screen on which the read series of measurement files are reflected on the display screen 28 (Step S52).

Figure 29:
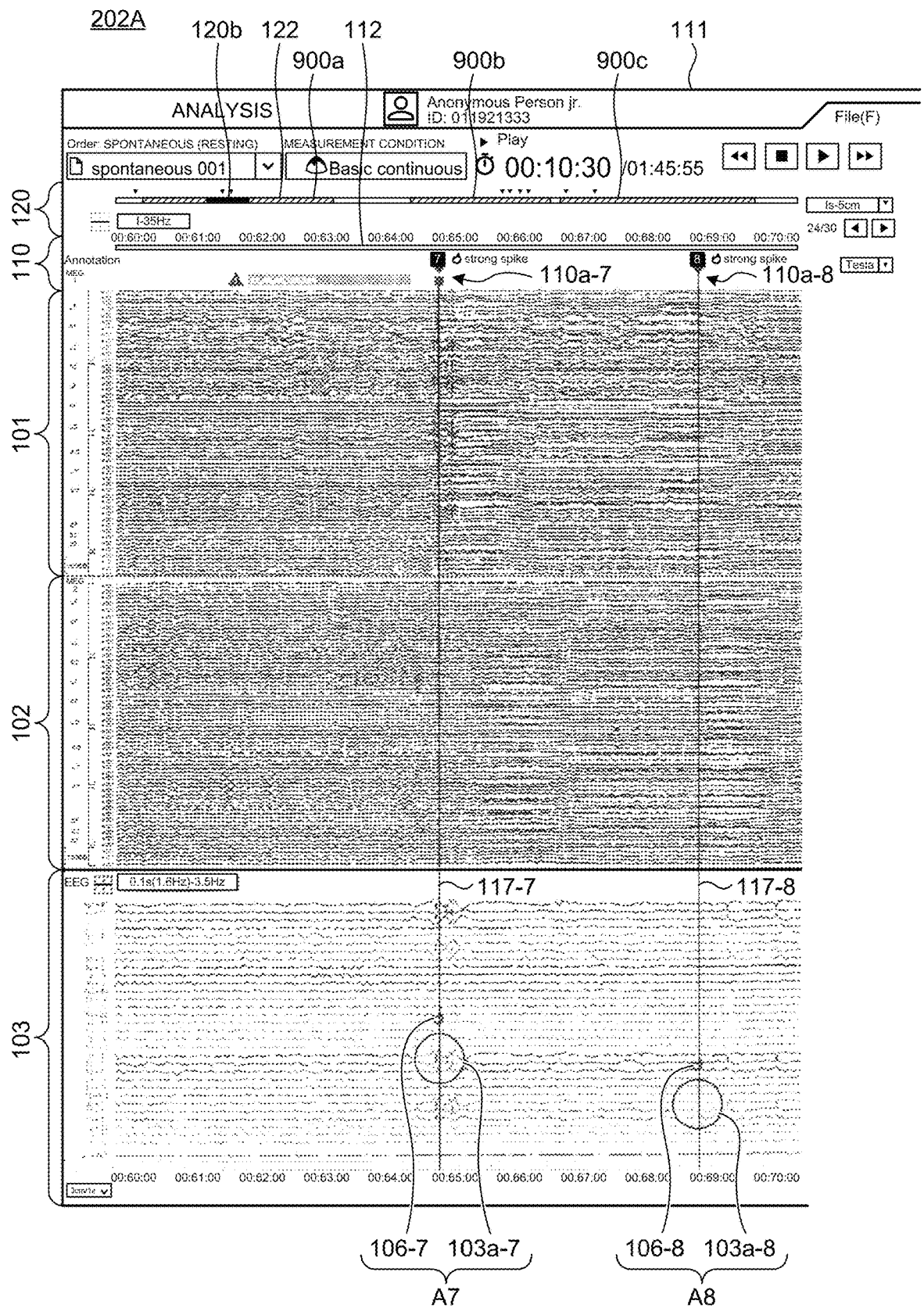
FIG. 29 is a view of a left region of the analysis screen according to the second embodiment.

FIG. 29 is a view of the left region 202A of the analysis screen. The time axis 122 displays not the entire recording time corresponding to any one of the measurement files but the entire time including all the recording times for the series of measurement files (the first, the second, and the third measurement files). The time axis 122 displays range information 900a indicating the recording period for the first measurement file, range information 900b indicating the recording period for the second measurement file, and range information 900c indicating the recording period for the third measurement file. In the following description, the pieces of range information 900a, 900b, and 900c may be simply referred to as "range information 900" when they are not distinguished from one another. The pieces of range information 900 may be each provided with information indicating the name of the corresponding measurement file. In this example, gaps (space areas) are provided between the pieces of range information 900 on the time axis 122 because the measurements are performed at intervals. The analyzer can switch the signal waveforms displayed in the region 202A by performing an operation of moving the time zone 120b using the mouse or the like. In this example, the signal waveforms corresponding to the time zone 120b (part of the biological data of any one of the measurement file) are displayed in the region 202A. In other words, the analyzer can display the signal waveforms in a desired period of time across the measurement files in the region 202A by moving the time zone 120b on the time axis 122. The annotation list 180 in the right region 202B on the analysis screen displays all the annotations included in the three measurement files. The measurement files may be each associated with the name of the target examination, for example, and the name of the corresponding examination may be displayed with the time zone 120b on the analysis screen.

Referring back to FIG. 28, if the information processing apparatus 50 (first display controller 261) displays the analysis screen at Step S52 and then receives an operation of changing the position of the time zone 120b (Yes at Step S53), the information processing apparatus 50 determines whether the signal waveforms corresponding to the changed position of the time zone 120b have been displayed in the present region 202A (Step S54).

If the result at Step S54 is negative (No at Step S54), the information processing apparatus 50 (first display controller 261) switches the signal waveforms displayed in the region 202A to the signal waveforms corresponding to the changed position of the time zone 120b (Step S55). If the result at Step S54 is positive (Yes at Step S54) or after Step S55, the information processing apparatus 50 performs the analysis processing based on the operation performed by the analyzer (Step S56). The contents of the analysis processing correspond to the processing from Step S23 to Step S31 illustrated in FIG. 15. As described above, the annotation list 180 displays all the annotations included in the three measurement files. If pressing of the merge button 300 is received at Step S29, the second display controller 262 performs control to display a plurality of tomographic images having a plurality of superimposed signal sources in a one-to-one correspondence with a plurality of annotations provided with the estimation completion marks 182 out of the annotations displayed in the annotation list 180 (all the annotations over the measurement files) in a manner disposed side by side based on the number of signal sources superimposed thereon. In other words, the set of the signal sources superimposed on the slice images illustrated in FIG. 19 corresponds to the signal sources in a one-to-one correspondence with the annotations subjected to estimation of the signal sources out of all the annotations over the measurement files.

First Modification of the Second Embodiment

Figure 30:
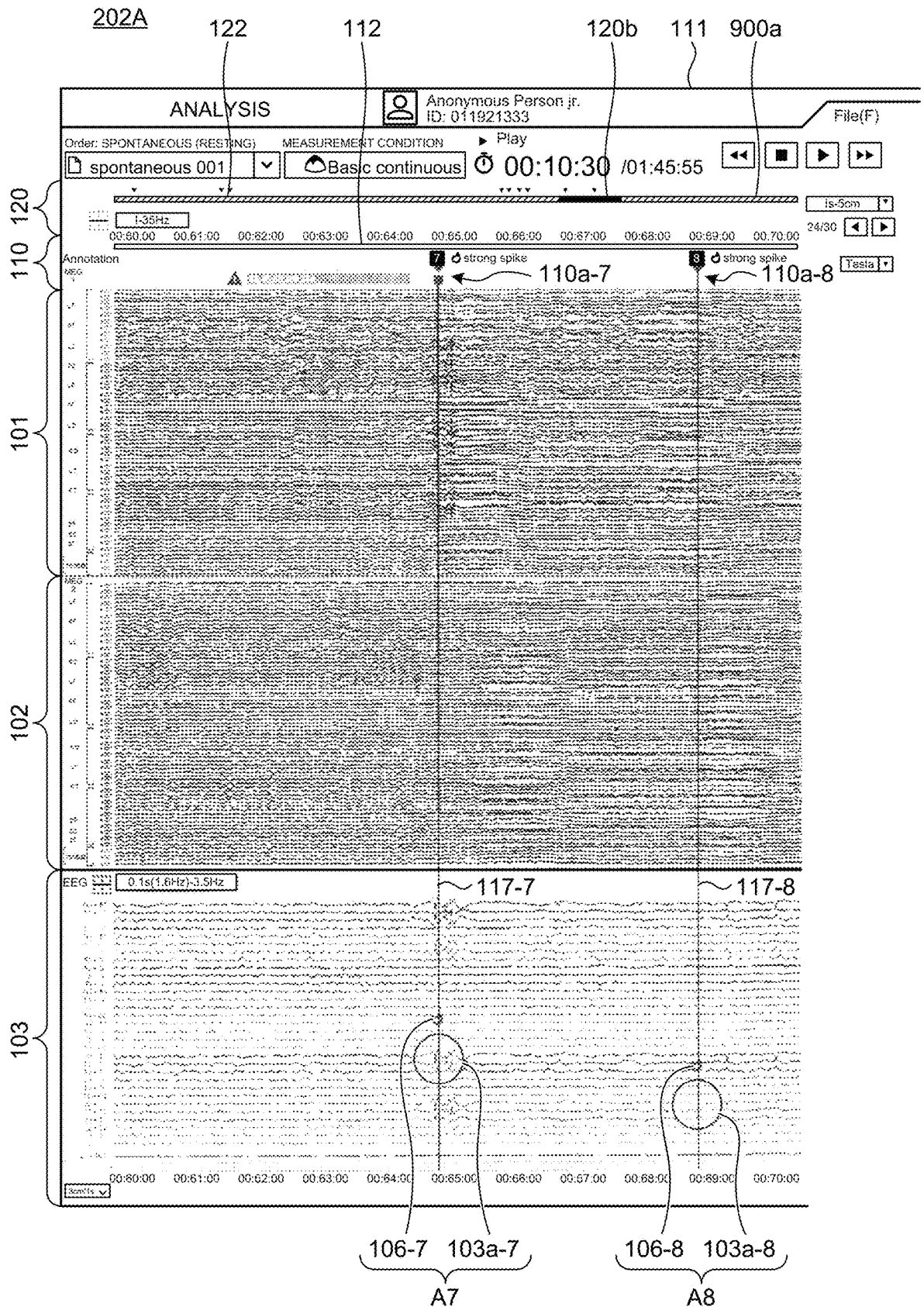
FIG. 30 is a view of an example of the analysis screen according to a modification of the second embodiment.

The time axis 122 on the analysis screen may display only the range information 900 corresponding to any one of the measurement files, for example. Based on the operation performed by the analyzer, the range information 900 on the time axis 122 may be switched in units of a measurement file. FIG. 30 is a view of an example of the analysis screen. In the example illustrated in FIG. 30, the time axis 122 displays only the range information 900a indicating the recording period for the first measurement file. If the information processing apparatus 50 (first display controller 261) receives an operation for switching the range information 900 performed by the analyzer, the information processing apparatus 50 switches the range information 900 on the time axis 122 in units of a measurement file based on the received operation. The information processing apparatus 50 changes the display in the display regions 202A and 202B corresponding to the measurement file resulting from the switching.

Second Modification of the Second Embodiment

The position of the time zone 120b according to the second embodiment is set so as not to extend across a gap between different pieces of range information 900. Let us assume a case where the time zone 120b is positioned at the end of the range information 900a illustrated in FIG. 29, for example. If the information processing apparatus 50 (first display controller 261) receives an operation of forwarding the position of the time zone 120b by one stage, the information processing apparatus 50 switches the display of the time zone 120b such that the time zone 120b is positioned at the start of the next range information 900b without extending across the gap between the range information 900a and the range information 900b.

The present modification is not limited to the configuration described above. The time zone 120b according to the present modification may extend across the gap between different pieces of information 900. In this case, as illustrated in FIG. 31A, the signal waveforms corresponding to the time zone 120b have a space area (corresponding to a gap between measurements) in which no biological signal is present. To facilitate the analyzer's visually recognizing that the space area is an area between different measurement files, for example, the information processing apparatus 50 (first display controller 261) may change and display the background of the space area as illustrated in FIG. 31B.

Let us assume a case were the time zone 120b extends across the gap between different pieces of information 900, and the time interval between the measurement is short, for example. In this case, a small gap may possibly be present between the signal waveforms corresponding to one measurement file and the signal waveforms corresponding to the other measurement file. In this case, as illustrated in FIG. 31C, for example, the information processing apparatus 50 (first display controller 261) may display a line representing the joint (line different from the annotation line) between the signal waveforms corresponding to one measurement file and the signal waveforms corresponding to the other measurement file.

Alternatively, as illustrated in FIG. 31D, for example, the information processing apparatus 50 (first display controller 261) may display the signal waveforms corresponding to one measurement file and the signal waveforms corresponding to the other measurement file in different display forms. Still alternatively, as illustrated in FIG. 31E, for example, the information processing apparatus 50 (first display controller 261) may change the color of the background of the signal waveforms corresponding to one of the measurement files.

Third Modification of the Second Embodiment

Figure 32:
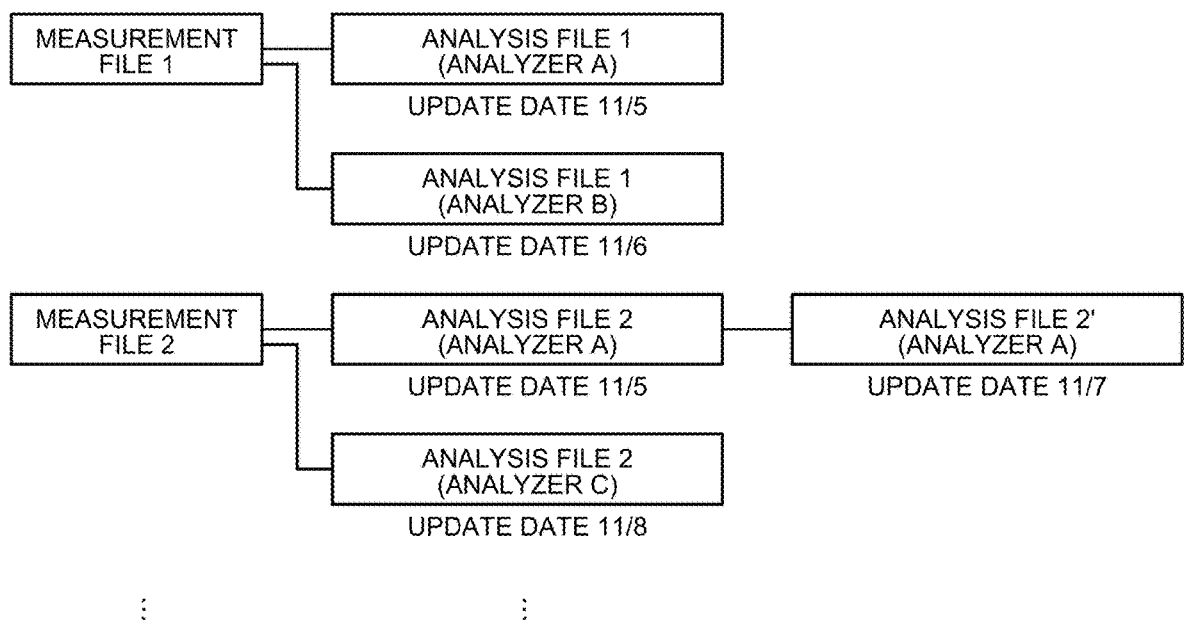
FIG. 32 is a diagram schematically illustrating management of analysis files in a manner associated with each of measurement files.

As illustrated in FIG. 32, the information processing apparatus 50 according to the second embodiment manages (stores) analysis files indicating analysis results (analysis information) in a manner associated with each of the measurement files. The number of analyzers is not necessarily one, and a plurality of analyzers may perform analyses. In this case, different analysis files are generated by each of the analyzers and associated with the measurement files. In this example, every time an analysis ends, the analysis file indicating the analysis result is newly associated with the measurement file. In other words, if the information processing apparatus 50 receives input of an analysis end command every one analysis, the information processing apparatus 50 newly stores the analysis file indicating the analysis result in a manner associated with the measurement file. The analysis end command may be input by the analyzer by pressing a button indicating "save" or "end" on the analysis screen, for example.

If the annotations of all the files are displayed in the annotation list 180 on the analysis screen, annotations not being analyzed are also displayed to an analyzer who has logged in and is performing analysis. This makes it necessary for the analyzer to find the annotations analyzed by himself/herself from all the annotations, thereby increasing the load.

Figure 33:
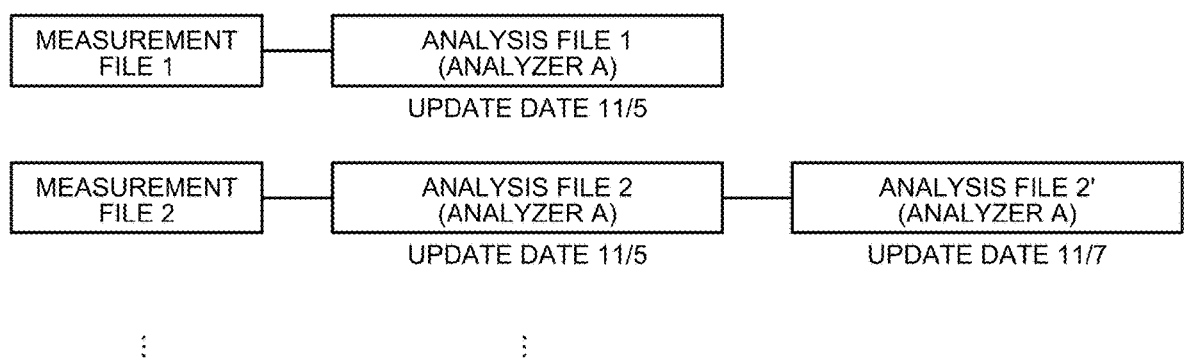
FIG. 33 is a diagram of an example of a selection screen according to a modification of the second embodiment.

To address this, the information processing apparatus 50 according to the present modification manages the analysis files in a manner each associated with the analyzer, the update date (creation date of the analysis file), and the subject ID. Upon receiving If the information processing apparatus 50 (first display controller 261) receives pressing of the "analysis" button on the start screen 204 illustrated in FIG. 2, the information processing apparatus 50 extracts analysis files corresponding to the logged-in analyzer from the analysis files included in a file list illustrated in FIG. 32. The information processing apparatus 50 displays the selection screen associated with the extracted analysis files in each of the measurement files on the display device 28. For the measurement files not associated with the extracted analysis files, only the measurement files are displayed. If the logged-in analyzer is an analyzer "A", for example, the information processing apparatus 50 extracts the analysis files corresponding to the analyzer "A" from the analysis files included in the file list illustrated in FIG. 32 and displays the selection screen illustrated in FIG. 33.

If the information processing apparatus 50 receives selection of any one of the measurement files from the selection screen, the information processing apparatus 50 displays the analysis screen on which a series of measurement files are reflected. The series of measurement files include the selected measurement file and one or more measurement files associated with the same subject ID as the subject ID associated with the measurement file. For the display in the annotation list 180 on the analysis screen, the information processing apparatus 50 (first display controller 261) identifies the analysis file associated with the measurement file for each of the series of measurement files and displays the annotations corresponding to the identified analysis file in the annotation list 180. If a plurality of analysis files of the same analyzer are associated with one measurement file, the information processing apparatus 50 identifies the analysis file having the latest update date and displays the annotations corresponding to the identified analysis file in the annotation list 180. If no analysis file is associated with one measurement file, the information processing apparatus 50 displays the annotations included in the measurement file in the annotation list 180.

On the selection screen, the analyzer may select all the measurement files to be displayed, for example. If the analyzer "A" selects a measurement file 2 on the selection screen illustrated in FIG. 33, for example, the information processing apparatus 50 (first display controller 261) may display the analysis screen on which only the measurement file 2 is reflected. For the display in the annotation list 180 on the analysis screen, the information processing apparatus 50 (first display controller 261) displays the annotations corresponding to an analysis file 2' having the latest update date out of the two analysis files 2 and 2' associated with the measurement file 2 in the annotation list 180.

As described above, the annotation list 180 on the analysis screen appropriately displays only the annotations corresponding to the logged-in analyzer, thereby improving the analyzer's convenience.

Login means having the authority to use the information processing apparatus 50. The information processing apparatus 50 has a function to determine whether to permit the login of a user (analyzer). When the information processing apparatus 50 is started, for example, it displays a login screen that urges the analyzer to input information for login (e.g., login information including a combination of an ID and a password), and the analyzer inputs his/her login information into the login screen. The information processing apparatus 50 registers pieces of preset login information in a manner associated with the respective users having the use authority. If the login information input from the login screen matches the registered login information, the information processing apparatus 50 permits the login of the user (analyzer) who has input the login information. If the login information does not match the registered login information, the information processing apparatus 50 does not permit the login.

Third Embodiment

The following describes a third embodiment of the present invention.

The third embodiment is different from the first and the second embodiments in that it groups dipole estimation results of a plurality of times to increase the visibility and can change display by preparing a plurality of methods for grouping. In the following description of the third embodiment, the same components as the first and the second embodiments are not described, and only the components different from them are described.

In FIG. 20, for example, all the dipole estimation results 190a calculated at a plurality of times are displayed. The slice images A to C illustrated in FIG. 20 display the dipole estimation results in the same direction. If the dipole estimation result 190a represented by a in FIG. 34 is added to the slice images A to C in FIG. 20, for example, the dipole estimation result 190a has significantly low visibility as illustrated in FIG. 34 and may possibly be overlooked.

FIG. 35 is a view of an example of the slice image that displays the dipole estimation results 190a according to the third embodiment. To prevent the situation described above, the second display controller 262 according to the present embodiment displays the dipole estimation results 190a in different colors depending on their directions as illustrated in FIG. 35. To facilitate the understanding, FIG. 35 illustrates an example on a plane. The second display controller 262 derives which part of the color wheel illustrated at lower right in FIG. 35 the direction of the dipole estimation result 190a indicates. The second display controller 262 then colors the dipole estimation result 190a in the color of the indicated part of the color wheel. Also in a three-dimensional space, the second display controller 262 determines the colors of the dipole estimation results 190a in the same manner using a color solid.

Figure 36:
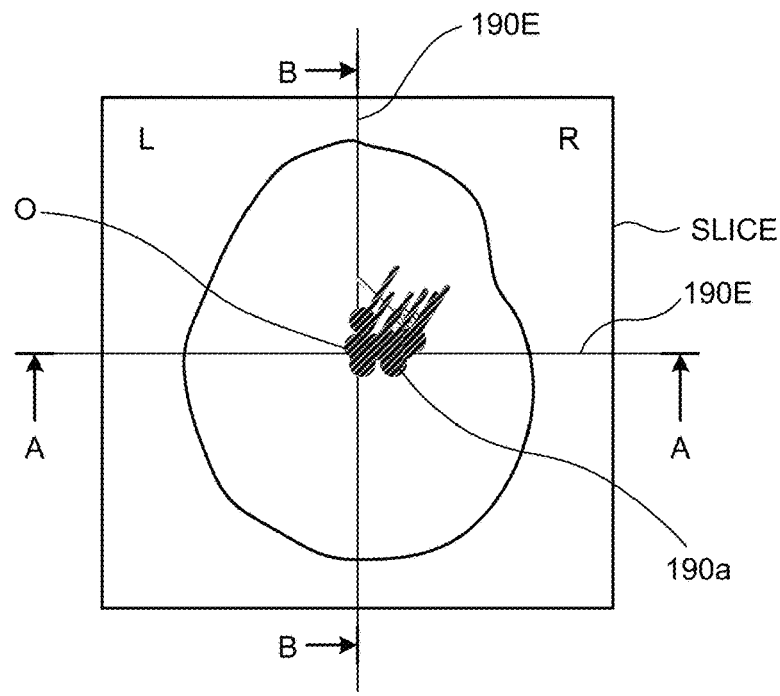
FIG. 36 is a view of another example of the slice image that displays the dipole estimation results.

If the dipole estimation results 190a are displayed as illustrated in FIG. 35, however, part of the dipole estimation results 190a may possibly have lower visibility as illustrated in FIG. 36 because of the vertical positional relation in which the dipole estimation results 190a superimpose.

To prevent the visibility from being reduced by superimposing many dipole estimation results 190a, the second display controller 262 performs grouping on the dipole estimation results 190a. In the example illustrated in FIG. 36, most of the dipole estimation results 190a have the same direction. By collectively displaying these dipole estimation results 190a, the second display controller 262 can increase the visibility.

Figure 37:
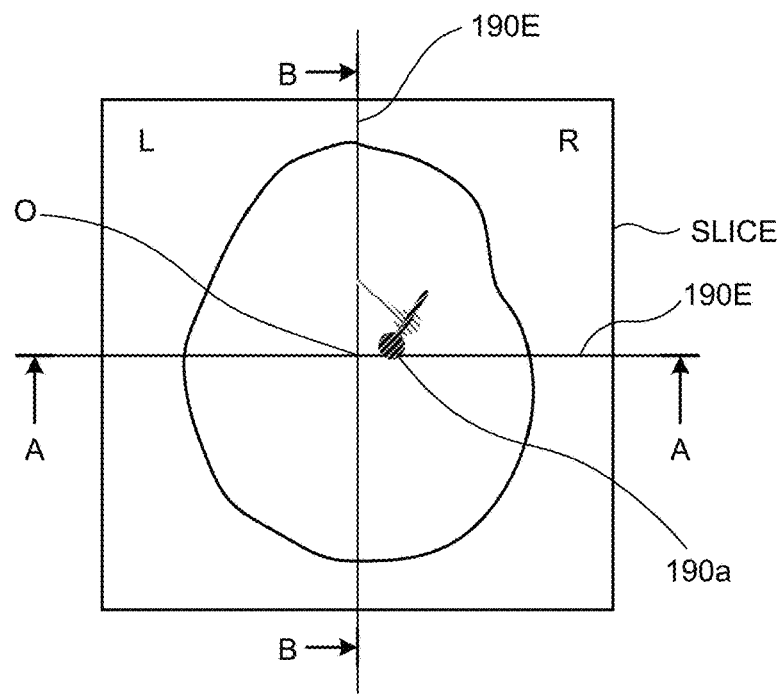
FIG. 37 is a view of an example of the slice image that displays the dipole estimation results resulting from grouping.

FIG. 37 is a view of an example of the slice image that displays the dipole estimation results 190a resulting from grouping. In the example illustrated in FIG. 37, the dipole estimation results 190a with the same direction illustrated in FIG. 36 are grouped.

Various methods for grouping (clustering) have been developed, and the second display controller 262 may perform grouping using any desired method. The following is important for medical examinations:

capable of selecting the method for grouping, and capable of adjusting parameters used for grouping, that is, capable of further integrating or distributing the dipole estimation results.

Figure 38:
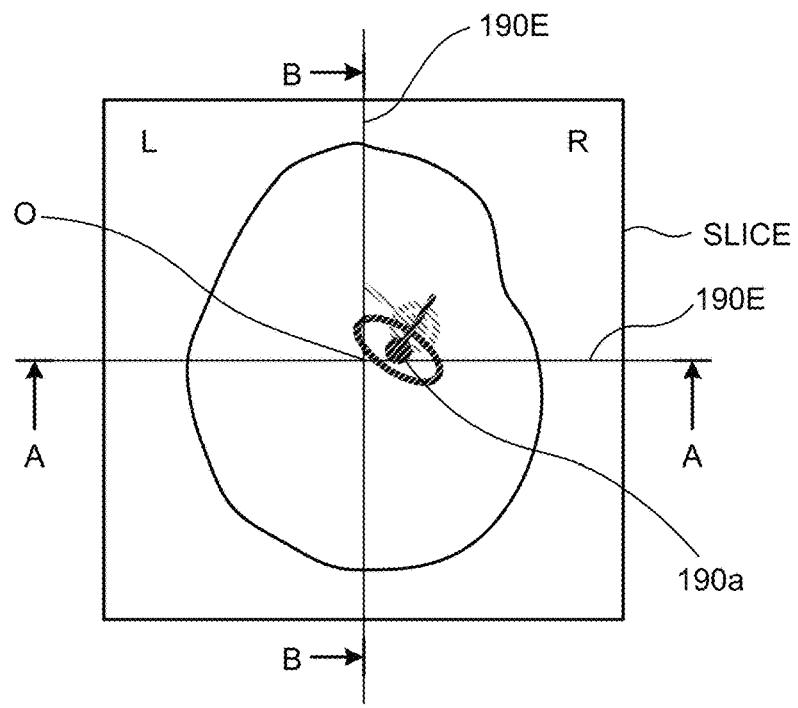
FIG. 38 is a view for explaining grouping using the confidence volume of the dipole estimation results.

The present embodiment, for example, employs a method for grouping using the confidence volume of the dipole estimation results 190a (refer to U.S. Pat. No. 7,840,039). FIG. 38 is a view for explaining grouping using the confidence volume of the dipole estimation results 190a. The likelihood of the position of each of the dipole estimation results 190a can be statistically calculated. The second display controller 262, for example, can calculate a 95% presence range of the position of the dipole estimation result 190a (range where the correct position of the dipole estimation result 190a is present with a probability of 95%). The second display controller 262 can display the range by an ellipse as illustrated in FIG. 38. By calculating the difference between the positions of the dipole estimation results 190a using the confidence volume, the present embodiment can evaluate the difference between the positions more appropriately (statistically) than calculating the different between the positions simply using a physical distance.

Figure 39:
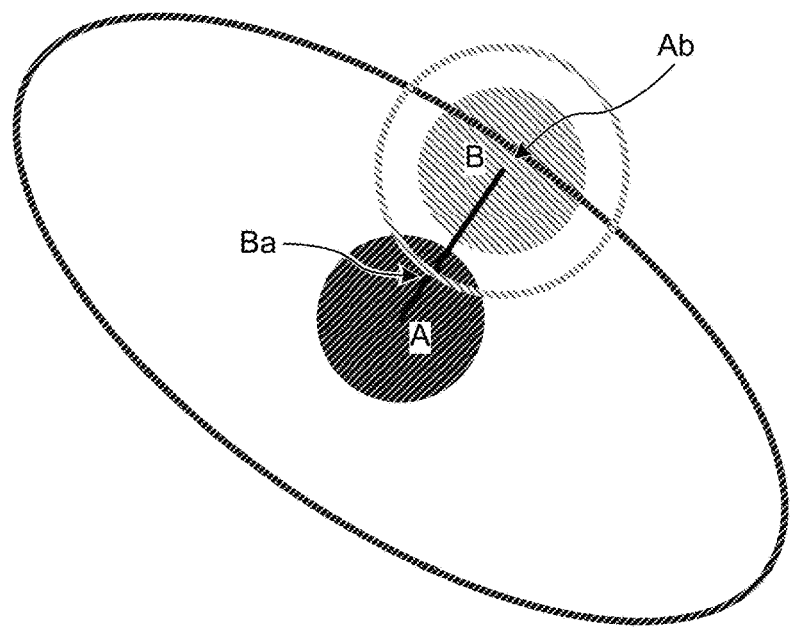
FIG. 39 is a view of an example of calculation of the difference (distance) between the positions using the confidence volume.

FIG. 39 is a view of an example of calculation of the difference (distance) between the positions using the confidence volume. FIG. 39 does not illustrate the straight line indicating the direction of the dipole estimation result 190a and illustrates only the circle (filled circle) indicating the center position and the ellipse (only the segment) indicating the confidence volume. The difference between the positions of the dipole estimation results 190a is usually evaluated by the distance between A and B. The reliability of the position of the dipole estimation result 190a, however, varies depending on the dipole estimation results 190a. The reliability is indicated by the confidence volume represented by the ellipse in FIG. 39. The present embodiment evaluates the difference between the positions more accurately by calculating the difference using the confidence volume.

As illustrated in FIG. 39, Ab and Ba are points at which a segment A-B or an extension of the segment A-B intersects the ellipse of the confidence volume. Difference D is defined by the following expression:

$$D=(A-B)/(A-Ab)+(A-B)/(B-Ba)$$

where X-Y is the distance between a point X and a point Y.

The second display controller 262 performs grouping using the difference D as the difference between the positions. Various methods for grouping are known, including k-means clustering and Ward's method, and the second display controller 262 may use any one of them. To employ a non-hierarchical method, such as the k-means clustering, the second display controller 262 needs to set an initial seed point. To set the initial seed point, the second display controller 262 may employ a method of referring to the likelihood (GOF) of the dipole estimation results 190a and determining the dipole estimation result 190a having the largest GOF to be the initial seed, for example.

In grouping, the second display controller 262 can use the information on the positions, the directions, and the intensities of the dipole estimation results 190a. In terms of an analysis of brain activity, the dipole estimation results 190a present at the same position but with different directions are preferably determined to be included in different groups. This is because the dipole estimation results 190a with different directions are assumed to be detected at the same position because of the low accuracy of position estimation, although the dipole estimation results 190a with the same direction are usually detected at the same position in the brain structure.

In grouping the dipole estimation results 190a, the present embodiment determines the dipole estimation results 190a present at the same position but with different directions, to be included in different groups. By performing grouping in stages by the following procedure, for example, the present embodiment can classify the dipole estimation results 190a present at the same position into different groups.

(1) performing grouping based on the directions of the dipole estimation results 190a (2) performing grouping with respect to each group in (1) while focusing on the positions of the dipole estimation results 190a (the dipole estimation results 190a classified into different groups by (1) are eventually not classified in the same group)

The parameters used for grouping (e.g., the convergence conditions of various kinds of clustering) are preferably adjusted appropriately by the user.

The following describes the method for displaying the dipole estimation results 190a grouped by the second display controller 262.

Figure 40:
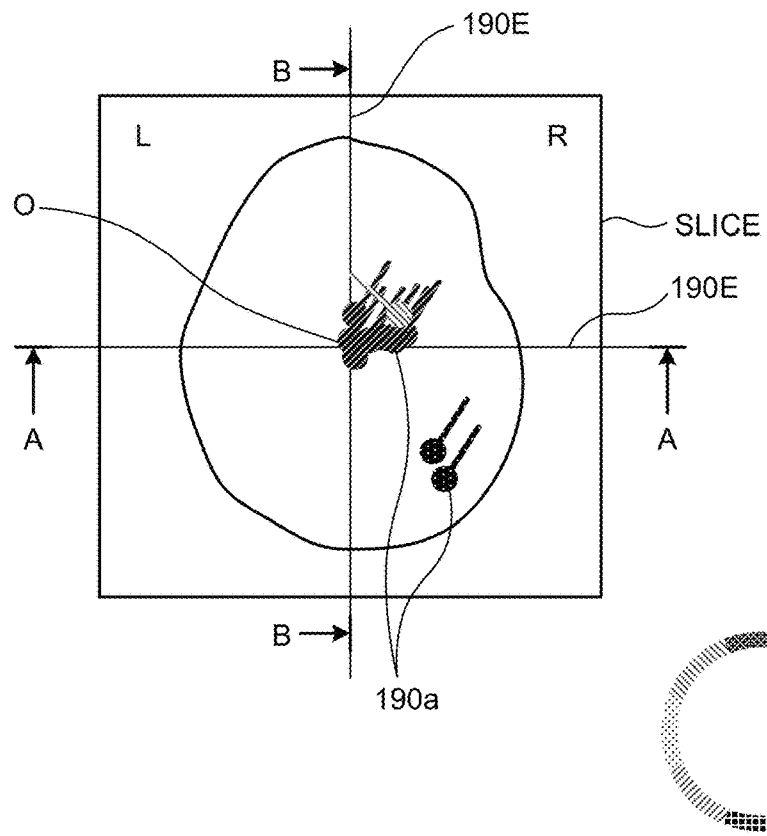
FIG. 40 is a view of an example where the dipole estimation results of different sources are displayed in the same color.

The second display controller 262, for example, performs classification by color as illustrated in FIG. 35 based on the groups. As illustrated in FIG. 40, however, the dipole estimation results 190a of different sources may possibly be displayed in the same color (or colors difficult to distinguish from each other).

Figure 41:
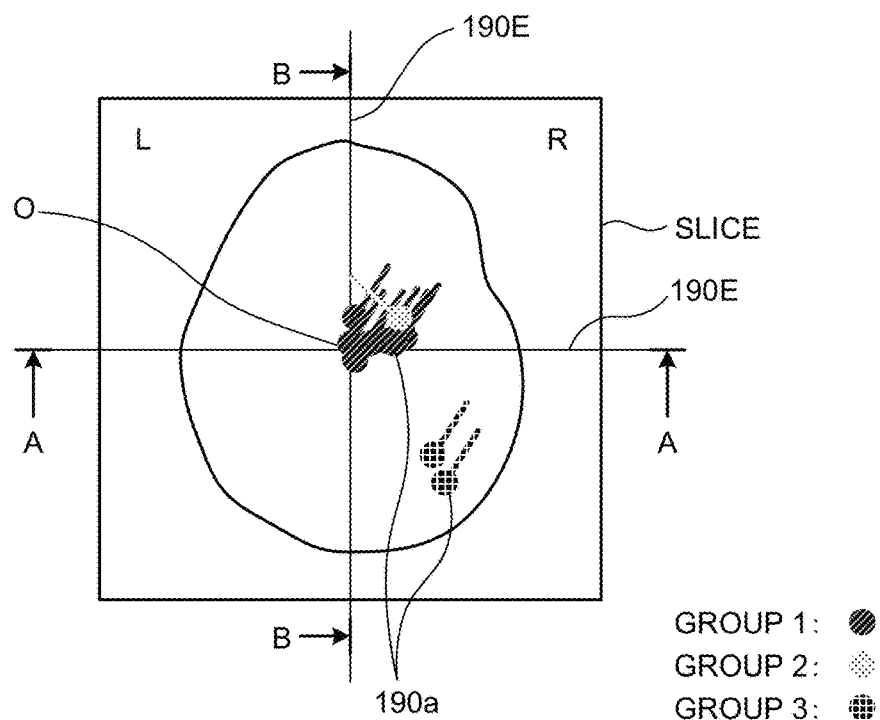
FIG. 41 is a view of an example where easily distinguishable colors are allocated to respective groups.

To address this, the second display controller 262 allocates colors that are easy to distinguish from each other to the respective groups. FIG. 41 is a view of an example where easily distinguishable colors are allocated to the respective groups. If the second display controller 262 performs grouping and allocates the easily distinguishable colors to the respective groups as illustrated in FIG. 41, the analyzer can distinguish the dipole estimation results 190a of different sources with high visibility.

The second display controller 262 may display not all the dipole estimation results 190a but only the dipole estimation results 190a representing the respective groups. The dipole estimation result 190a representing the group may be the dipole estimation result 190a present at a position closest to the center in the group or the dipole estimation result 190a having the highest reliability in the group, for example. Alternatively, the second display controller 262 may calculate the averages of the positions and the directions of the dipole estimation results 190a in the group and determine the dipole estimation result 190a present at the average position and with the average direction, to be the dipole estimation result 190a representing the group. In any case, the second display controller 262 selects/calculates the dipole estimation result 190a appropriate for the dipole estimation result 190a representing the group.

Figure 42:
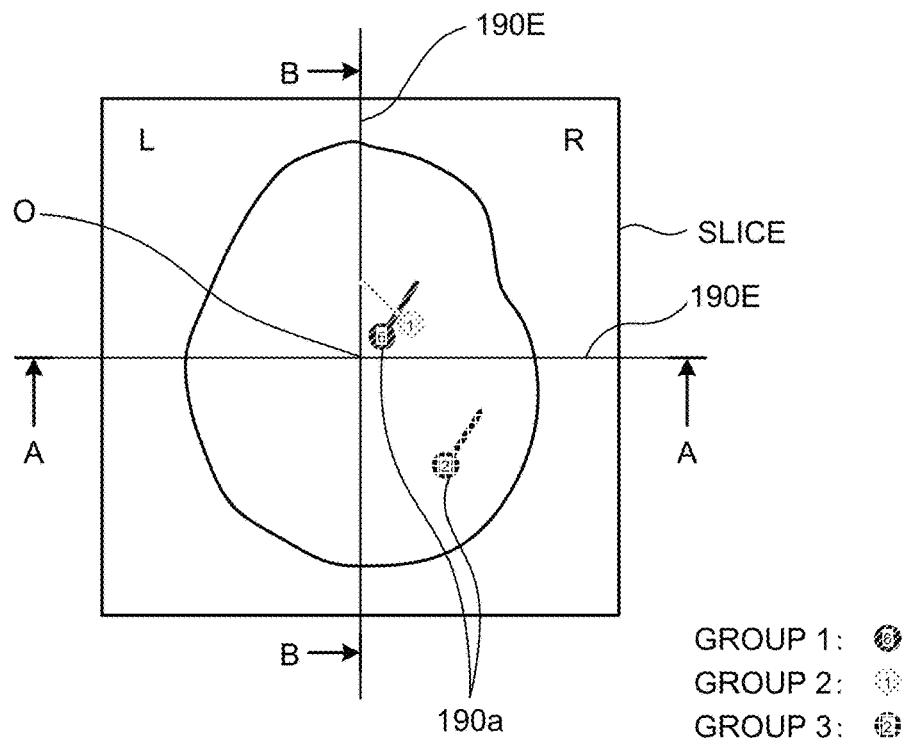
FIG. 42 is a view of an example where only the dipole estimation results representing the respective groups are displayed.
Figure 43:
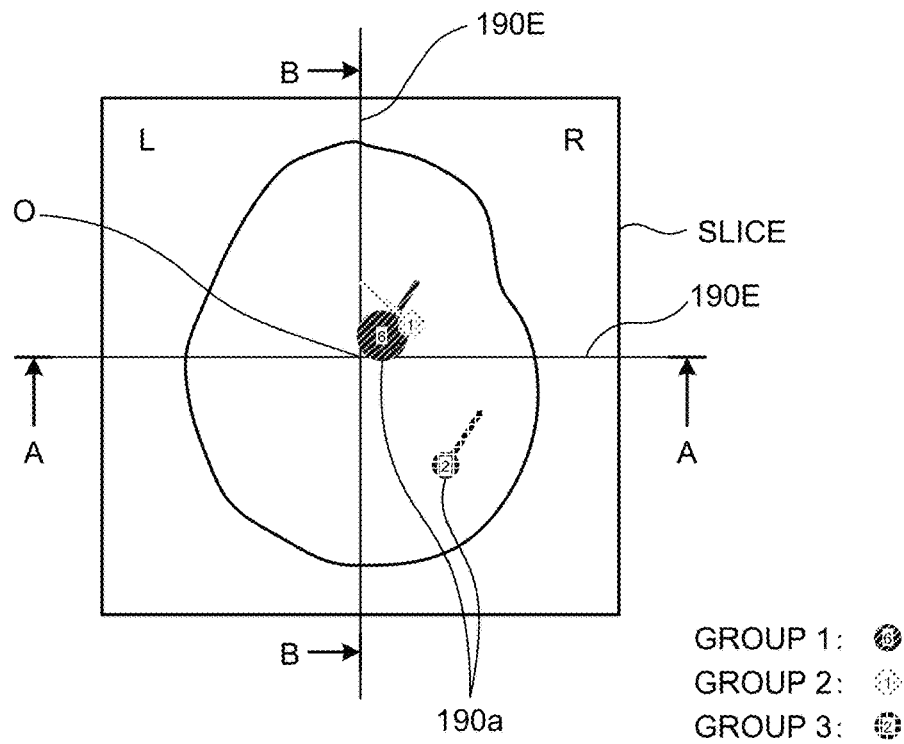
FIG. 43 is a view of another example where only the dipole estimation results representing the respective groups are displayed.

FIG. 42 is a view of an example where only the dipole estimation results 190a representing the respective groups are displayed. FIG. 43 is a view of another example where only the dipole estimation results 190a representing the respective groups are displayed. As illustrated in FIG. 42, the second display controller 262 displays the number of dipole estimation results 190a belonging to the group in the circle indicating the position of the dipole estimation result 190a. Furthermore, as illustrated in FIG. 43, the second display controller 262 changes the size of the circle indicating the position of the dipole estimation result 190a depending on the number of dipole estimation results 190a in the group.

As described above, to display only the representative dipole estimation result 190a for each group, the second display controller 262 preferably displays the information on the group (the number of dipole estimation results 190a, variations in the position, variations in the direction, and the average or variations in the reliability (GOF)) in a manner associated with the dipole estimation result 190a appropriately. In particular, the information on the direction of the dipole estimation result 190a is important for a diagnosis, and it is essential to display the statistical information, such as the variations in the direction, in a simple manner.

In the thesis "Sensorimotor seizures of pediatric onset with unusual posteriorly oriented rolandic spikes. Kakisaka Y1, Nakasato N, Haginoya K, Kanno A, Tsuchiya S. Epilepsy Res. 2009 April; 84(2-3): 153-8. doi: 10.1016/j.eplepsyres.2009.01.012. Epub 2009 Feb. 28", for example, benignancy or malignancy of epilepsy is determined based on the directions of the dipole estimation results 190a.

Figure 44:
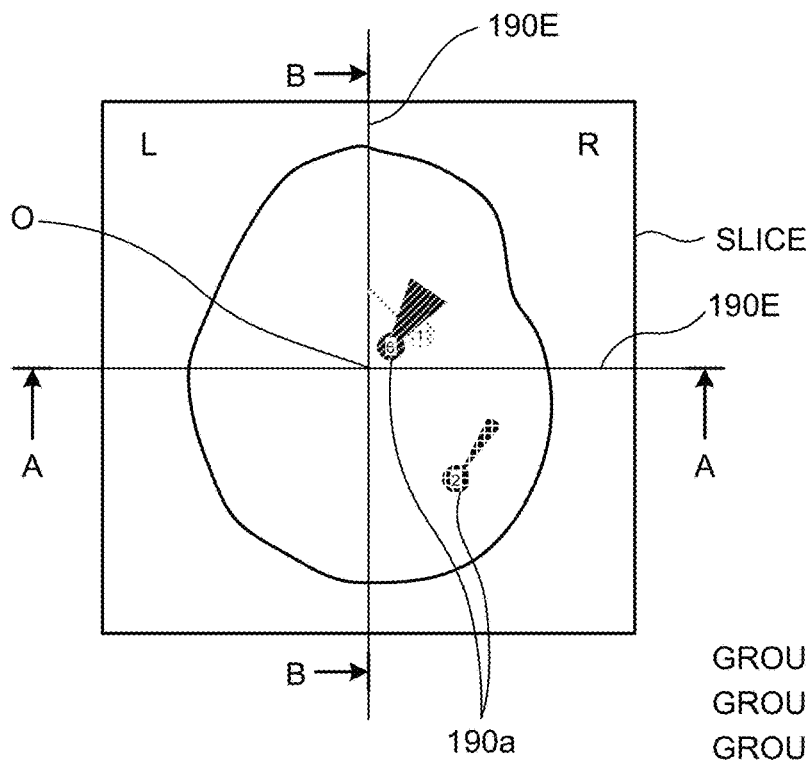
FIG. 44 is a view of a display example of variations in the direction in the groups.

FIG. 44 is a view of a display example of variations in the direction in the groups. As illustrated in FIG. 44, the second display controller 262 indicates the variations in the direction in the groups by the degree of spread at the distal end of the segment (trapezoid) indicating the direction of the dipole estimation results 190a.

Figure 45:
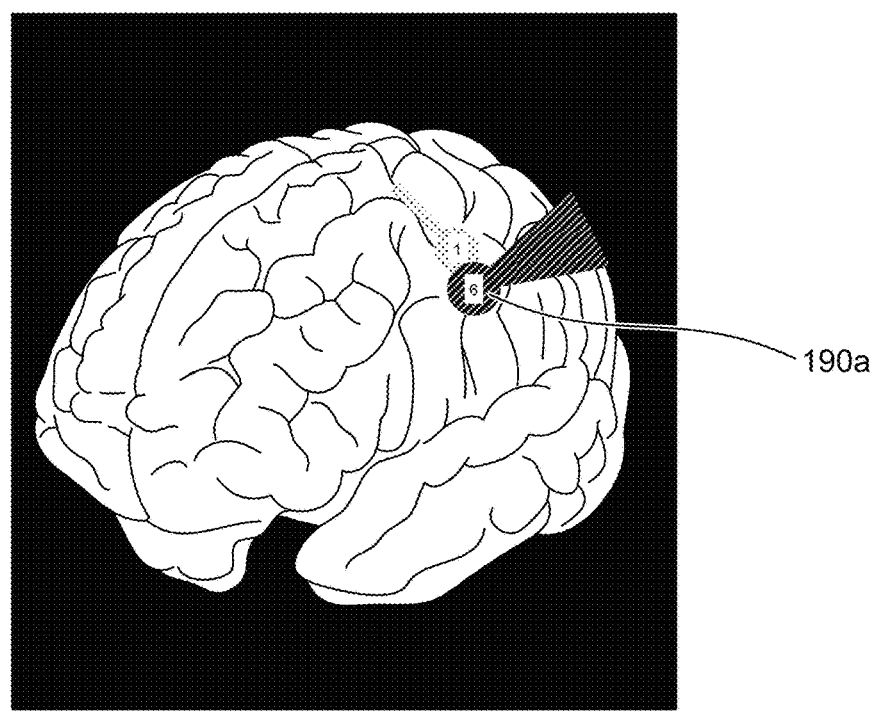
FIG. 45 is a view of an example where the dipole estimation results are superimposed on a three-dimensional image.

While the description has been made using three two-dimensional figures for the convenience of explanation, the same processing can be performed to superimpose the dipole estimation results 190a on a three-dimensional image. FIG. 45 is a view of an example where the dipole estimation results 190a are superimposed on a three-dimensional image.

Figure 46:
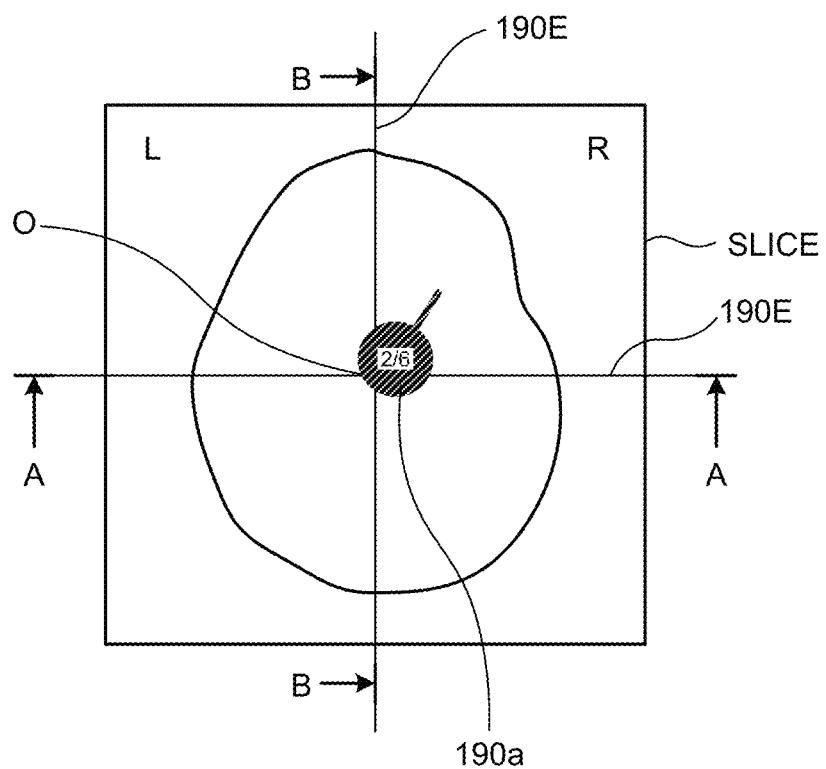
FIG. 46 is a view illustrating how many dipole estimation results are placed on the slice.

The second display controller 262 may display the representative dipole estimation result 190a on all the slices in which the annotations in the group are present. In this case, how many annotations are placed on each of the slices is preferably indicated. FIG. 46 is a view illustrating how many dipole estimation results 190a are placed on the slice. In the example illustrated in FIG. 46, the display "2/6" in the circle indicating the position of the displayed representative dipole estimation result 190a indicates that two dipole estimation results 190a out of six dipole estimation results 190a in the group are placed on the slice.

FIG. 47 is a view of an example obtained by reflecting the display illustrated in FIG. 46 on the screen illustrated in FIG. 19. The display on the screens illustrated in FIGS. 21 to 26 can be changed into the display based on the representative dipole estimation result 190a in the same manner.

To display the representative dipole estimation result 190a of the group, the display on the screens illustrated in FIGS. 19 to 26 may be performed as follows. The second display controller 262 determines the slice to be disposed at the center and the order of sorting the slices using the number of dipole estimation results 190a placed on the slices, for example. To display only the representative dipole estimation result 190a, the second display controller 262 can perform the same processing as follows:

(1) It is assumed that the number of dipole estimation results 190a in the group is present at the position of the representative dipole estimation result 190a.

(2) In an application example, the second display controller 262 can determine the slice to be disposed at the center and the order of sorting the slices using the information on the group (e.g., disposing the slice with the representative dipole estimation result 190a having the smallest variations in the group placed thereon at the center). While the first embodiment uses the information on one annotation, the statistical information on a plurality of annotations in the group becomes capable of being used likewise.

As described above, the present embodiment can group the dipole estimation results of a plurality of times to increase the visibility of the results. In addition, the present embodiment can change display by preparing a plurality of methods for grouping. Consequently, the analyzer can perform an analysis on the dipole estimation results of a plurality of times readily and appropriately by changing the display corresponding to the situation.

The computer programs executed by the biological signal measurement system 1 according to the embodiments above may be recorded and provided on a computer-readable recording medium, such as a compact disc read only memory (CD-ROM), a flexible disk (FD), a compact disc recordable (CD-R), a digital versatile disc (DVD), and in a universal serial bus (USB), as an installable or executable file or provided or distributed via a network, such as the Internet. The various computer programs may be embedded and provided in a ROM, for example.

An embodiment can increase the visibility of dipole estimation results of a plurality of times by grouping.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. An information processing apparatus comprising:
a display controller configured to,
determine directions of dipole estimation results of a signal source corresponding to part of biological data indicating a chronological change of a biological signal,
group ones of the dipole estimation results with a same direction out of the dipole estimation results as grouped dipole estimation results,
display the grouped dipole estimation results in a manner superimposed on a plurality of biological tomographic images sliced in a predetermined direction, and
display a non-grouped dipole estimation result in a different color or form from a color or a form of the grouped dipole estimation results depending on a direction of the non-grouped dipole estimation result.

2. The information processing apparatus according to claim 1, wherein the display controller is configured to display the grouped dipole estimation results in a distinguishable color or form for each group when displaying the non-grouped dipole estimation result.

3. The information processing apparatus according to claim 1, wherein the display controller is configured to display a dipole estimation result representing a group when displaying the grouped dipole estimation results.

4. The information processing apparatus according to claim 3, wherein the display controller is configured to display information on the group together with the dipole estimation result representing the group.

5. The information processing apparatus according to claim 4, wherein the display controller is configured to display the information on the group using the color or the form of the dipole estimation result.

6. The information processing apparatus according to claim 1, wherein the display controller is configured to determine the directions of the dipole estimation results by calculating a difference between positions of dipole estimation results using a confidence volume of the dipole estimation results.

7. An information processing method comprising:
determining directions of dipole estimation results of a signal source corresponding to part of biological data indicating a chronological change of a biological signal;
grouping ones of the dipole estimation results with a same direction out of the dipole estimation results of grouped dipole estimation results;
displaying the grouped dipole estimation results in a manner superimposed on a plurality of biological tomographic images sliced in a predetermined direction; and
displaying a non-grouped dipole estimation result in a different color or form from a color or a form of the grouped dipole estimation results depending on a direction of the non-grouped dipole estimation result.

8. A non-transitory computer-readable recording medium having stored therein a computer program causing a computer to perform:
determining directions of dipole estimation results of a signal source corresponding to part of biological data indicating a chronological change of a biological signal;
grouping ones of the dipole estimation results with a same direction out of the dipole estimation results as grouped dipole estimation results;
displaying the grouped dipole estimation results in a manner superimposed on a plurality of biological tomographic images sliced in a predetermined direction; and
displaying a non-grouped dipole estimation result in a different color or form from a color or a form of the grouped dipole estimation results depending on a direction of the non-grouped dipole estimation result.

9. A biological signal measurement system comprising:
a measuring apparatus configured to measure one or more biological signals of a subject;
a server configured to record the one or more biological signals measured by the measuring apparatus;
an information processing apparatus configured to analyze the one or more biological signals recorded in the server; and
a display controller configured to,
determine directions of dipole estimation results of a signal source corresponding to part of biological data indicating a chronological change of a biological signal,
group ones of the dipole estimation results with a same direction out of the dipole estimation results as grouped dipole estimation results,
display the grouped dipole estimation results in a manner superimposed on a plurality of biological tomographic images sliced in a predetermined direction, and
display a non-grouped dipole estimation result in a different color or form from a color or a form of the grouped dipole estimation results depending on a direction of the non-grouped dipole estimation result.

10. The information processing apparatus according to claim 1, wherein the display controller is configured to group the dipole estimation results by clustering the dipole estimation results based on positions, the directions and intensities of the dipole estimation results.

11. The information processing apparatus according to claim 10, wherein the display controller is configured to group the dipole estimation results based on the positions, the directions and the intensities of the dipole estimation results such that ones of the dipole estimation results present at a same position but with different directions are clustered in different groups.

12. The information processing method according to claim 7, wherein the grouping groups the dipole estimation results by clustering the dipole estimation results based on positions, the directions and intensities of the dipole estimation results.

13. The information processing method according to claim 12, wherein the grouping groups the dipole estimation results based on the positions, the directions and the intensities of the dipole estimation results such that ones of the dipole estimation results present at a same position but with different directions are clustered in different groups.

14. The non-transitory computer readable recording medium according to claim 8, wherein the computer program causes the computer to group the dipole estimation results by clustering the dipole estimation results based on positions, the directions and intensities of the dipole estimation results.

15. The non-transitory computer readable recording medium according to claim 14, wherein computer program causes the computer to group the dipole estimation results based on the positions, the directions and the intensities of the dipole estimation results such that ones of the dipole estimation results present at a same position but with different directions are clustered in different groups.

16. The biological signal measuring system according to claim 9, wherein the display controller is configured to group the dipole estimation results by clustering the dipole estimation results based on positions, the directions and intensities of the dipole estimation results.

17. The biological signal measuring system according to claim 16, wherein the display controller is configured to group the dipole estimation results based on the positions, the directions and the intensities of the dipole estimation results such that ones of the dipole estimation results present at a same position but with different directions are clustered in different groups.

* * * * *